United States Patent
Gunel et al.

(10) Patent No.: US 9,464,323 B2
(45) Date of Patent: Oct. 11, 2016

(54) ASSAYS FOR DETECTING WDR62 MUTATIONS

(75) Inventors: Murat Gunel, Branford, CT (US); Richard Lifton, North Haven, CT (US); Matthew State, Branford, CT (US); Kaya Bilguvar, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 13/807,425

(22) PCT Filed: Jun. 30, 2011

(86) PCT No.: PCT/US2011/042647
§ 371 (c)(1),
(2), (4) Date: Jun. 17, 2013

(87) PCT Pub. No.: WO2012/003353
PCT Pub. Date: Jan. 5, 2012

(65) Prior Publication Data
US 2013/0261002 A1  Oct. 3, 2013

Related U.S. Application Data

(60) Provisional application No. 61/398,815, filed on Jul. 1, 2010.

(51) Int. Cl.
*C12Q 1/68*  (2006.01)

(52) U.S. Cl.
CPC ....... *C12Q 1/6883* (2013.01); *C12Q 2600/156* (2013.01)

(58) Field of Classification Search
None
See application file for complete search history.

(56) References Cited

U.S. PATENT DOCUMENTS

2007/0015194 A1 * 1/2007 Shohat et al. ............... 435/6

OTHER PUBLICATIONS

Gul et al. Neurogenetics (2006) 7: 105-110.*
Li et al. Gene 408 (2008) 104-111.*
Li et al., "A systematic method for mapping multiple loci: An application to construct a genetic network for rheumatoid arthritis," Gene, 2008, 408:104-111.
NCBI, Probe Pr006107084.1-Gene, "Bead microarray element (bead) probe for *Homo sapiens* variation," rs1548506 (www.ncbi.nlm.nih.gov/projects/genome/probe/reports/probereport.cgi?uid=6107084 (Nov. 9, 2011)).
Bilguvar et al., "Whole exome sequencing identifies recessive WDR62 mutations in severe brain malformations," Nature, Aug. 2, 2010, 467(7312):207-210.
Guerrini, "Genetic malformations of the cerebral cortex and epilepsy," Epilepsia, 2005, 46(suppl. 1):32-37.
Choi et al., "Genetic diagnosis by whole exome capture and massively parallel DNA sequencing," Proc. Natl Acad. Sci. USA, 2009, 106:19096-19101.
Ng et al., "Exome sequencing identifies the cause of a Mendelian disorder," Nature Genet., 2010, 42:30-35.
Kent et al., "The human genome browser at UCSC," Genome Res., Jun. 2002;12(6):996-1006.
Li et al., "Mapping short DNA sequencing reads and calling variants using mapping quality scores," Genome Res., 2008,18:1851-1858.
Wasserman et al., "A novel c-jun n-terminal kinase (JNK)-binding protein WDR62 is recruited to stress granules and mediates a nonclassical JNK activation," Mol. Biol. Cell, 2010, 21:117-130.
Roberts et al., "The second locus for autosomal recessive primary microcephaly (MCPH2) maps to chromosome 19q13.1-13.2," Eur. J. Hum. Genet., 1999,7:815-820.
Guerrini et al., "Abnormal development of the human cerebral cortex: genetics, functional consequences and treatment options," Trends Neurosci., 2008, 31:154-162.
Mochida and Walsh, "Molecular genetics of human microcephaly," Curr. Opin. Neural., 2001,14:151-156.

* cited by examiner

*Primary Examiner* — Juliet Switzer
(74) *Attorney, Agent, or Firm* — Riverside Law LLP

(57) ABSTRACT

The present invention relates to compositions and methods for detecting mutations in WD repeat domain 62 (WDR62).

20 Claims, 17 Drawing Sheets

ASSAYS FOR DETECTING WDR62 MUTATIONS

CROSS-REFERENCE TO RELATED APPLICATIONS

This application is the U.S. national phase application filed under 35 U.S.C. §371 claiming benefit to International Patent Application No. PCT/US2011/042647, filed on Jun. 30, 2011, which is entitled to priority under 35 U.S.C. §119(e) to U.S. Provisional Patent Application No. 61/398,815, filed on Jul. 1, 2010, each of which application is hereby incorporated herein by reference in its entirety.

BACKGROUND OF THE INVENTION

The development of the human cerebral cortex is an orchestrated process involving the generation of neural progenitors in the periventricular germinal zones, cell proliferation characterized by symmetric and asymmetric mitoses, followed by migration of post-mitotic neurons to their final destinations in six highly ordered, functionally specialized layers (2008, Bystron et al., Nature Rev. Neurosci. 9:110-122; 2009, Rakic, Nature Rev. Neurosci, 10:724-735). An understanding of the molecular mechanisms guiding these intricate processes is in its infancy, substantially driven by the discovery of rare mutations that cause malformations of cortical development (2008, Guerrini et al., Trends Neurosci, 31:154-162; 2005, Guerrini, Epilepsia 46 (suppl, 1):32-37; 2001, Guerrini and Carrozzo, Am. J. Med. Genet, 106:160-173; 2001, Mochida and Walsh, Curr. Opin. Neurol, 14:151-1563). Mapping of disease loci in putative Mendelian forms of malformations of cortical development has been hindered by marked locus heterogeneity, small kindred sizes and diagnostic classifications that may not reflect molecular pathogenesis.

Malformations of cortical development are a diverse group of often devastating structural brain disorders reflecting deranged neuronal proliferation, migration or organization. Application of traditional mapping approaches have proved to be particularly challenging for gene discovery in these syndromes, where kindreds with a single affected member are most common, linkage studies support high locus heterogeneity and recent genetic findings have fundamentally challenged previous diagnostic nosology Guerrini et al, Trends Neurosci. 31:154-162; 2001, Barkovich et al., Neurology 57; 2168-2178; 2005, Barkovich et al., Neurology 65:1873-1887). Whole-exome sequencing using next generation platforms (2009, Choi et al., Proc. Natl Acad. Sci. USA 106:19096-19101; 2010, Ng et al., Nature Genet. 42:30-35; 2009, Ng et al., Nature 461:272-276) can markedly improve gene discovery efforts in these situations.

There is a need in the art for assays for detecting recessive mutations in genes involved in cortical development in both carrier subjects and affected subjects. The present invention addresses this need in the art.

SUMMARY OF THE INVENTION

The present invention relates to the discovery that recessive mutations in WD repeat domain 62 (WDR62) are involved in a wide spectrum of neurological diseases and disorders. In one embodiment, the invention is a method of determining whether a subject has a mutation in at least one allele of WDR62. In various embodiments, the method includes the steps of: obtaining a test sample from the subject, where the test sample comprises a WDR62 nucleic acid or a fragment thereof; comparing the WDR62 nucleic acid sequence in the test sample with a control WDR62 nucleic acid sequence, where when the WDR62 nucleic acid sequence in the test sample differs from the control WDR62 nucleic acid sequence, the subject is determined to have a WDR62 imitation in at least one allele of WDR62.

The mutation detected can be any mutation of WDR62 and includes the following mutations: W224S relative to SEQ ID NO:2; Q470X relative to SEQ ID NO:2; E526K relative to SEQ ID NO:2; E526X relative to SEQ ID NO:2; a 4-bp deletion (TGCC) in exon 31 beginning at codon 1402, leading to a premature stop codon at codon 1413 (V1402 GfsX12); a nonsense mutation; a missense mutation; and and a 17-bp deletion in exon 30 leading to a frameshift at codon 1280 resulting in a premature termination codon following a novel peptide of 20 amino acids (G1280AfsX21).

In a preferred embodiment, the subject is a human. In various embodiments, the subject is a fetus, a child, an adolescent, an adult, a parent or a prospective parent. In some embodiments, the subject is a carrier subject having at least one mutation in only one allele of WDR62 and in other embodiments the subject is an affected subject having at least one mutation on each allele of WDR62.

In various embodiments, the affected subject has at least one neurological disease or disorder, including, but not limited to, intellectual disability, cerebral cortical malformation, microcephaly, agyria, pachygria, hypoplasia of the corpus callosum, lissencephaly, schizencephaly, polymicrogyria and cerebellar hypoplasia.

In some embodiments, assessment of the test sample involves the use of at least one of PCR, Northern analysis, Southern analysis, DNA array analysis, and direct sequence analysis. In one embodiment, the test sample from the subject comprises genomic DNA. In another embodiment, the test sample comprises chromosome 19 or a fragment thereof comprising 19q13.12.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising

FIGS. 2A-2F, depicts additional WDR62 mutations. a-f, Pedigree structures with mutated bases (red) and the corresponding normal alleles (green) are marked on the chromatograms (left, mutant; right, wild type). a, Families NG 26 and NG 891 harbour the identical 4-bp deletion, whereas nonsense mutations leading to premature stop codons (X) are observed in NG 30 (b) and NG 294 (d). Missense mutations affecting conserved amino acids are seen in NG 190 (e) and NG 537 (f). In NG 339 (e), a 17-bp deletion leads to a premature stop codon. g, The locations of independent mutations are indicated on the genomic organization of WDR62.

FIGS. 3A-3L, depicts representative magnetic resonance images from patients demonstrating the wide spectrum of findings associated with mutations in WDR62. a, e, i, k, Axial (a), coronal (e), sagittal (k) MRI images and three-dimensional surface rendering (i) of a control subject are shown. b, Microlissencephalic features with microcephaly, diffusely thickened cortex, loss of grey-white junction and pachygyria. c, Asymmetric microcephalic hemispheres with marked polymicrogyria (arrowheads). d, Significant polymicrogyria (black arrowheads) and open-lip schizencephaly (red arrowhead). f, Unilateral cerebellar hypoplasia (arrowhead). g, Open-lip schizencephaly (red arrowhead) and the polymicrogyric cortex, h, Unilateral brainstem atrophy (arrow). j, Three-dimensional surface rendering demonstrating craniofacial dysmorphology. l, Microcephaly, pachygyria and abnormally shaped corpus callosum (arrowheads).

FIGS. 4A-4E, depicts the results of studies evaluating Wdr62 expression in the developing mouse brain. a, Wdr62 expression is enriched in the ventricular and subventricular zones (VZ and SVZ, respectively) as seen with in situ hybridization. b, WDR62 protein (red) distribution reveals a similar pattern. CP, cortical plate. c, d, WDR62 (red) localizes to the nuclei and is expressed by neural stem cells and intermediate progenitors, as marked by SOX2 and TBR2 expression (green), respectively. e, Immunofluorescent staining for α-tubulin (cytoplasmic, blue), SOX2 (nuclear, green) and WDR62 (red) in E12.5 cortical neural progenitor cells reveals that the distribution of the WDR62 overlaps with that of SOX2 and is predominantly nuclear. (Nuclear staining by 4',6-diamidino-2-phenylindole (DAPI) (blue) in b-d; rightmost panels are composite images in b-e).

FIGS. 9a-9i, depicts Wdr62 expression in the developing mouse brain. a-c, Whole mount in situ hybridization at E9.5 to E11.5. Lateral (panels a and c) and frontal views (panel b) are shown. Wdr62 mRNA is detected in the telencephalon (tel), diencephalon (di), mesencephalon (mes), metencephalon (met), branchial arch (ba), nasal process (lip), forelimb bud (flb), hindlimb bud (blb), somites (s) and tail (t). d-f, Coronal sections of the developing forebrain at three different rostrocaudal levels at embryonic day 14.5 (E14.5) are shown. Wdr62 expression is detected in proliferating neuronal progenitors in the neuroepithelium of the neocortex (nctx), striatum (str) and septum (se). g-h, Sagittal (g) and axial (h) sections of the cerebellum at E17.5 and postnatal day 7 (P7) mouse. Wdr62 mRNA is detected in proliferating granule neuron precursors in the external granular layer (egl) of the developing cerebellum (cb). Expression is absent from the inferior colliculus (ic) and the medulla (mcd). i, Coronal section of the forebrain of P21 mouse. Wdr62 mRNA expression is detected at low levels in the hippocampus (hip) and piriform cortex (pir). Scale bars: 0.2 mm (a, g to i), 0.5 mm (panels b to 0.

FIGS. 10a-10b, depicts WDR62 expression in the developing human brain. a, Immunohistochemical staining in 20 weeks of gestation human fetal neocortex: In the developing human brain, similar to the mouse brain, WDR62 is enriched in the ventricular and subventricular zones (VZ and SVZ, respectively) and weakly present in the cortical plate (CP) (scale bar: 200 μm). iVZ: inner ventricular zone; oSVZ: outer subventricular zone; IZ: intermediate zone; SP: subplate; MZ: marginal zone, b, In VZ cells near the ventricular surface, WDR62 is localized to nuclei (arrows) (scale bar: 5 μm).

FIG. 11, comprising

130, 2010). Scale bar: 10 μm. b, Subcellular fractionation of mouse E14.5 neocortex and immunoblotting for WDR62 (using rabbit anti-WDR62 antibody, Novus) reveal that WDR62 is present in the nuclear fraction.

Figure 12A:
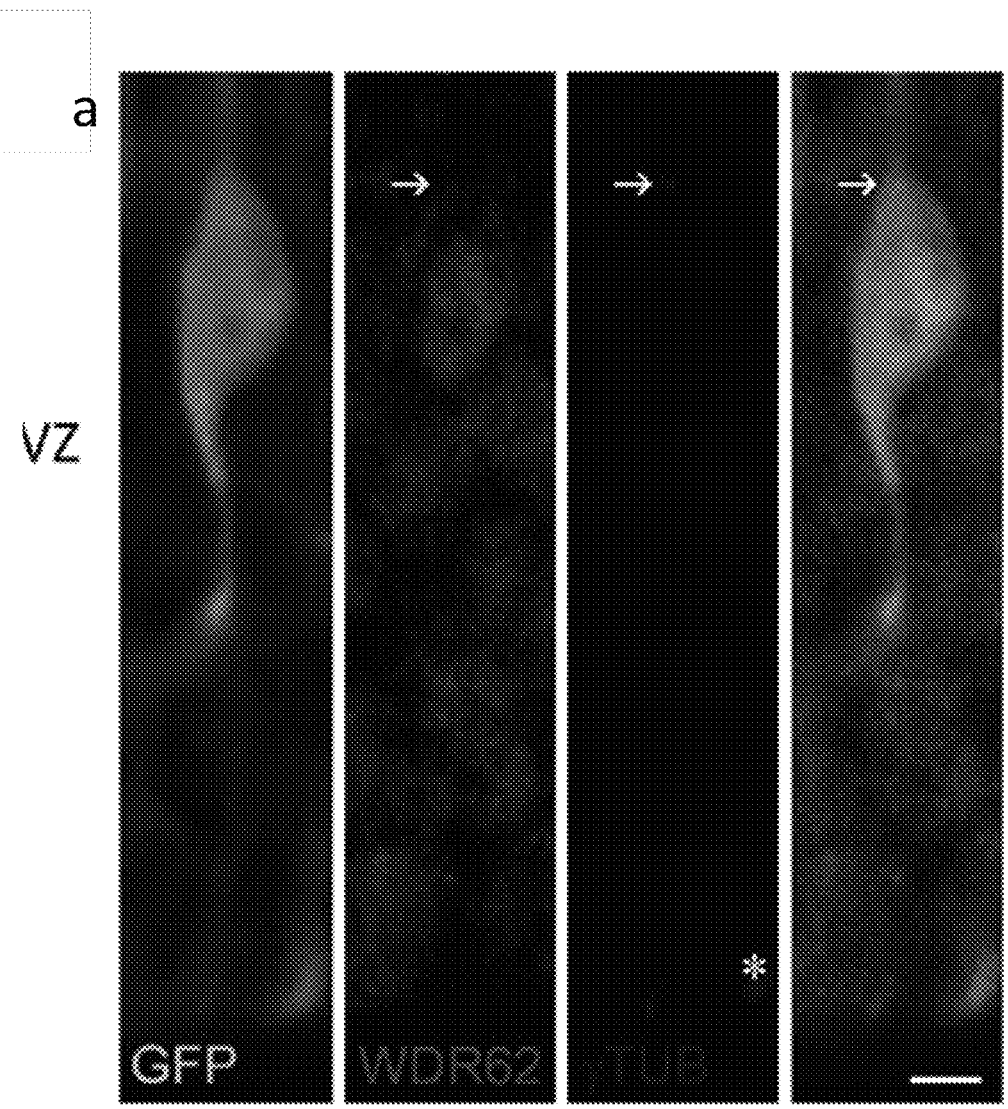
Figure 12B:
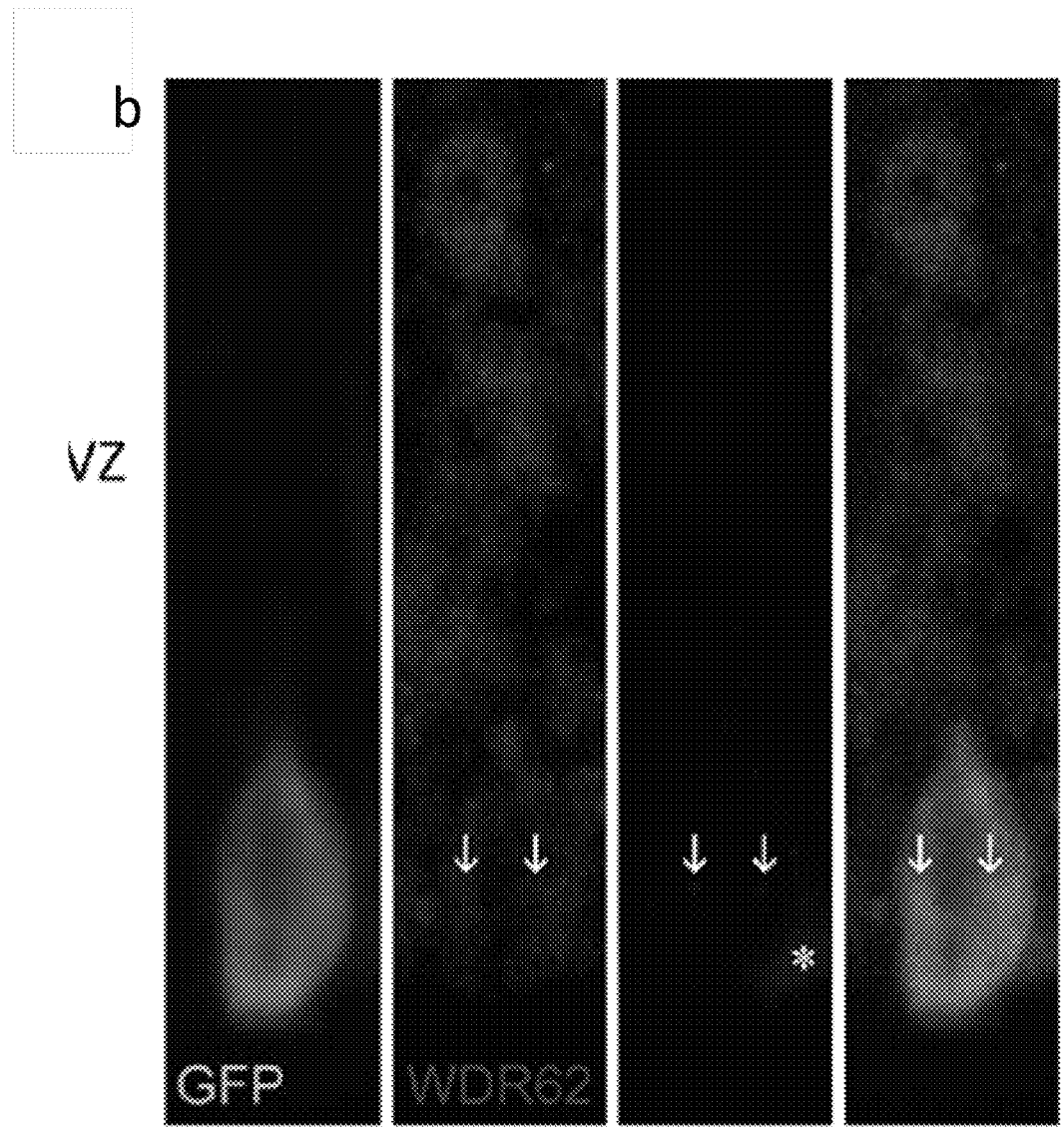

FIG. 12, comprising FIGS. 12a-12b, depicts the results of experiments using immunofluorescent staining of E15.5 mouse neocortex electroporated in utero with CAG-GFP at E13.5. a, In a GFP-filled VZ cell positioned away from the ventricular surface, WDR62 localization is nuclear and does not overlap with the single centrosome (arrow) marked by γ-tubulin (blue). Radial glial endfoot staining of γ-tubulin is indicated (asterisk). b, In a GFP-filled mitotic cell in metaphase at the ventricular surface, WDR62 is relocalized to the cytoplasm upon chromatin condensation and the breakdown of the nuclear membrane and does not apparently co-localize with the two centrosomes (arrows) marked by γ-tubulin. Scale bar: 5 μm in a, b. Composite images are shown as the right most images.

DETAILED DESCRIPTION

The present invention relates to the discovery that recessive mutations in WD repeat domain 62 (WDR62) are involved in a wide spectrum of neurological diseases and disorders, including, but not limited to, intellectual disability, cerebral cortical malformations, microcephaly, agyria, pachygria, hypoplasia of the corpus callosum, lissencephaly, schizencephaly, polymicrogyria and cerebellar hypoplasia. In various embodiments, the invention relates to a genetic screening assay of a subject to determine whether the subject has a mutation in at least one allele of WDR62. In some embodiments, the subject is a parent. In other embodiments, the subject is a prospective parent. In another embodiment, the subject is child. In a further embodiment, the subject is a fetus.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein the terms "defect," "alteration," "variation," or "mutation," refers to a mutation in WDR62 that affects the function, activity, expression (transcription or translation) or conformation of the polypeptide that it encodes. Mutations encompassed by the present invention can be any mutation of WDR62 gene that results in the disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

As used herein, the term "control nucleic acid" is meant to refer to a nucleic acid sample (e.g., RNA, DNA) that does not come from a subject known to have a mutation in WRD62 (control subject). For example, the control can be a wild type WDR62 nucleic acid sequence which does not contain a variation in its nucleic acid sequence. Also, as used herein, a control can be a fragment or portion of WRD62 that does not include the defect/variation that is the mutation of interest (that is, the mutation to be detected in an assay).

The term, "fragment," as used herein, indicates that the portion of the gene, DNA, mRNA or cDNA is a polynucleotide of a length that is sufficient to identify it as a fragment of WDR62. In one representative embodiment, a fragment comprises one or more exons of the WDR62 gene. In another representative embodiment, a fragment comprises part of an exon of the WDR62 gene. In some embodiments, the fragment can also include an intron/exon junction of the WDR62 gene.

As used herein, "homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 31ATTGCC5' and 3'TATGGC share 50% homology.

As used herein, "homology" is used synonymously with "identity." In addition, when the term "homology" is used herein to refer to the nucleic acids and proteins, it should be construed to be applied to homology at both the nucleic acid and the amino acid levels. The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al, (1990, J. Mol. Biol. 215:403-410), and can be accessed, for example, at the National Center for Biotechnology Information (NCBI) world wide web site having the universal resource locator www.ncbi.nlm.nih.gov/BLAST/. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res, 25:3389-3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See www.ncbi.nlm.nih.gov. The percent identity between two sequences can be determined using techniques similar to those described above, with or without allowing gaps. In calculating percent identity, typically exact matches are counted.

As used herein a "probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, a linkage other than a phosphodiester bond may join the bases in probes, so long as it does not interfere with hybridization. Thus, probes may be peptide nucleic acids in which the constituent bases are joined by peptide bonds rather than phosphodiester linkages.

The term "match," "perfect match," "perfect match probe" or "perfect match control" refers to a nucleic acid that has a sequence that is perfectly complementary to a particular target sequence. The nucleic acid is typically perfectly complementary to a portion (subsequence) of the target sequence. A perfect match (PM) probe can be a "test probe", a "normalization control" probe, an expression level control probe and the like. A perfect match control or perfect match is, however, distinguished from a "mismatch" or "mismatch probe."

The term "mismatch," "mismatch control" or "mismatch probe" refers to a nucleic acid whose sequence is not perfectly complementary to a particular target sequence. As a non-limiting example, for each mismatch (MM) control in a high-density probe array there typically exists a corresponding perfect match (PM) probe that is perfectly complementary to the same particular target sequence. The mismatch may comprise one or more bases. While the mismatch (es) may be located anywhere in the mismatch probe, terminal mismatches are less desirable because a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

A homo-mismatch substitutes an adenine (A) for a thymine (T) and vice versa and a guanine (G) for a cytosine (C) and vice versa. For example, if the target sequence was: AGGTCCA, a probe designed with a single homo-mismatch at the central, or fourth position, would result in the following sequence: TCCTGGT.

In one embodiment, pairs are present in perfect match and mismatch pairs, one probe in each pair being a perfect match to the target sequence and the other probe being identical to the perfect match probe except that the central base is a homo-mismatch. Mismatch probes provide a control for non-specific binding or cross-hybridization to a nucleic acid in the sample other than the target to which the probe is directed. Thus, mismatch probes indicate whether hybridization is or is not specific. For example, if the target is present, the perfect match probes should be consistently brighter than the mismatch probes because fluorescence intensity, or brightness, corresponds to binding affinity. (See e.g., U.S. Pat. No. 5,324,633, which is incorporated herein for all purposes.) Finally, the difference in intensity between the perfect match and the mismatch probe (I(PM)-I(MM)) provides a good measure of the concentration of the hybridized material. See PCT No WO 98/11223, which is incorporated herein by reference for all purposes.

Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure.

A "genome" is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

The term "chromosome" refers to the heredity-bearing gene carrier of a cell which is derived from chromatin and which comprises DNA and protein components (especially histones). The conventional internationally recognized individual human genome chromosome numbering system is employed herein. The size of an individual chromosome can vary from one type to another within a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2 \times 10^8$ by while the smallest chromosome, chromosome no. 22, contains about $5.3 \times 10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

An "allele" refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variants", "polymorphisms", or "mutations."

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein the term "isolated," such as in the expression "isolated nucleic acid" or "isolated polypeptide" means altered "by the hand of man" from its natural state (i.e. if it occurs in nature, it has been changed or removed from its ordinary context) or it has been synthesized in a non-natural environment (e.g., artificially synthesized). These terms do not require absolute purity (such as a homogeneous preparation). For example, a protein/peptide naturally present in a living organism is not "isolated", but the same protein separated from the coexisting materials of its natural state is "isolated" as this term is employed herein.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The terms "array" and "microarray" refers broadly to both "DNA microarrays" and "DNA chip(s)," and encompasses all art-recognized solid supports, and all art-recognized methods for affixing nucleic acid molecules thereto or for synthesis of nucleic acids thereon. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744, 305, 5,677,195, 5,800,992, 6,040,193, 5,424,186 and Fodor et al., 1991, Science, 251:767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789, 162, 5,708,153, 6,040,193 and 5,800,992, which are hereby incorporated by reference in their entirety for all purposes.)

Assays for amplification of the known sequence are also disclosed. For example primers for PCR may be designed to amplify regions of the sequence. For RNA, a first reverse transcriptase step may be used to generate double stranded DNA from the single stranded RNA. The array may be designed to detect sequences from an entire genome; or one or more regions of a genome, for example, selected regions of a genome such as those coding for a protein or RNA of interest; or a conserved region from multiple genomes; or multiple genomes, Arrays and methods of genetic analysis using arrays is described in Cutler, et al., 2001, Genome Res. 11(11): 1913-1925 and Warrington, et al., 2002, Hum Mutat 19:402-409 and in US Patent Pub No 20030124539, each of which is incorporated herein by reference in its entirety.

Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

Hybridization "probes" are oligonucleotides capable of binding in a base-specific manner to a complementary strand of nucleic acid. Such probes include peptide nucleic acids, as described in Nielsen et al., 1991, Science 254, 1497-1500, and other nucleic acid analogs and nucleic acid mimetics. See U.S. Pat. No. 6,156,501.

The term "hybridization" refers to the process in which two single-stranded nucleic acids bind non-covalently to form a double-stranded nucleic acid; triple-stranded hybridization is also theoretically possible. Complementary sequences in the nucleic acids pair with each other to form a double helix. The resulting double-stranded nucleic acid is a "hybrid." Hybridization may be between, for example tow complementary or partially complementary sequences. The hybrid may have double-stranded regions and single stranded regions. The hybrid may be, for example, DNA:DNA, RNA:DNA or DNA:RNA. Hybrids may also be formed between modified nucleic acids. One or both of the nucleic acids may be immobilized on a solid support. Hybridization techniques may be used to detect and isolate specific sequences, measure homology, or define other characteristics of one or both strands.

The stability of a hybrid depends on a variety of factors including the length of complementarity, the presence of mismatches within the complementary region, the temperature and the concentration of salt in the reaction. Hybridizations are usually performed under stringent conditions, for example, at a salt concentration of no more than 1 M and a temperature of at least 25° C. For example, conditions of 5×SSPE (750 mM NaCl, 50 mM Na Phosphate, 5 mM EDTA, pH 7.4) or 100 mM MES, 1 M Na, 20 mM EDTA, 0.01% Tween-20 and a temperature of 25-50° C. are suitable for allele-specific probe hybridizations. In a particularly preferred embodiment, hybridizations are performed at 40-50° C. Acetylated BSA and herring sperm DNA may be added to hybridization reactions.

The term "label" as used herein refers to a luminescent label, a light scattering label or a radioactive label. Fluorescent labels include, but are not limited to, the commercially available fluorescein phosphoramidites such as Fluoreprime (Pharmacia), Fluoredite (Millipore) and FAM (AM). See U.S. Pat. No. 6,287,778.

The term "solid support," "support," and "substrate" as used herein are used interchangeably and refer to a material or group of materials having a rigid or semi-rigid surface or surfaces. In one embodiment, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Targets are sometimes referred to in the art as anti-probes. As the term targets is used herein, no difference in meaning is intended.

A "probe target pair" is formed when two macromolecules have combined through molecular recognition to form a complex.

U.S. Pat. Nos. 5,800,992 and 6,040,138 describe methods for making arrays of nucleic acid probes that can be used to detect the presence of a nucleic acid containing a specific nucleotide sequence. Methods of forming high-density arrays of nucleic acids, peptides and other polymer sequences with a minimal number of synthetic steps are known. The nucleic acid array can be synthesized on a solid substrate by a variety of methods, including, but not limited to, light-directed chemical coupling, and mechanically directed coupling. For additional descriptions and methods relating to arrays see U.S. patent application Ser. Nos. 10/658,879, 60/417,190, 09/381,480, 60/409,396, 5,861,242, 6,027,880, 5,837,832, 6,723,503 and PCT Pub No 03/060526 each of which is incorporated herein by reference in its entirety.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Sample" or "biological sample" as used herein means a biological material isolated from a subject. The biological sample may contain any biological material suitable for detecting a WDR62 sequence mutation, and may comprise cellular and/or non-cellular material obtained from the individual.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Standard codon/amino acid designators:

| Codon | Amino Acid | 3-Letter Abbreviation | 1-Letter Abbreviation |
|---|---|---|---|
| TTT | Phenylalanine | Phe | F |
| TTC | Phenylalanine | Phe | F |
| TTA | Leucine | Leu | L |
| TTG | Leucine | Leu | L |
| TCT | Serine | Ser | S |
| TCC | Serine | Ser | S |
| TCA | Serine | Ser | S |
| TCG | Serine | Ser | S |
| TAT | Tyrosine | Tyr | Y |
| TAC | Tyrosine | Tyr | Y |
| TAA | Termination | Ter | X |
| TAG | Termination | Ter | X |
| TGT | Cysteine | Cys | C |
| TGC | Cysteine | Cys | C |
| TGA | Termination | Ter | X |
| TGG | Tryptophan | Trp | W |
| CTT | Leucine | Leu | L |
| CTC | Leucine | Leu | L |
| CTA | Leucine | Leu | L |
| CTG | Leucine | Leu | L |
| CCT | Proline | Pro | P |
| CCC | Proline | Pro | P |
| CCA | Proline | Pro | P |
| CCG | Proline | Pro | P |
| CAT | Histidine | His | H |
| CAC | Histidine | His | H |
| CAA | Glutamine | Gln | Q |
| CAG | Glutamine | Gln | Q |
| CGT | Arginine | Arg | R |
| CGC | Arginine | Arg | R |
| CGA | Arginine | Arg | R |

-continued

| Codon | Amino Acid | 3-Letter Abbreviation | 1-Letter Abbreviation |
|---|---|---|---|
| CGG | Arginine | Arg | R |
| ATT | Isoleucine | Ile | I |
| ATC | Isoleucine | Ile | I |
| ATA | Isoleucine | Ile | I |
| ATG | Methionine | Met | M |
| ACT | Threonine | Thr | T |
| ACC | Threonine | Thr | T |
| ACA | Threonine | Thr | T |
| ACG | Threonine | Thr | T |
| AAT | Asparagine | Asn | N |
| AAC | Asparagine | Asn | N |
| AAA | Lysine | Lys | K |
| AAG | Lysine | Lys | K |
| AGT | Serine | Ser | S |
| AGC | Serine | Ser | S |
| AGA | Arginine | Arg | R |
| AGG | Arginine | Arg | R |
| GTT | Valine | Val | V |
| GTC | Valine | Val | V |
| GTA | Valine | Val | V |
| GTG | Valine | Val | V |
| GCT | Alanine | Ala | A |
| GCC | Alanine | Ala | A |
| GCA | Alanine | Ala | A |
| GCG | Alanine | Ala | A |
| GAT | Aspartate | Asp | D |
| GAC | Aspartate | Asp | D |
| GAA | Glutamate | Glu | E |
| GAG | Glutamate | Glu | E |
| GGT | Glycine | Gly | G |
| GGC | Glycine | Gly | G |
| GGA | Glycine | Gly | G |
| GGG | Glycine | Gly | G |

DESCRIPTION

The present invention relates to the discovery that recessive mutations in WD repeat domain 62 (WDR62) are involved in a wide spectrum of neurological diseases and disorders, including, but not limited to, intellectual disability, cerebral cortical malformations, microcephaly, agyria, pachygria, hypoplasia of the corpus callosum, lissencephaly, schizencephaly, polymicrogyria, seizures and cerebellar hypoplasia.

In various embodiments, the invention relates to a genetic screening assay of a subject to determine whether the subject has a mutation in WDR62. In some embodiments, the subject is a parent. In other embodiments, the subject is a prospective parent. In another embodiment, the subject is child. In a further embodiment, the subject is a fetus.

The present invention provides methods of assessing for the presence or absence of a genetic mutation in WDR62, as well as methods of diagnosing a subject having a mutation in WDR62, and methods of assessing a subject for carrier status for a mutation in WDR62. As described herein, certain mutations of WDR62 are associated with a wide spectrum of intellectual disabilities and cerebral cortical malformations, including, but not limited to, microcephaly, pachygria with cortical thickening, hypoplasia of the corpus callosum, lissencephaly, schizencephaly, polymicrogyria and cerebellar hypoplasia. The mutations in WDR62 described herein are alterations (e.g., deletions, insertions, or transitions) in the nucleic acid sequence of WDR62. The position of the mutations in the sequence of WDR62 are numbered in relation to the nucleic acid or amino acid sequence. That is, the numbered position of an altered nucleotide, or amino acid, is the position number of that nucleotide, or amino acid, in the nucleic acid or amino acid sequence. WDR62 maps to chromosome 19q13.12 and encodes 1,523 amino acids. The nucleic acid and amino acid sequence of WDR62 is set forth in GenBank accession number NM_001083961 (herein SEQ ID NOS:1 and 2). WDR62 maps to chromosome 19q13.12 and encodes a polypeptide having 1,523 amino acids. The WRD62 mutations useful in the methods of the invention include, but are not limited to, the following: W224S; Q470X; E526K; E526X; a 4-bp deletion (TGCC) in exon 31 beginning at codon 1402, leading to a premature stop codon at codon 1413 (V1402 GfsX12); a nonsense mutation leading to a premature stop codon; a missense mutation affecting a conserved amino acid; and a 17-bp deletion in exon 30 leading to a frameshift at codon 1280 resulting in a premature termination codon following a novel peptide of 20 amino acids (G1280AfsX21).

In the methods of the invention, a test sample from a subject is assessed for the presence of one or more mutations in WDR62. In some embodiments, the subject is a human subject, and may be of any race and any age, including fetus, infant, juvenile, adolescent, and adult. Representative subjects include those who have not previously been diagnosed as being affected by a mutation in WDR62 or as being a carrier of a mutation in WDR62, as well as those who have been determined to be at risk for having a mutation in WDR62 or for being a carrier of a mutation in WDR62, and those who have been initially diagnosed as being affected by mutation in WDR62 where confirming information is desired.

In one embodiment, the test sample is a sample containing at least a fragment of a nucleic acid of WDR62, including WDR62DNA or a fragment of WDR62 DNA, WDR62 mRNA or a fragment of WDR62 mRNA, and WDR62 cDNA or a fragment of WDR62 cDNA, from the subject. The term, "fragment," as used herein, indicates that the portion of the gene, DNA, mRNA or cDNA is a polynucleotide of a length that is sufficient to identify it as a fragment of WDR62. In one representative embodiment, a fragment comprises one or more exons of the WDR62 gene. In another representative embodiment, a fragment comprises part of an exon of the WDR62 gene. In some embodiments, the fragment can also include an intron/exon junction of the WDR62 gene.

The test sample is prepared from a biological sample obtained from the subject. The biological sample can be a sample from any source which contains nucleic acid (e.g., DNA (e.g., chromosomal nucleic acid) or RNA), such as a blood, amniotic fluid, cerebrospinal fluid, or tissue such as, by way of example, skin, muscle, buccal mucosa, conjunctival mucosa, placenta, gastrointestinal tract or other organs. A biological sample of nucleic acid from fetal cells or tissue can be obtained by appropriate methods, such as by amniocentesis or chorionic villus sampling (direct or cultured). In certain embodiments, a biological sample containing genomic DNA is used. A biological sample can be used as the test sample; alternatively, a biological sample can be processed to enhance access to nucleic acids, or copies of nucleic acids (e.g., copies of nucleic acids comprising WDR62), and the processed biological sample can then be used as the test sample. For example, in one embodiment, cDNA is prepared from a biological sample comprising mRNA, for use in the methods. Alternatively or in addition, if desired, an amplification method can be used to amplify nucleic acids comprising all or a fragment of WDR62 in a biological sample, for use as the test sample in the assessment for the presence or absence of a mutation in WDR62.

The test sample is assessed to determine whether one or more mutations are present in the WDR62 sequence of the subject. In general, detecting a mutation may be carried out by determining the presence or absence of nucleic acids containing a mutation of interest in the test sample.

In some embodiments, hybridization methods, such as Southern analysis, Northern analysis, or in situ hybridizations, can be used (see Current Protocols in Molecular Biology, Ausubel, F. et al., eds., John Wiley & Sons, including all supplements). For example, the presence of a mutation can be indicated by hybridization of nucleic acid in the genomic DNA, RNA, or cDNA to a nucleic acid probe. A "nucleic acid probe", as used herein, can be a DNA probe or an RNA probe; the nucleic acid probe can contain at least one polymorphism of interest, as described herein. The probe can be, for example, the gene, a gene fragment (e.g., one or more exons), a vector comprising the gene, a probe or primer, etc. For representative examples of use of nucleic acid probes, see, for example, U.S. Pat. Nos. 5,288,611 and 4,851,330.

To detect one or more mutations of interest, a hybridization sample is formed by contacting the test sample with at least one nucleic acid probe. A preferred probe for detecting mRNA or genomic DNA is a labeled nucleic acid probe capable of hybridizing to mRNA or genomic DNA of WDR62. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target mRNA, cDNA or genomic DNA. The hybridization sample is maintained under conditions which are sufficient to allow specific hybridization of the nucleic acid probe to mRNA, cDNA or genomic DNA of WDR62. "Specific hybridization," as used herein, indicates exact hybridization (e.g., with no mismatches). Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe and WDR62 gene, mRNA or cDNA in the test sample, the mutation that is present in the nucleic acid probe is also present in the WDR62 of the subject. More than one nucleic acid probe can also be used concurrently in this method. Specific hybridization of any one of the nucleic acid probes is indicative of the presence of the mutation of interest, as described herein.

In Northern analysis (see Current Protocols in Molecular Biology, Ausubel, F. et al., eds., John Wiley & Sons, supra), the hybridization methods described above are used to identify the presence of a mutation of interest. For Northern analysis, a test sample comprising RNA is prepared from a biological sample from the subject by appropriate means. Specific hybridization of a nucleic acid probe, as described above, to RNA from the subject is indicative of the presence of a mutation of interest, as described herein.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a WDR62 sequence comprising one or more mutations of interest. Hybridization of the PNA probe to a WDR62 sequence is indicative of the presence of the polymorphism of interest.

In another embodiment of the methods of the invention, mutation analysis by restriction digestion can be used to detect a WDR62 mutation, if the mutation results in the creation or elimination of a restriction site. A sample containing nucleic acid from the subject is used. Polymerase chain reaction (PCR) can be used to amplify all or a fragment of WDR62 (and, if necessary, the flanking sequences) in the sample. RFLP analysis is conducted as described (see Current Protocols in Molecular Biology, supra). The digestion pattern of the relevant fragments indicates the presence or absence of mutation in WDR62.

Direct sequence analysis can also be used to detect specific mutations in WDR62. A sample comprising DNA or RNA is used, and PCR or other appropriate methods can be used to amplify all or a fragment of WDR62, and/or its flanking sequences, if desired. The sequence WDR62, or a fragment thereof (e.g., one or more exons), or cDNA, or fragment of the cDNA, or mRNA, or fragment of the mRNA, is determined, using standard methods. The sequence of the gene, gene fragment, cDNA, cDNA fragment, mRNA, or mRNA fragment is compared with the known nucleic acid sequence of WDR62, as appropriate. The presence of a mutation can then be identified.

Allele-specific oligonucleotides can also be used to detect the presence of a mutation of WDR62, through, for example, the use of dot-blot hybridization of amplified oligonucleotides with allele-specific oligonucleotide (ASO) probes (see, for example, 1986, Saiki et al., Nature 324:163-166). An "allele-specific oligonucleotide" (also referred to herein as an "allele-specific oligonucleotide probe") is an oligonucleotide of approximately 10-50 base pairs, preferably approximately 15-30 base pairs, that specifically hybridizes to the WDR62 sequence, and that contains a mutation. An allele-specific oligonucleotide probe that is specific for a particular mutation can be prepared, using standard methods (see Current Protocols in Molecular Biology, supra). To identify a mutation, a sample comprising nucleic acid is used. PCR can be used to amplify all or a fragment of WDR62. The nucleic acid containing the amplified WDR62 sequence (or fragment of WDR62) is dot-blotted, using standard methods (see Current Protocols in Molecular Biology, supra), and the blot is contacted with the oligonucleotide probe. The presence of specific hybridization of the probe to the amplified WDR62 nucleic acid is then detected. Specific hybridization of an allele-specific oligonucleotide probe to nucleic acid from the subject is indicative of the presence of a mutation of interest.

In another embodiment of the invention, fluorescence resonance energy transfer (FRET) can be used to detect the presence of a mutation, FRET is the process of a distance-dependent excited state interaction in which the emission of one fluorescent molecule is coupled to the excitation of another. A typical acceptor and donor pair for resonance energy transfer consists of 4-[[4-(dimethylamino) phenyl] azo]benzoic acid (DABCYL) and 5-[(2-aminoethylamino] naphthalene sulfonic acid (EDANS). EDANS is excited by illumination with 336 nm light, and emits a photon with wavelength 490 n.times.n. If a DABCYL moiety is located within 20 angstroms of the EDANS, this photon will be efficiently absorbed. DABCYL and MANS will be attached to two different oligonucleotide probes designed to hybridize head-to-tail to nucleic acid adjacent to and/or overlapping the site of one of the imitations of interest. Melting curve analysis is then applied: cycles of denaturation, cooling, and re-heating are applied to a test sample mixed with the oligonucleotide probes, and the fluorescence is continuously monitored to detect a decrease in DABCYL fluorescence or an increase in EDANS fluorescence (loss of quenching). While the two probes remain hybridized adjacent to one another, FRET will be very efficient. Physical separation of the oligonucleotide probes results in inefficient FRET, as the two dyes are no longer in close proximity. The presence or absence of a mutation of interest can be assessed by comparing the fluorescence intensity profile obtained from the test sample, to fluorescence intensity profiles of control samples comprising known mutations of interest in WDR62.

In another embodiment, arrays of oligonucleotide probes that are complementary to target nucleic acid sequence segments from a subject can be used to identify mutations in WDR62. For example, in one embodiment, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a nucleic acid of interest is hybridized with the array and scanned for mutations. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein. In brief, a target nucleic acid sequence which includes one or more previously identified mutations or markers is amplified by well-known amplification techniques, e.g., PCR. Typically, this involves the use of primer sequences that are complementary to the two strands of the target sequence both upstream and downstream of the mutation. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although often described in terms of a single detection block, e.g., for detection of a single mutation, arrays can include multiple detection blocks, and thus be capable of analyzing multiple, specific mutations. In alternate arrangements, it will generally be understood that detection blocks may be grouped within a single array or in multiple, separate arrays so that varying, optimal conditions may be used during the hybridization of the target to the array. This allows for the separate optimization of hybridization conditions for each situation. Additional description of use of oligonucleotide arrays for detection of polymorphisms can be found, for example, in U.S. Pat. Nos. 5,858,659 and 5,837,832, the entire teachings of which are incorporated by reference herein.

Other methods of nucleic acid analysis can be used to detect mutations of interest. Representative methods include direct manual sequencing (1988, Church and Gilbert, Proc. Natl. Acad. Sci. USA 81:1991-1995; 1977, Sanger et al., Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (1981, Sheffield et al., Proc. Natl. Acad. Sci. USA 86; 232-236), mobility shift analysis (1989, Orita et al., Proc. Natl. Acad. Sci. USA 86:2766-2770; 1987, Rosenbaum and Reissner, Biophys. Chem. 265:1275; 1991, Keen et al., Trends Genet. 7:5); restriction enzyme analysis (1978, Flavell et al., Cell 15:25; 1981, Geever, et al., Proc. Natl. Acad. Sci. USA 78:5081); heteroduplex analysis; chemical mismatch cleavage (CMC) (1985, Cotton et al., Proc. Natl. Acad. Sci. USA 85:4397-4401); RNase protection assays (1985, Myers, et al., Science 230:1242); use of polypeptides which recognize nucleotide mismatches, such as E, coli mutS protein (see, for example, U.S. Pat. No. 5,459,039); Luminex xMAR™ technology; and/or allele-specific PCR, for example.

These and other methods can be used to identify the presence of one or more mutations of interest in WDR62. For example, in certain embodiments, the methods can be used to assess both the first and the second alleles of WDR62 of a subject for the presence of one or more mutations. The terms, "first" and "second" alleles are arbitrarily applied to the two alleles; that is, either allele may be designated as the "first" allele, and the other allele is then designated as the "second" allele.

In another embodiment of the invention, the methods of assessing a test sample for the presence or absence of a imitation in WDR62, as described herein, are used to diagnose in a subject affected by a disorder associated with a mutation in WDR62. The two alleles of the affected subject may have the same mutation present, or may have different mutations. Furthermore, more than one mutation may be found in one or both alleles. In these methods, at least one mutation is found in at least one of the two alleles of WDR62 (the "first" allele). In addition, in affected subjects, at least one mutation in WDR62 is present on the other allele of WDR62 (the "second" allele).

In a further embodiment of the invention, the methods of assessing a test sample for the presence or absence of a mutation in WDR62, as described herein, are used to diagnose carrier status of a subject for a mutation in WDR62. The term, "carrier status," indicates that the subject carries mutation of interest in only one allele of WDR62, and thus is considered a carrier for this recessive disorder. In these methods, at least one mutation is found in only one of the two alleles of WDR62 (in the "first" allele). In addition, no mutations in WDR62 are found in the second allele, although it should be noted that benign sequence changes may also be present in either or both alleles of WDR62.

The present invention also pertains to kits useful in the methods of the invention. Such kits comprise components useful in any of the methods described herein, including for example, hybridization probes or primers (e.g., labeled probes or primers), reagents for detection of labeled molecules, restriction enzymes (e.g., for RFLP analysis), allele-specific oligonucleotides, means for amplification of WDR62 nucleic acids, or means for analyzing the nucleic acid sequence of WDR62 and instructional materials. For example, in one embodiment, the kit comprises components useful for analysis of WDR62 mutations. In a preferred embodiment of the invention, the kit comprises components for detecting one or more of the mutations of WDR62.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Whole Exome Sequencing Identifies Recessive WDR62 Mutations in Severe Brain Malformations It is demonstrated herein using whole-exome sequencing that recessive mutations in WD repeat domain 62 (WDR62) are the cause of a wide spectrum of severe cerebral cortical malformations including microcephaly, pachygria with cortical thickening as well as hypoplasia of the corpus callosum (see 2010, Bilguvar et al., Nature 467:207-210). Some patients with mutations in WDR62 had evidence of additional abnormalities including lissencephaly, schizencephaly, polymicrogyria and, in one instance, cerebellar hypoplasia, all traits traditionally regarded as distinct entities.

In mice and humans, WDR62 transcripts and protein are enriched in neural progenitors within the ventricular and subventricular zones. Expression of WDR62 in the neocortex is transient, spanning the period of embryonic neurogenesis. Unlike other known microcephaly genes, WDR62 does not apparently associate with centrosomes and is predominantly nuclear in localization, as demonstrated herein. These findings unify previously disparate aspects of cerebral cortical development and highlight the use of whole-exome sequencing to identify disease loci in settings in which traditional methods have proved challenging.

The materials and methods employed in these experiments are now described.

Human Subjects

The study protocol was approved by the Yale Human Investigation Committee. Approvals from institutional review boards for genetic studies, and written consent from all study subjects, were obtained at the participating institutions.

MRI Sequences

MRI examinations presented were performed with a 3-T scanner (Trio, Siemens).

Illumina Genotyping

Whole-genome genotyping of the samples was performed on the Illumina Platform with Illumina Human 370K Duo or 610K Quad Beadehips using the manufacturer's protocol. The image data were normalized and the genotypes were called using data analysis software (Bead Studio, Illumina). Linkage analysis was performed using Allegro version 2.0 software (DeCode Genetics).

Sanger Sequencing

The exons and exon-intron boundaries of WDR62 were determined using the University of California, Santa Cruz (UCSC) Genome Browser (genome.ucsc.edu); unique primers were designed using Sequencher 4.8 (Gene Codes) and synthesized by Invitrogen. The fragments were amplified, purified and direct re-sequencing was performed using ABI's 9800 Fast Thermocyclers. The amplicons were analysed on an 3730xL DNA Analyser (Applied Biosystems).

Targeted Sequence Capture

Genomic DNA of sample NG 26-1 was captured on a NimbleGen 2.1M Human Exome Array (based on the build of 30 Apr. 2008 of the consensus coding sequence (CCDS) database) with modifications to the manufacturer's protocol (2009, Choi et al., Proc. Natl. Acad. Sci. USA 106:19096-19101). The pre- and post-capture libraries were compared by quantitative PCR for the determination of the relative fold enrichment of the targeted sequences.

Exome Sequencing

Single-read cluster generation was performed on the Cluster Station (Illumina). The captured, purified and clonally amplified library targeting the exome from patient NG 26-1 was sequenced on Genome Analyser IIx. Two lanes of single-read sequencing at a read length of 74 bp was performed following the manufacturer's protocol. Image analysis and base calling was performed by Illumina Pipeline version 1.5 with default parameters, installed on Yale University's High Performance Computing Cluster.

Targeted Exome Sequencing

Genomic DNA of sample NG 26-1 was captured on a NimbleGen 2.1M Human Exome Array with modifications to the manufacturer's protocol (2009, Choi et al., Proc. Natl. Acad. Sci. USA 106:19096-19101), followed by single-read cluster generation on the Cluster Station (Illumina). The captured, purified and clonally amplified library targeting the exome from patient NG 26-1 was then sequenced on Genome Analyser IIx. Two lanes of single-read sequencing at a read length of 74 bp was performed following the manufacturer's protocol.

Exome Sequence Analysis

The sequence reads obtained were aligned to the human genome (hg18) using Maq (2008, Li et al., Genome Res. 18:1851-1858) and BWA (2009, Li et al., Bioinformatics 25:1754-1760) software. The percentage alignment of the reads to both the reference genome as well as the targeted region, exome, was calculated using perl scripts (2009, Choi et al., Proc. Natl Acad. Sci. USA 106:19096-19101). Similarly, perl scripts were used for the detection of mismatch frequencies and error positions. SAMtools (2009, Li et al., Bioinformatics 25:2078-2079) was used for the detection of single-nucleotide variations on the reads aligned with Maq. The indels were detected on the reads aligned with BWA for its ability to allow for gaps during the alignment. Shared homozygous segments of the affected subjects were detected using Plink software version 1.06 (2007, Purcell et al., Am. J. Hum. Genet. 81:559-575), and the variants were filtered for shared homozygosity. The variants were annotated for novelty compared with both dbSNP (build 130) and nine personal genome databases and previous exome sequencing experiments performed by the human genomics group. Novel variants were further evaluated for their impact on the encoded protein, conservation across 44 vertebrate species,

*Caenorhabditis elegans* and *Drosophila melanogaster*, expression patterns and potential overlap with known microRNAs.

Functional Annotation

Published microarray data sets of E9.5, E11.5 and E13.5 mouse brain tissue (GSE8091) were downloaded from the GEO database (www.ncbi.nlm.nih.gov/projects/geo/query/acc.cgi) (2008, Hartl et al., 8:1257-1265) and processed using R statistical program (Affy package) (2003, Irizarry et al., Nucleic Acids Res, 31:e15). Genes that correlated highly with Wdr62 (Bonferroni corrected P<0.01) were functionally annotated using DAVID tools (david.abcc.ncifcrf.gov) (2009, Huang et al., Nature Protocols 4:44-57).

Animals

Experiments were performed in accordance with protocols approved by the Institutional Animal Care and Use Committee at Yale University School of Medicine.

In Situ Hybridization

Sections and wholemount embryos were processed for non-radioactive in situ hybridization as described previously with minor modifications (2009, Stillman et al., J. Comp. Neurol. 513; 21-37). An RNA probe complementary to mouse Wdr62 (bases 3,525-4,480, relative to SEQ ID NO: 3, of the mouse Wdr62 complementary DNA, NCBI Reference Sequence: NM_146186) was prepared and labelled with digoxigenin-1'-uridine-5'-triphosphate. Embryos and tissue sections were analysed using a Zeiss Stemi dissecting microscope or a Zeiss Axiolmager fitted with a Zeiss Axio-Cam MRc5 digital camera. Images were captured using AxioVision AC software (Zeiss) and assembled using Adobe Photoshop.

Immunostaining and Confocal Imaging

E15.5 embryos were obtained from timed-pregnant CD-1 mice (Charles River). For timed pregnancies, midday of the day of vaginal plug discovery was considered E0.5. Dissected brains were fixed by immersion in 4% paraformaldehyde for 16 h at 4° C. and sectioned at 70 μm using a vibratome (Leica VT1000S). Human fetal brains at 19 and 20 weeks' gestation were obtained under the guidelines approved by the Yale Institutional Review Board (protocol number 0605001466) from the Human Fetal Tissue Repository at the Albert Einstein College of Medicine (CCI number 1993-042), fixed by immersion in 4% paraformaldehyde for 36 h, cryoprotected and frozen, and cryosectioned at 60 μm. For mouse sections, an unconjugated donkey anti-mouse IgG Fab fragment (Jackson Immuno Research Laboratories, 1:200) was added to block endogenous mouse IgG. Primary antibodies were diluted in blocking solution at the following concentrations: mouse anti-WDR62 (Sigma-Aldrich), 1:400; rabbit anti-SOX2 (Millipore), 1:500; rabbit anti-TBR2 (Abcam), 1:500; chicken anti-GFP (Abcam), 1:1,500; rat anti-α-tubulin (Abcam), 1:500; rabbit anti-γ-tubulin (Sigma), 1:250; standard methods were followed. Confocal images were collected using laser-scanning microscope (Zeiss LSM 510). For diaminobenzidine staining, brain sections were incubated with biotinylated secondary antibodies and processed using the ABC and diaminobenzidine kits (Vector Laboratories). Images were acquired using a digital scanner (Aperio).

Cell Culture

For neural progenitor cultures, dorsal telencephalon was dissected from E12.5 mouse embryos and enzymatically dissociated and re-suspended as previously described (2005, Abelson et al., Science 310:317-320). For cell lines, Neuro2a, HeLa and HEK-293FT cells were plated on glass coverslips coated with poly-L-ornithine (15 μg ml$^{-1}$) at $5\times10^5$ cells per square centimeter in 24-well plates. Sixteen hours after plating, the cells were fixed by immersion in 4% paraformaldehyde for 15 min at room temperature and processed for immunostaining.

Subcellular Fractionation and Western Blotting

Dorsal telencephalon was dissected from E14.5 mouse embryos and fractionated using the CelLytic nuclear extraction kit (Sigma). The manufacturer's protocol was followed with the exception that cell lysis was achieved by addition of 0.5% Triton X-100. Immunoblotting was done with primary antibodies diluted at the following concentrations: rabbit anti-WDR62 (Novus), 1:1,000; rat anti-α-tubulin (Abcam), 1:5,000.

In Utero Electroporation

CAG-GFP plasmid DNA was transfected into ventricular zone progenitors of E13.5 embryos by in utero electroporation as previously described (2008, Kwan et al., Proc. Natl. Acad. Sci. USA 105:16021-16026). At E15.5, the embryos were collected and fixed for immunostaining.

Clinical Histories of Patients with WDR62 Mutations

This study was approved by the Yale Human Investigation Committee (9406007680 (Oct. 24, 2009) and 0908005592 (Aug. 17, 2009)). Consents were obtained from all study participants by the referring physicians. IRB protocol numbers and approval dates are as follows: Istanbul: NO:C-033 (Dec. 22, 2009); Hacettepe: 2008ABH67540017 (Sep. 27, 2007); Kayseri: 2009/55 (Sep. 3, 2009); Ege: B.30.2.EGE.0.20.05.00/0M/1093-1432, #09-5.1/16, (Jun. 23, 2009).

NG 26-1 (Mutation: V1402 GfsX12)

The patient is a 4 year 6 month old female who was the product of a consanguineous union. She was brought to medical attention at 4 months of age due to small head size. At that time, her head circumference was 33 cm and she was given a diagnosis of microcephaly. Metabolic and TORCH workups were negative. She was last seen in clinic at 2 years and 3 months of age. Her head circumference was 38 cm. She showed micrognathia and a bulbous nose, and suffered from severe mental retardation. She was able to say a few words including "cat", "dad", "come", and "new", and responded to basic verbal commands. She was not toilet trained nor able to feed herself. She was able to walk and run, but could not ascend or descend stairs. Her vision and hearing were noted to be unremarkable. She has no spasticity in any of her extremities and has never experienced any seizures.

NG 30-1 (Mutation: E526X)

The patient is a 7-year-old female who is the product of a consanguineous union. The pregnancy was uneventful and the neonatal period was unremarkable. The patient presented to medical attention at 9 months of age due to small head size. On examination, she was found to have motor retardation. Her head circumference at that time was noted to be 38.5 cm and she was diagnosed with microcephaly. She had an unrevealing metabolic workup. At the age of 4, she began experiencing generalized seizures which were controlled with levetiracetam. Her last clinic visit was at the age of 6. At that visit, she was able to ambulate independently, was able to understand only basic verbal commands, had limited vocabulary, and was noted to have moderate mental retardation based on clinical examination.

NG 190-1 (Mutation: W224S)

The patient is a 6 year 5 month old boy who is the product of a consanguineous union. His peri and neonatal periods were unremarkable. He presented to medical attention at the age of 2 due to hyperactivity, seizures, and inability to sleep. The seizures were generalized, tonic/clonic, lasting approximately 1-2 minutes each and occurring on average twice a day. At that time on neurologic exam, he was able to speak 1-2 word sentences. Motor tone and bulk were grossly normal. Reflexes were within normal limits and cranial nerves were intact. At the most recent clinic visit in 2009, he continued to experience 4-8 seizures per day and was being treated with valproic acid. Physical exam revealed microcephaly and micrognathia. His head circumference was noted to be 42 cm and he had severe mental retardation based on clinical observation. He was not toilet trained, could only speak a single word, "dad", could not feed himself, and was only able to ambulate with the support of others.

NG 190-5 (Mutation: W224S)

This patient is an 8 year 7 month old female who is the product of a consanguineous marriage and the cousin of NG 190-1. The patient presented to medical attention at the age of 3 due to seizures. She is microcephalic, hyperactive, and has dysconjugate gaze. On the most recent exam her head circumference was 44 cm and she was noted to have moderate mental retardation based on clinical observation. She demonstrated poor verbal skills, but was able to early out simple activities of daily living. She had normal tone, reflexes, and no dysmetria on exam. She was able to walk independently, and had no obvious dysmorphic features. She was grossly less affected than her brother (NG 190-6) and cousin (NG 190-1).

NG 190-6 (Mutation: W224S)

This patient is a 12 year, 11 month old boy who is the product of a consanguineous marriage and is the brother of patient NG 190-5. He has a history of seizures and mental and motor retardation. He is noted to have microcephaly (current head circumference is 45 cm) and self-mutilating behaviors. On last exam, his gaze was described as dysconjugate, muscle tone was increased, and reflexes were hyperactive. He was assessed as having severe mental retardation based on clinical exam, but could ambulate independently. His symptoms are notably more severe than his sister's.

NG 294-1 (Mutation: 0470X)

The patient is a 14 year, 6 month old male two is the product of a consanguineous marriage. He has two normal siblings. His perinatal history is significant for preterm birth at 32 weeks of gestation. He was hospitalized at 27 days for bilirubinemia at which time he was found to have genu varum (bow leggedness) and microcephaly. He has had two deformity correction surgeries since that time, a hernia repair at 2 months, and cryptorchidism repair at 8 years of age. He has celiac disease, arachnodactly, microcephaly and severe mental retardation diagnosed by clinical observation. He has never suffered a seizure.

NG 339-1 (Mutation: G1280AfsX21)

The patient is a 10 year, 10 month old female who is the product of a consanguineous union. She presented to medical attention at 3 months of age due to failure to thrive and small head size. At the time of presentation her head circumference was 34.5 cm with obvious microcephaly. On neurologic examination, she had good head control. She recognized her mother and was noted to have a social smile. Her deep tendon reflexes (DTR's) were 3+ in all four extremities and she had increased muscle tone throughout. She has one healthy sibling. No current clinical information is available.

NG 537-1 (Mutation: E526K)

The patient is a 15 year, 5 month old female who is the product of consanguineous marriage. Peri- and neonatal periods were unremarkable except for meconium aspiration. She was delayed to acquire motor skills in the first three years of life but ultimately presented to medical attention at the age of 3.5 years due to poor verbal skills. Head circumference at this time was 43 cm, consistent with microcephaly. She was noted to have severe mental retardation, but the remainder of the neurologic exam at the time was normal. She was placed on anti-epileptic medication for a brief period of time during her childhood due to abnormal electroencephalograms (EEG's), however, she never suffered an overt seizure. The medication was discontinued. At her last clinic visit in 2009, her head circumference was 51 cm. On physical exam, she was noted to have microcephaly, prognathism, dysconjugate gaze, and dysarthria. She was able to ambulate independently, demonstrated full strength in all muscle groups, and had normal reflexes.

NG 891-1 (Mutation: V1402 GfsX12)

The patient is a 2 year 4 month old male who was born to consanguineous parents. He had a normal prenatal and neonatal period and was the product of an uneventful vaginal delivery. He presented to medical attention at 20 months of age due to relatively small head size compared to his healthy sibling. At the time of presentation, he was 9,500 gr (50-75th percentile) and 83 cm ($50^{th}$ percentile). His head circumference, however, was 41 cm (<3 percentile). He was noted on clinical exam to have developmental delay and severe psychomotor retardation but has not suffered from seizures.

The results of the experiments are now described.

It is demonstrated herein using whole-exome sequencing that recessive mutations in WD repeat domain 62 (WDR62) are the cause of a wide spectrum of severe cerebral cortical malformations including microcephaly, pachygria with cortical thickening as well as hypoplasia of the corpus callosum. Some patients with mutations in WDR62 had evidence of additional abnormalities including lissencephaly, schizencephaly, polymicrogyria and, in one instance, cerebellar hypoplasia, all traits traditionally regarded as distinct entities.

In mice and humans, WDR62 transcripts and protein are enriched in neural progenitors within the ventricular and subventricular zones. Expression of WDR62 in the neocortex is transient, spanning the period of embryonic neurogenesis. Unlike other known microcephaly genes, WDR62 does not apparently associate with centrosomes and is predominantly nuclear in localization, as demonstrated herein. These findings unify previously disparate aspects of cerebral cortical development and highlight the use of whole-exome sequencing to identify disease loci in settings in which traditional methods have proved challenging.

Whole-exome sequencing using next generation technology was applied to the index case of a small consanguineous kindred (NG 26) from eastern Turkey that presented for medical attention owing to failure to reach developmental milestones and was found on clinical examination to have microcephaly. Neuroimaging studies identified a complex array of developmental abnormalities including pachygria and thickened cortex (FIGS. 1a-d and 3c).

Figures 1A, 1B, 1C, 1D:
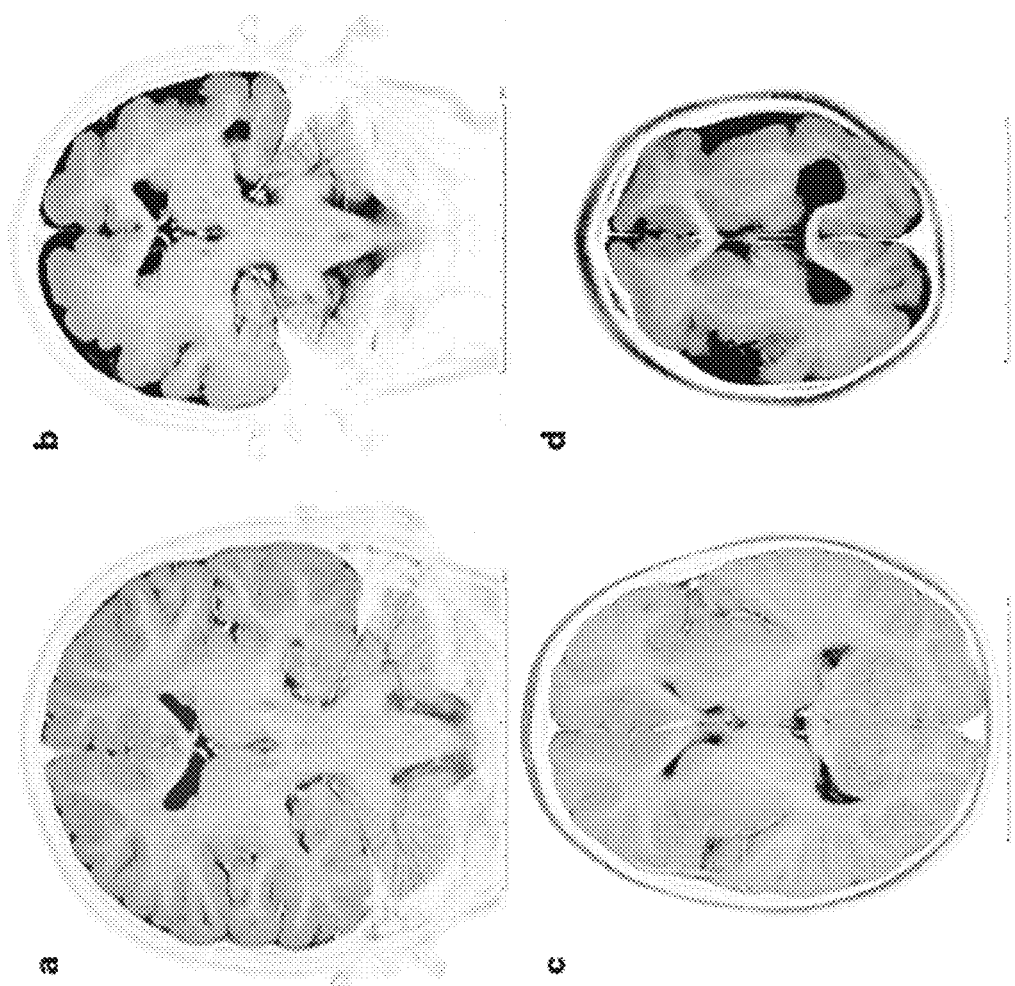
FIGS. 1A-1F, depicts the results of experiments identifying a 4-bp deletion in the WDR62 gene in a family with microcephaly and pachygria. a-d, Coronal (a) and axial (c) magnetic resonance images of a control subject compared with NG 26-1 (b, d) confirms the clinical diagnosis of microcephaly and shows a diffusely thickened cortex, an indistinct grey-white junction, pachgyria and underoperculization. All images are T2 weighted (photographically inverted). Scale bars, centimeters. e, A 4-bp deletion (red box) in the WDR62 is identified through exome sequencing (WT, wild type). f, Sanger sequencing confirms the deleted bases (in green). The altered amino-acid sequence (starting at position 1,402) leading to a premature stop-codon (X) is shown in red.
Figures 1E, 1F:
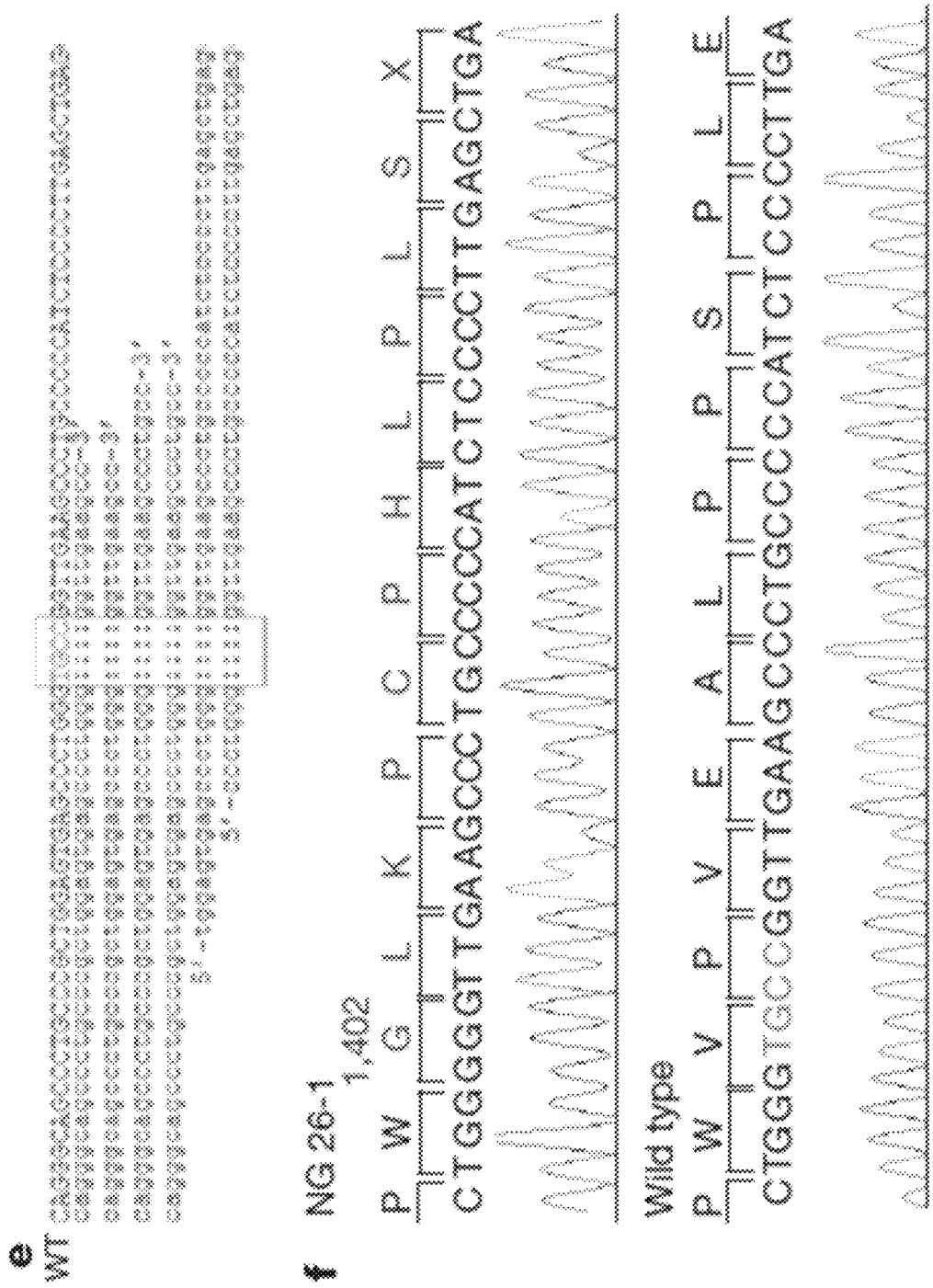
Figure 2:
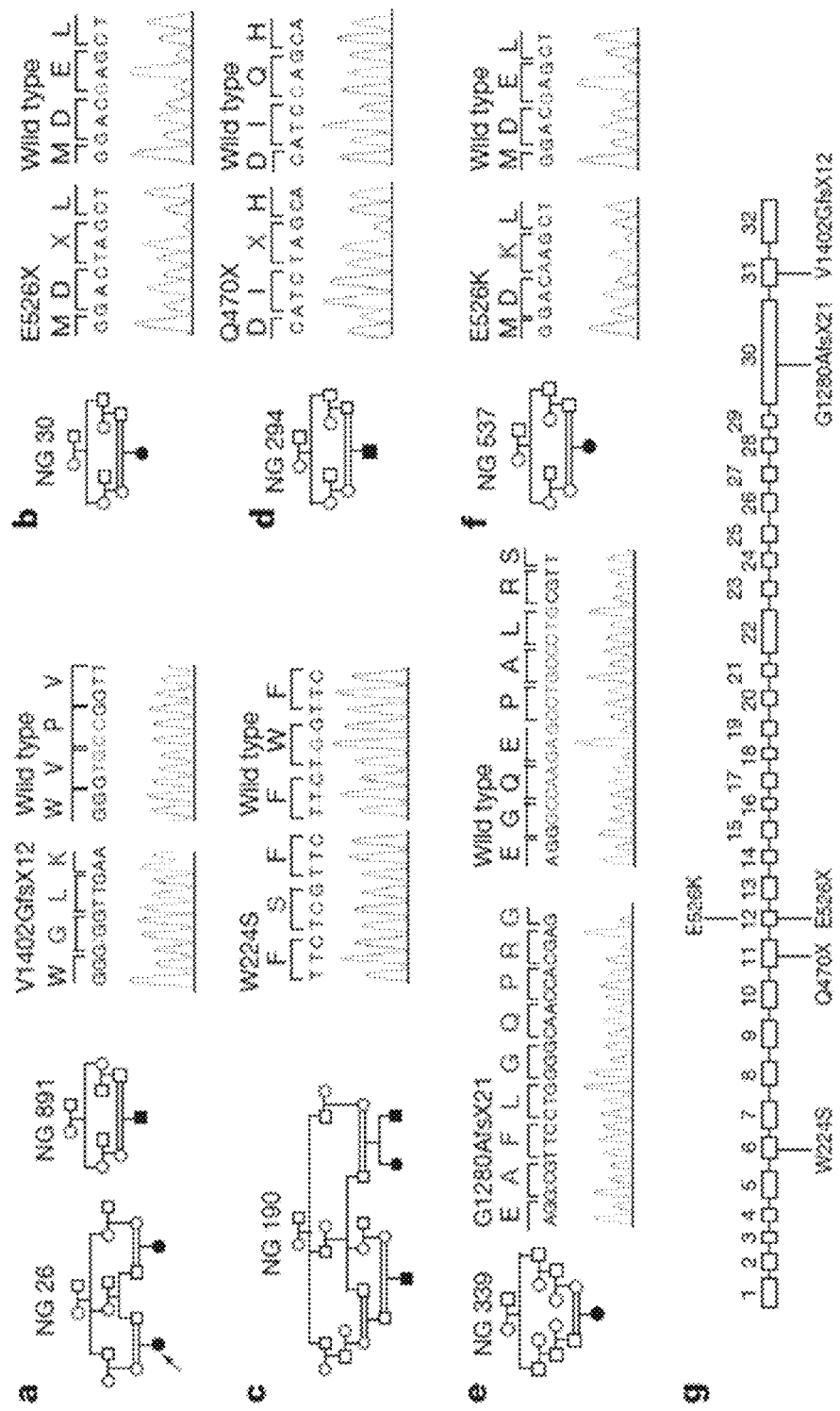
FIG. 2, comprising
Figure 5:
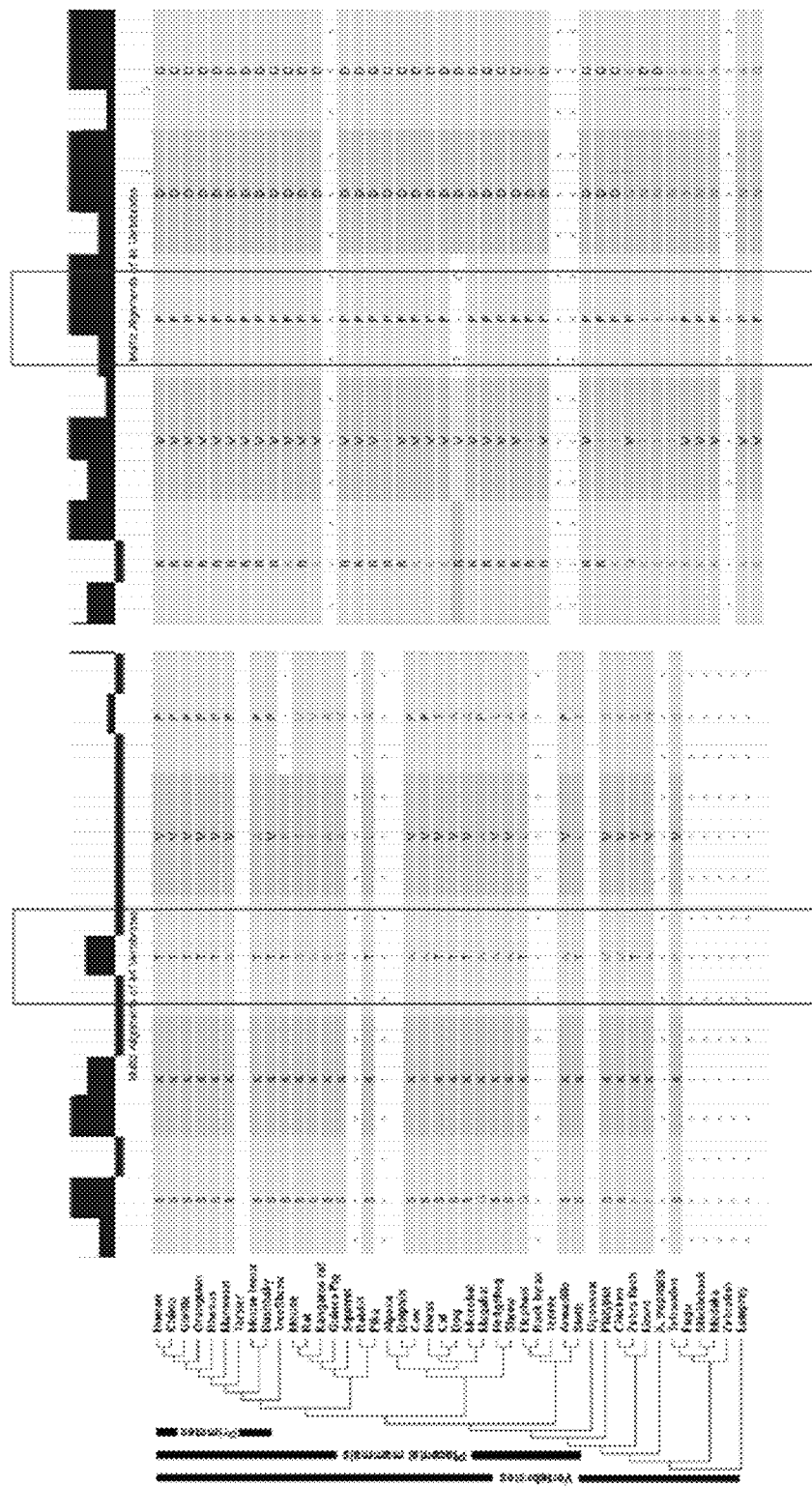
FIG. 5 depicts two novel homozygous missense variants identified within the shared homozygosity regions of affected subjects of family NG 26. Left panel: On chromosome 12, position 130,807,115, an A to G transition results in a Thr to Ala substitution in the non-conserved 565th residue (marked with the red box) of Splicing Factor, Arginine/Serine-rich 8 (SFRS8). Right panel: Similarly, in IBTK (Inhibitor of Bruton Agammaglobulinemia Tyrosine Kinase), a G to C substitution on chromosome 6, position 82,980,721, results in a Pro to Ala substitution of the 716th residue of the protein (red box) which is not highly conserved across 44 vertebrate species (from www.genome.uesc.edu: Kent W J, et al., Genome Res. 2002 June; 12(6):996-1006.)

Initially, whole-genome genotyping of the two affected members was performed to identify shared homozygous segments (each >2.5 centimorgans (cM)) that together composed 80.11 cM (Table 1). Given the substantial length of these shared segments, whole-exome sequencing of the index case was next performed using Nimblegen solid-phase arrays and the Illumina Genome Analyser IIx instrument (2009, Choi et al., Proc. Natl. Acad. Sci. USA 106:19096-19101). A mean coverage of 44× was achieved, and 94% of all targeted bases were read more than four times, sufficient to identify novel homozygous variants with high specificity (Table 2). Two novel homozygous missense variants and one novel homozygous frameshift mutation were identified within the shared homozygozity intervals (FIG. 5 and Table 3). The frameshift mutation occurred in WDR62, deleting four base pairs (bp) in exon 31 (FIG. 1e). The full-length WDR62 (NM_001083961) maps to chromosome 19q13.12 and encodes 1,523 amino acids. The identified mutation causes a frameshift in codon 1,402, resulting in a premature stop codon at position 1,413 (FIG. 10. The mutation was confirmed to be homozygous in both affected subjects and to be heterozygous in both parents using Sanger sequencing (FIG. 2a and FIG. 2). It was not observed in 1,290 Turkish control chromosomes.

TABLE 1

| Chromosome | Start | End | SNP Start | SNP End | Number of SNPs | Length (cM) | Length (Mb) |
|---|---|---|---|---|---|---|---|
| 1 | 240,862,637 | 247,177,330 | rs10926796 | rs6704311 | 623 | 10.90 | 6.31 |
| 6 | 82,149,868 | 87,794,412 | rs2120536 | rs7740936 | 510 | 2.96 | 5.64 |
| 12 | 125,564,137 | 132,288,869 | rs16920745 | rs7975069 | 907 | 20.79 | 6.72 |
| 19 | 8,931,837 | 14,582,019 | rs2547067 | rs6511944 | 510 | 9.16 | 5.65 |
| 19 | 36,896,151 | 47,035,366 | rs10417470 | rs3922888 | 894 | 13.17 | 10.14 |
| X | 147,386,161 | 154,582,606 | rs5980537 | rs557132 | 478 | 23.13 | 7.20 |
| Total | | | | | 3,922 | 80.11 | 41.66 |

TABLE 2

| Read Length | Number of lanes | Read Type | Number of Reads | Reads Mapped to the Genome | Reads Mapped to the Exome | Average Coverage Across The Exome | Bases Covered $\geq$ 4X within the Exome |
|---|---|---|---|---|---|---|---|
| 74 | 2 | Single end | 37.1M | 97.3% | 57.40% | 44.3X | 94.34% |

*In two lanes of single-end 74 base pair reads, we obtained 37 million reads, 21 million of which mapped to the exome, and 466,000 of which mapped to the 969,174 exomic base pairs (out of 41.66 million genomic base pairs) in shared regions of homozygosity between the two affected siblings (Supplementary Table 1). The sequence error rate (per base per read)was 0.34%. Sensitivity and specificity for detection of homozygous variation from the reference sequence was high (both >97%) as determined by comparison of the sequencing data to the results of SNP genotyping as a reference.

TABLE 3

| Chr | Position | Base change | Quality Score | Coverage | Major allele (no PCR duplicates) | Minor allele (no PCR duplicates) | Gene | Status | Amino add change | Amino add position |
|---|---|---|---|---|---|---|---|---|---|---|
| 6 | 82,980,721 | G to C | 228 | 43 | 11 | 5 | I8TK | Missense | P716A | 716/1353 |
| 12 | 130,807,115 | A to G | 96 | 20 | 7 | 0 | SFRS8 | Missense | T565A | 565/951 |
| 19 | 41,287,310 | -TGCC deletion | 163/391 | 6 | 4 | 0 | WDR62 | frame-shift | V1402GfsX12 | 1402/1523 |

Figures 6A, 6B, 6C, 6D:
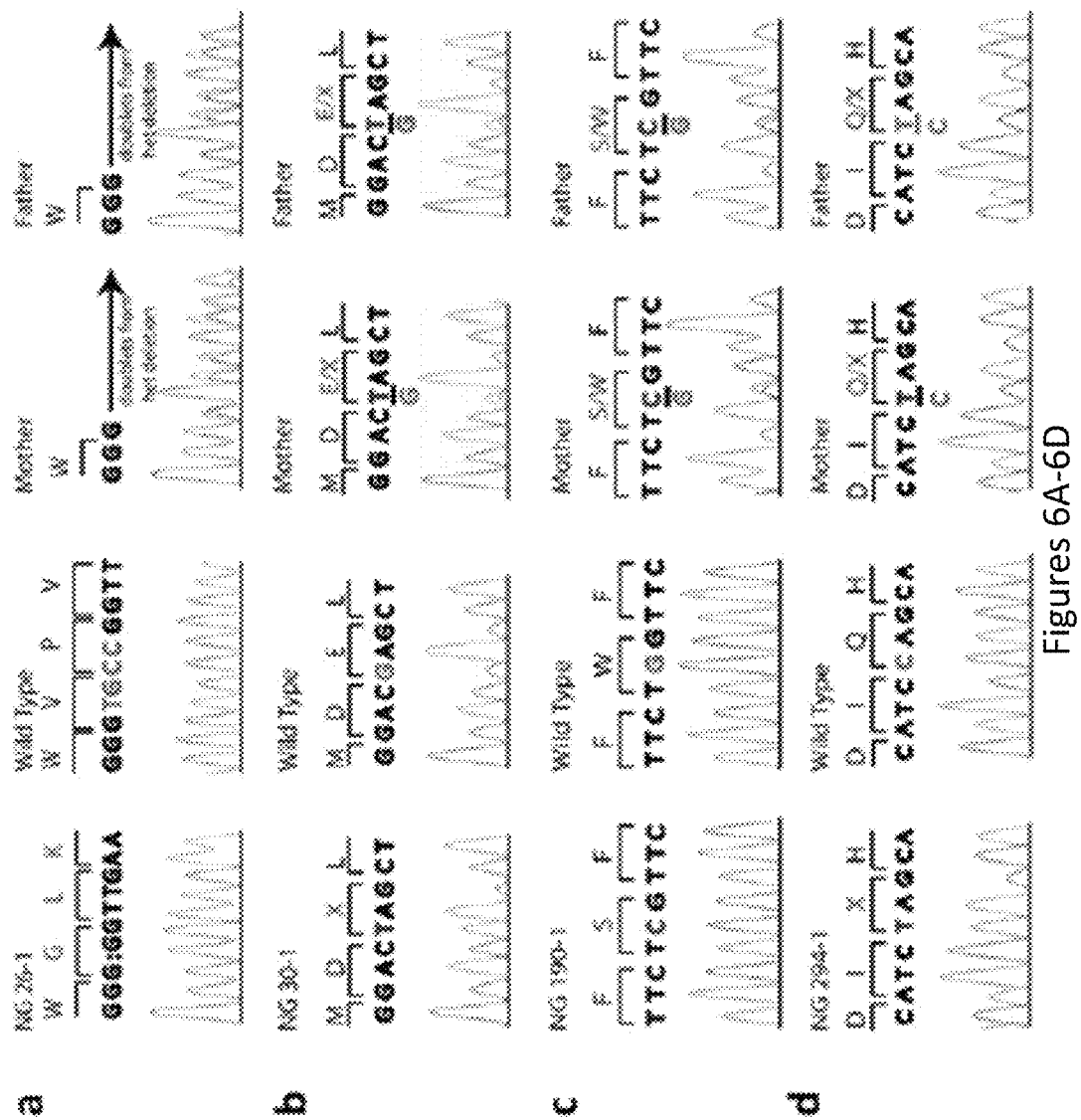
FIG. 6 depicts sequence traces of 7 families with WDR62 mutations. From left to right, the panels show the DNA sequences of the patients, control subjects, and the patients' parents, respectively. The predicted amino acids corresponding to each codon are represented above the nucleotide sequences, which are marked in bold letters above the chromatograms. For each sequence, the mutated base(s) are shown in red, as are resultant amino acid substitutions. For the wild type sequences, the altered bases are shown in green. Note that all patients are homozygous for the mutations while both parents are heterozygous. The following mutations are observed: (a) NG 26: V1402 GfsX12, (b) NG 30: E526X, (c) NG 190: W224S, (d) NG 294: Q470X, (e) NG 339: G1280AfsX21, (0 NG 537: E526K, (g) NG 891: V1402 GfsX12.
Figures 6E, 6F, 6G:
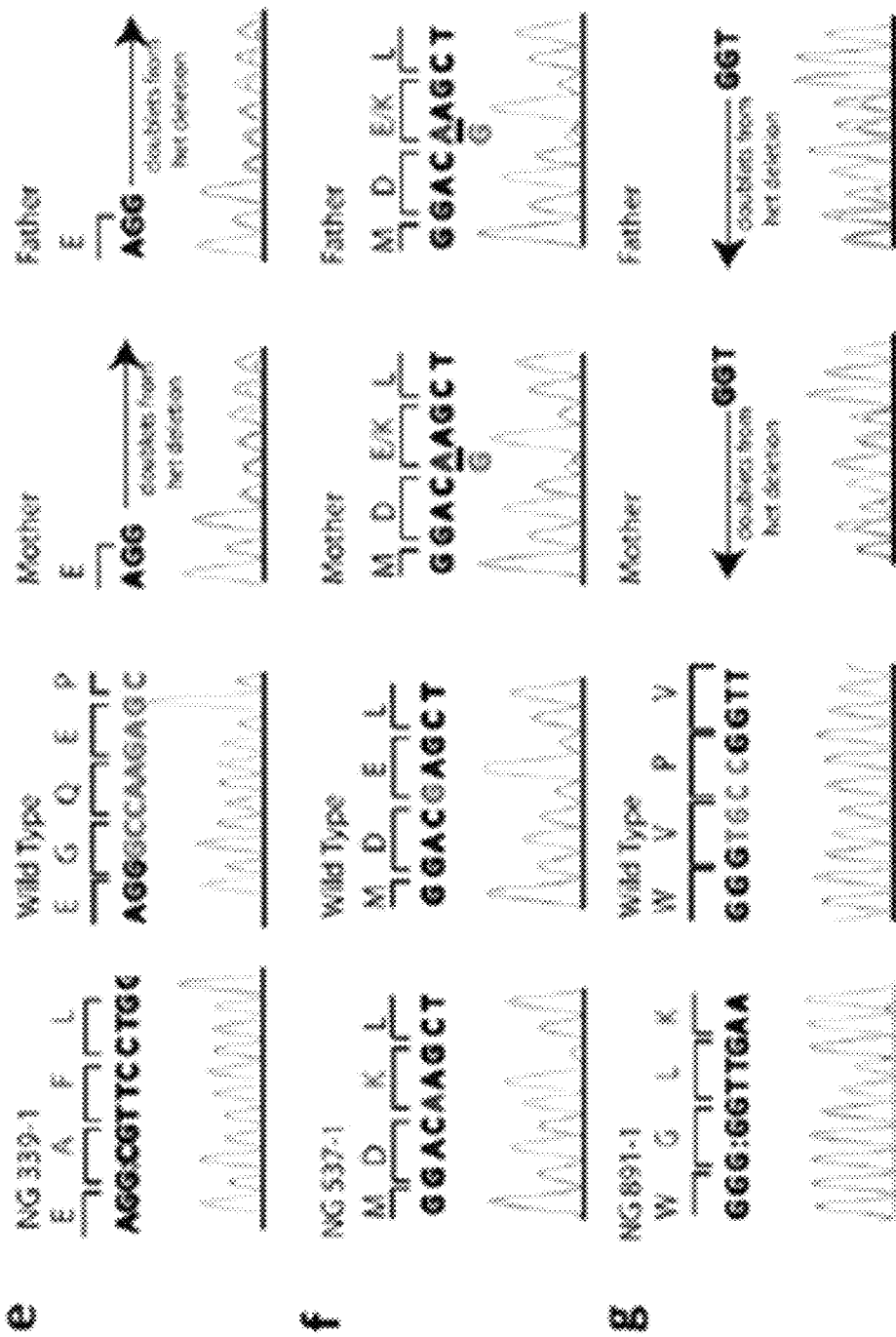

Because this homozygous mutation in WDR62 was particularly compelling, it was investigated whether mutations in this gene might account for additional cases of malformations of cortical development. As the index case was ascertained with an initial diagnosis of pachygyria, a group of 30 probands who carried diagnoses of agyria or pachygyria and were products of consanguineous unions (inbreeding coefficient >1.5% (2007, Purcell et at, Am. J. Hum. Genet. 81:559-575)), were focused on. Among these patients, whole-genome genotyping identified eight with homozygosity of at least 2 cM spanning the WDR62 locus. One of these affected subjects, NG 891-1, was found to have the identical homozygous haplotype spanning the WDR62 locus and had the same 4-bp deletion (FIG. 2a and FIG. 6). Although there was no known relatedness between the two pedigrees, the kinship coefficient of NG 891-1 with NG 26-1 and NG 26-4 was 2.47% and 3.72%, consistent with fourth-degree relatedness (for example, first cousins once removed).

Figure 7:
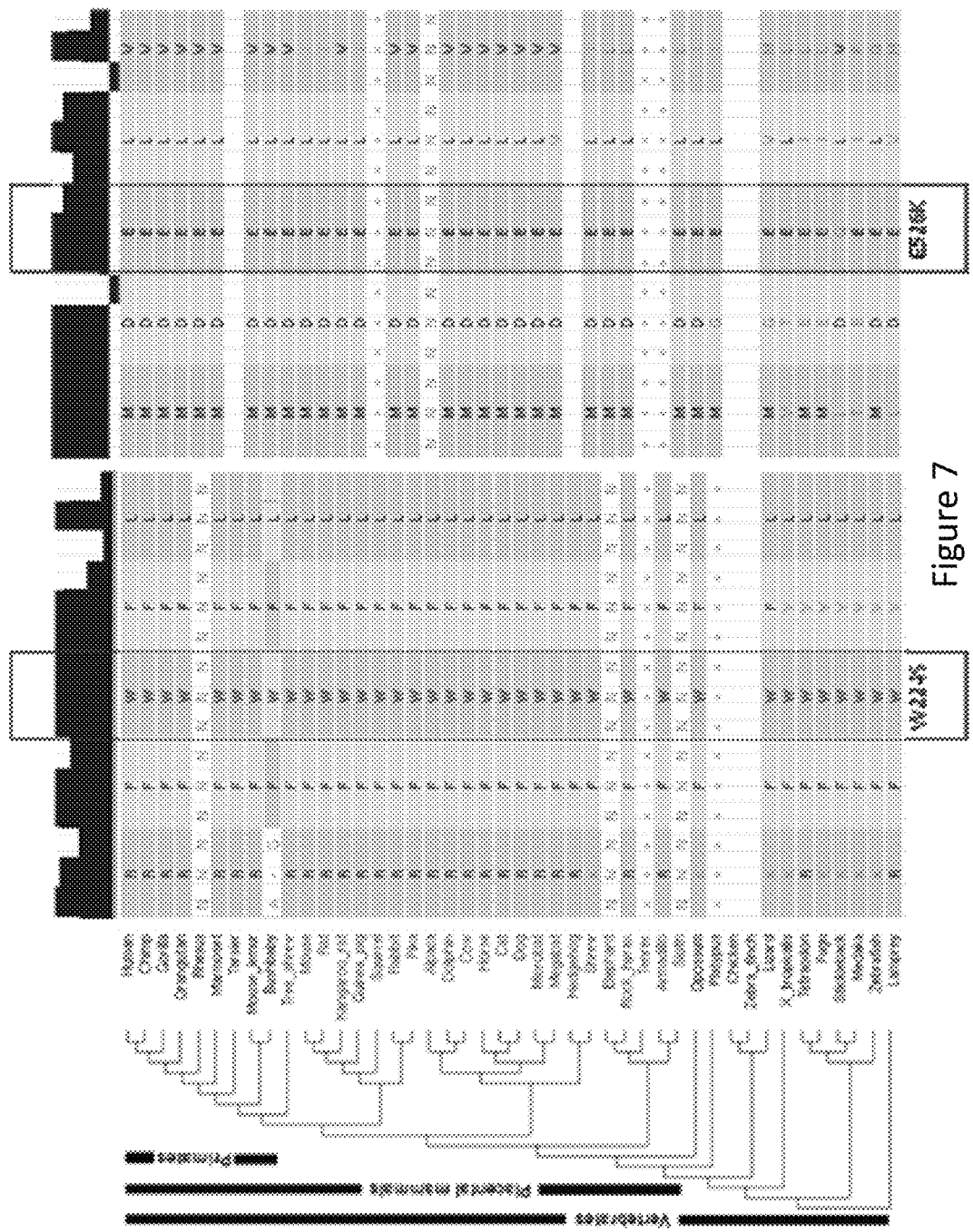
FIG. 7 depicts a sequence alignment of vertebrate WDR62 proteins. Missense mutations identified in NG 190 (W224S) and NG 537 (E526K) alter two highly conserved amino acid residues across 44 vertebrates (with the exception of Stickleback for position 526) (see www.genome.ucsc.edu; Kent, et al., 2002 June; 12(6):996-1006).
Figure 8:
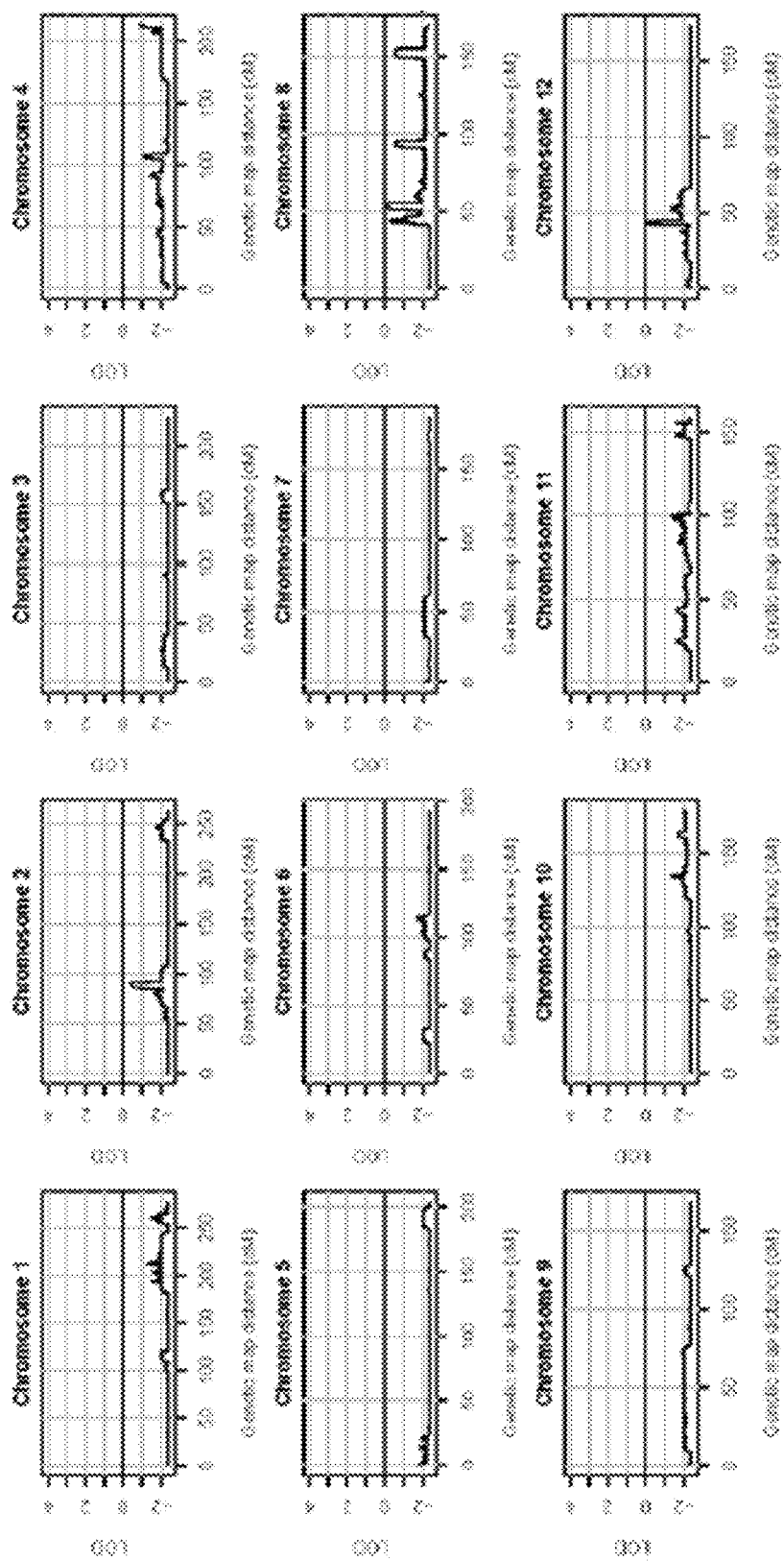
FIG. 8 depicts genome-wide linkage analysis of pedigree NG 190 with three affected and one unaffected family members. For linkage analysis, an autosomal recessive mode of inheritance with a phenocopy rate of 0.001, penetrance rates of 0.001 and 0.99 for heterozygous and homozygous conditions, respectively, were assumed. Disease causing allele frequency was set to 0.001. The vertical axis corresponds to LOD score and the horizontal axis shows genetic distance in centimorgans (cM). The linkage graphs for all autosomal chromosomes are shown. The maximum LOD score for the chromosome 19 locus spanning the WDR62 gene, located between 41,237,623 and 41,287,852 base pairs is 3.64. The LOD-3 interval is marked by markers rs3855681 and rs7359950, located at 16,259,314 (40.1 cM) and 44,455,605 (63.8 cM) base pairs, respectively.
Figure 8:
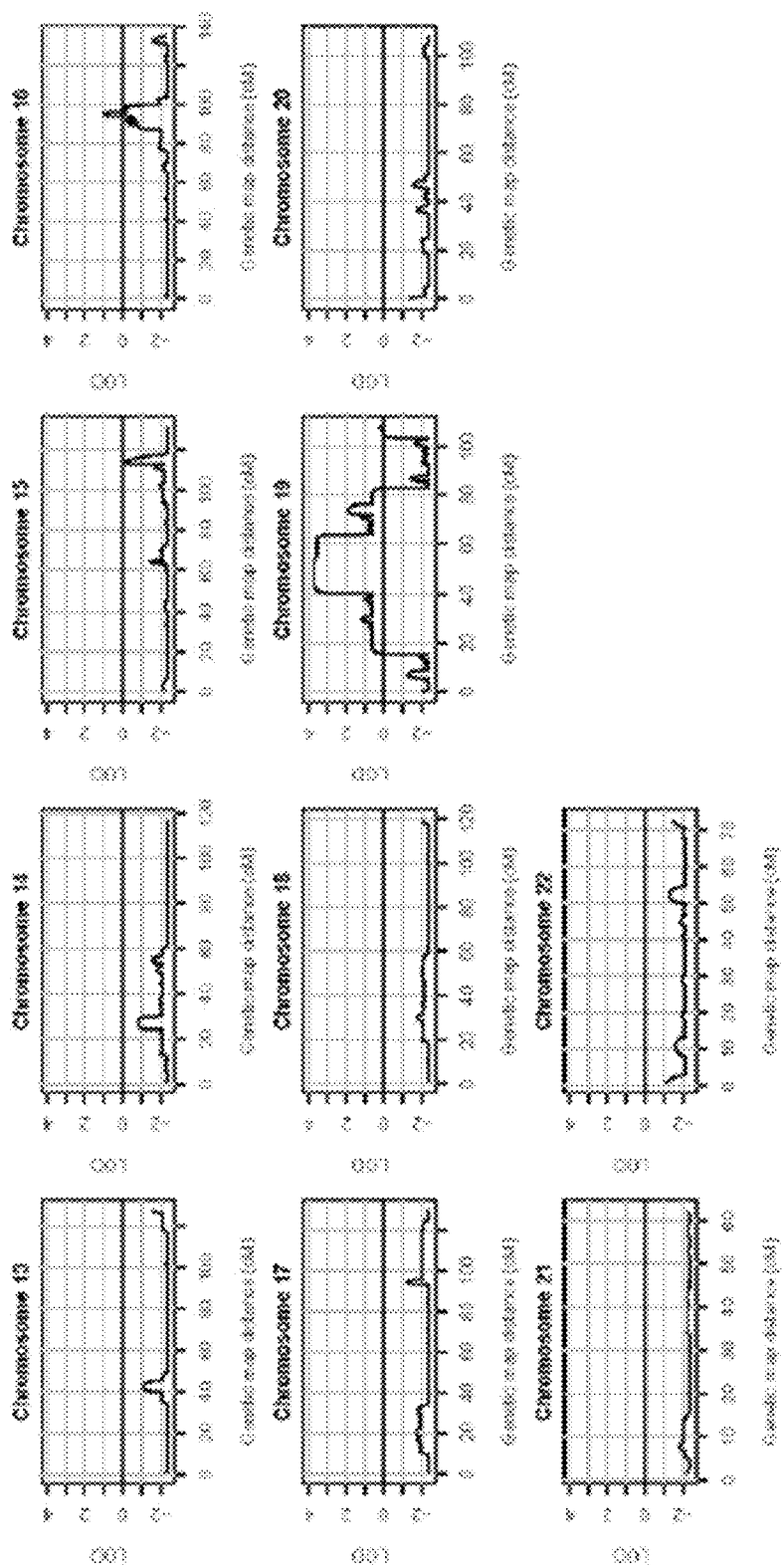

Further Sanger sequencing of the complete coding region of WDR62 in the seven remaining kindreds revealed five additional novel homozygous mutations (FIG. 2b-f). The affected member of kindreds NG 30 and NG 294 had homozygous nonsense mutations at codons 526 (E526X) and 470 (Q470X), respectively (FIGS. 2b, d); subject NG 339-1 had a homozygous 17-bp deletion leading to a frameshift at codon 1,280 that resulted in a premature termination codon following a novel peptide of 20 amino acids (FIG. 2e); subjects NG 190-1 and NG 537-1 respectively had novel homozygous missense variants W224S and E526K (FIGS. 2c, f), which occurred at positions highly conserved among vertebrates and were predicted to be deleterious by the Polyphen algorithm (FIG. 7). Moreover, after identification of the W224S mutation in NG 190, two additional relatives affected with microcephaly and mental retardation (kinship coefficients of 7.47% and 5.81%), both of whom also proved to be homozygous for the same mutation, were ascertained. The resulting lod score for linkage to the trait within the expanded kindred was 3.64; the chromosome segment containing WDR62 was the sole homozygous region shared among all three affected subjects (FIG. 12).

All of the newly identified mutations, except E526K, were absent from 1,290 Turkish and 1,500 caucasian control chromosomes. The heterozygous E526K variant was detected in three apparently unrelated Turkish subjects who were neurologically normal (allele frequency 0.2%). As an additional control measure in the evaluation of these homozygous mutations, the coding region of the gene in 12 consanguineous patients with non-neurological conditions who were found to have segments of homozygosity of at least one million base pairs spanning WDR62 was sequenced. None of these 12 subjects were found to have protein coding changes in WDR62. Similarly, only four heterozygous novel missense variants in WDR62 in the sequence of 100 whole exomes of subjects with non-neurological diseases were identified (Table 4). Public databases (dbSNP) showed no validated nonsense or frameshift alleles at this locus. Finally, no copy number variants overlapping the coding regions of WDR62 in the own set of 11,320 whole-genome genotypes were observed and only one deletion identified by bacterial artificial chromosome (BAC) array is reported in the Database of Genomic Variants (projects.tcag.ca/variation/).

TABLE 4

| Sample ID | Chr | Position | Base Change | Amino Acid Change | Amino Acid Location |
|---|---|---|---|---|---|
| RKH005 | chr19 | 41,284,406 | A > T | D991V | 991/1523 |
| PTH120 | chr19 | 41,285,904 | G > A | A1152T | 1157/1523 |
| PTH108 | chr19 | 41,284,409 | C > T | S992L | 992/1523 |
| LMB06 | chr19 | 41,285,506 | T > C | V1083A | 1083/1523 |

Figure 3:
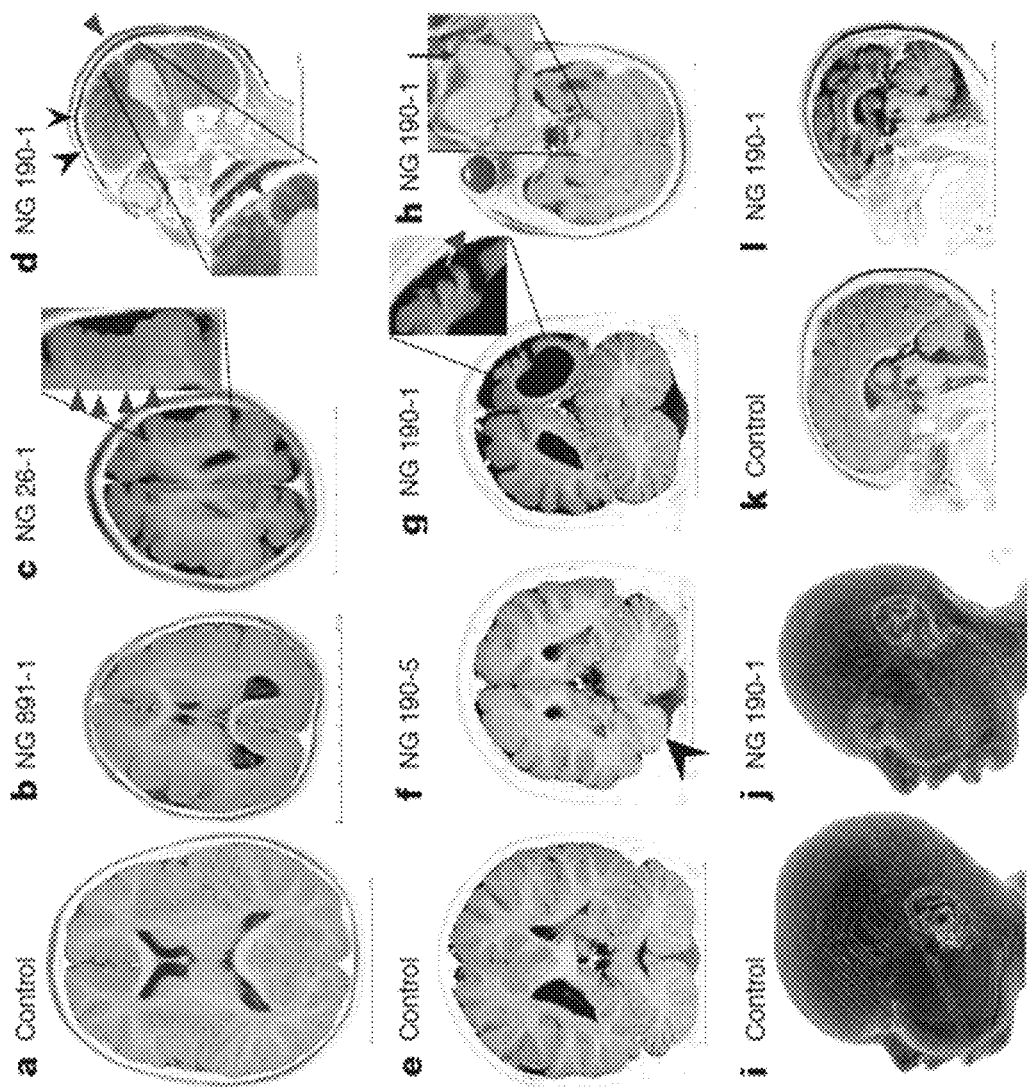
FIG. 3, comprising

All of the index cases with WDR62 mutations presented for medical attention with mental retardation and were found to have prominent microcephaly on physical examination; some also suffered from seizures. Re-examination of the high field strength (3 T) magnetic resonance imaging (MRI) scans of the affected subjects by independent neuroradiologists who were blind to previous diagnoses identified hallmarks of a wide range of severe cortical malformations (summarized in Table 5. All nine patients had extreme microcephaly, pachygyria and hypoplasia of the corpus callosum (FIG. 3). in addition, they demonstrated radiographic features consistent with lissencephaly, including varying degrees of cortical thickening and loss of grey-white junction (FIG. 3). Under-opercularization (shallow Sylvian fissures) (FIG. 1b) was observed in six affected subjects. Two of the subjects had striking polymicrogyria that predominantly affected one hemisphere (FIGS. 3c, d, g); in one this was associated with a unilateral open-lip schizencephaly characterized by a cleft surrounded by grey matter that extended into the ventricle (FIGS. 3d, g). Other malformations observed included hippocampal dysmorphology with vertical orientation in six cases and a single case of unilateral dysgenesis of the cerebellum (FIG. 3f). There were no abnormalities of the brainstem, with the exception of unilateral atrophy observed in one patient, most likely secondary to Wallerian degeneration from the severe cerebral abnormalities observed (FIG. 3h).

TABLE 5

| Patient ID | Cortical Thinkening | Microcephaly | Pachygyria | Polymicrogryria | Schizencephaly | Under-opercularization | Cerebellum | Hippocampus | Corpus Callosum Rostrum | Corpus Callosum Splenium |
|---|---|---|---|---|---|---|---|---|---|---|
| NG 26-1 | + | + | + | R temporal and RL occipito-parietal | − | + | Normal | Normal | Mild hypoplasia | Mild hypoplasia |
| NG 30-1 | + | + | + | − | − | − | Normal | Dysmorphic | Absent | Moderate Hypoplasia |
| NG 190-1 | + | + | + | L fron-temporal-parietal | L parietal | + | Normal | Dysmorphic | Absent | Marked Hypoplasia |

TABLE 5-continued

| Patient ID | Cortical Thinkening | Micro-cephaly | Pachy-gyria | Polymicro-gryria | Schizen-cephaly | Under-opercularization | Cerebellum | Hippo-campus | Corpus Callosum Rostrum | Corpus Callosum Splenium |
|---|---|---|---|---|---|---|---|---|---|---|
| NG 190-5 | + | + | + | − | − | − | Rhypoplasla | Dysmorphic | Absent | Marked Hypoplasia |
| NG 190-6 | + | + | + | − | − | − | Normal | Dysmorphic | Mild hypoplasia | Normal |
| NG 294-1 | + | + | + | − | − | + | Normal | Dysmorphic | Mild hypoplasia | Marked Hypoplasia |
| NG 339-1 | + | + | + | − | − | + | Normal | Dysmorphic | Absent | Marked Hypoplasia |
| NG 531-1 | + | + | + | − | − | + | Normal | Normal | Mild hypoplasia | Normal |
| NG 891-1 | + | + | + | − | − | + | Normal | Normal | Mild hypoplasia | Moderate Hypoplasia |

R: right,
L: left

Figure 9:
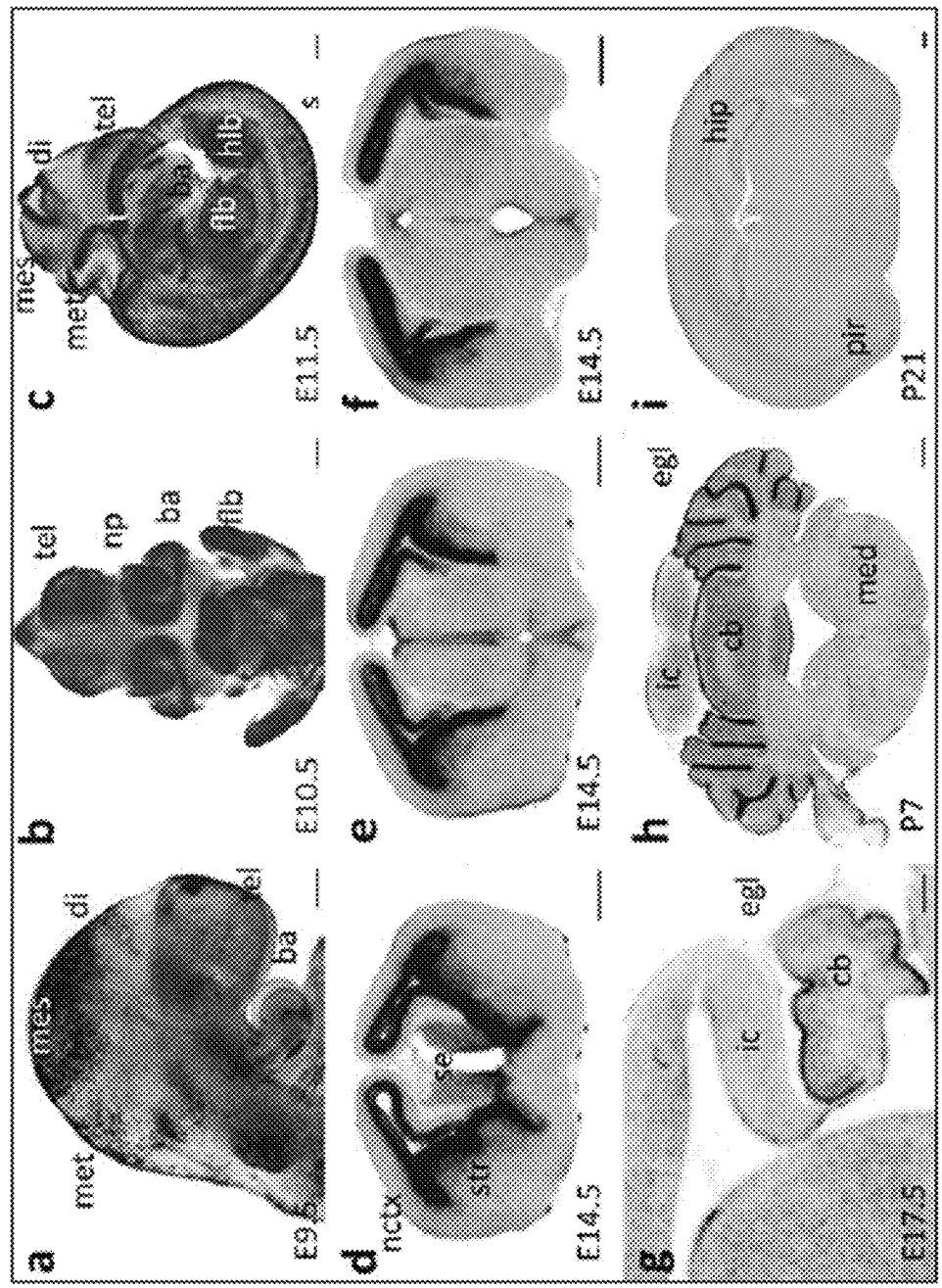
FIG. 9, comprising

Given the wide range of cortical malformations associated with WDR62 mutations, its expression in the developing mouse brain was investigated. Notably, during early development, in wholemount embryos from embryonic day (E) 9.5 to E11.5, Wdr62 expression is prominent in neural crest lineages (FIGS. 9a-c). Wdr62 also shows striking expression in the ventricular and subventricular zones during the period of cerebral cortical neurogenesis (E11.5-16.5), with expression decreasing in intensity by E17.5 (FIG. 4a, FIGS. 9d-f). In the cerebellum, Wdr62 is strongly expressed in precursors of granule neurons at late embryonic and early postnatal stages; by postnatal day 9 (P9) Wdr62 expression is dramatically reduced (FIGS. 9g, h). By postnatal day 21 (P21), low levels of Wdr62 expression are detected only in the hippocampus and the piriform cortex, and transcription is absent among differentiated cortical neurons (FIG. 9i).

Figure 4:
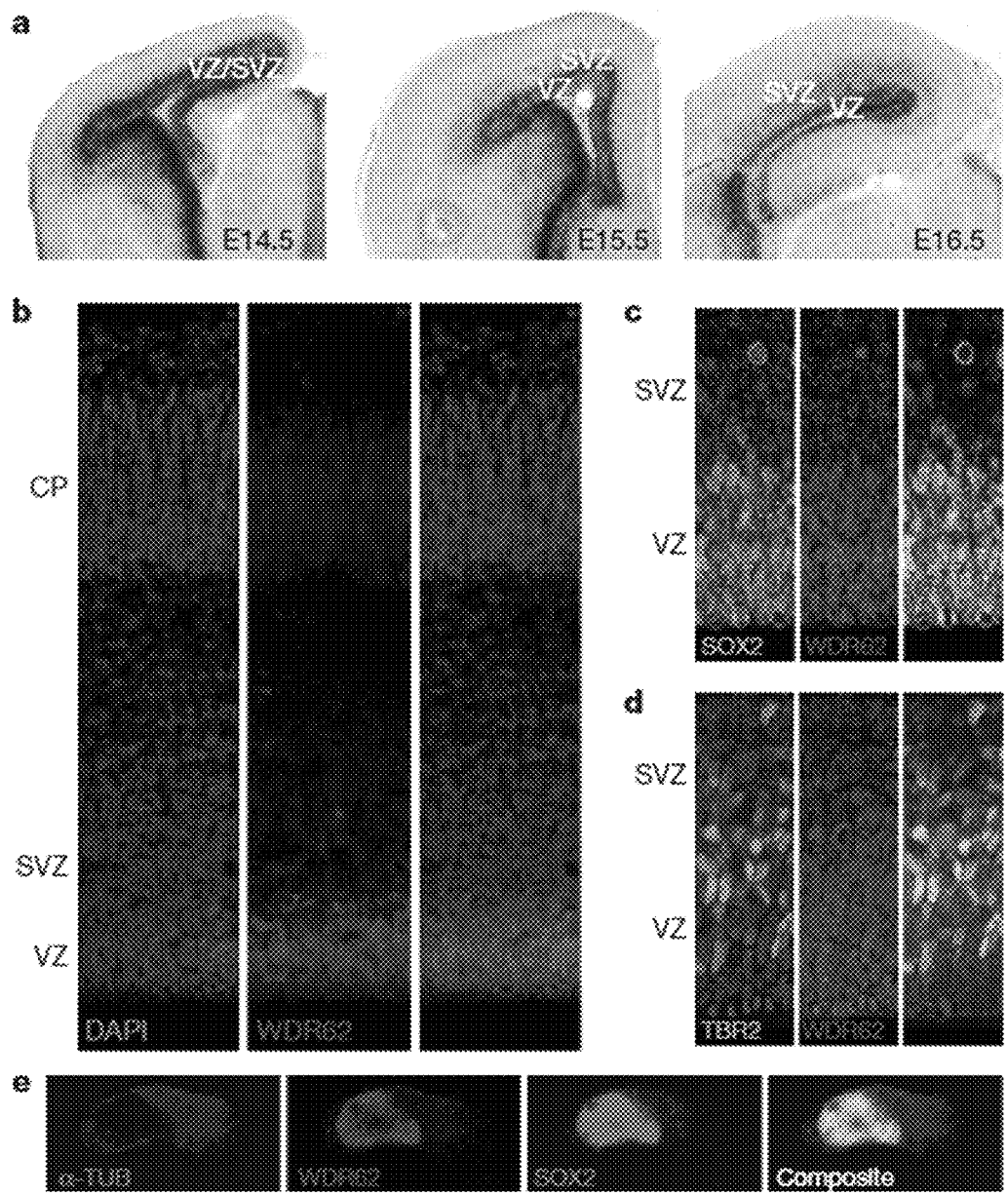
FIG. 4, comprising
Figure 10:
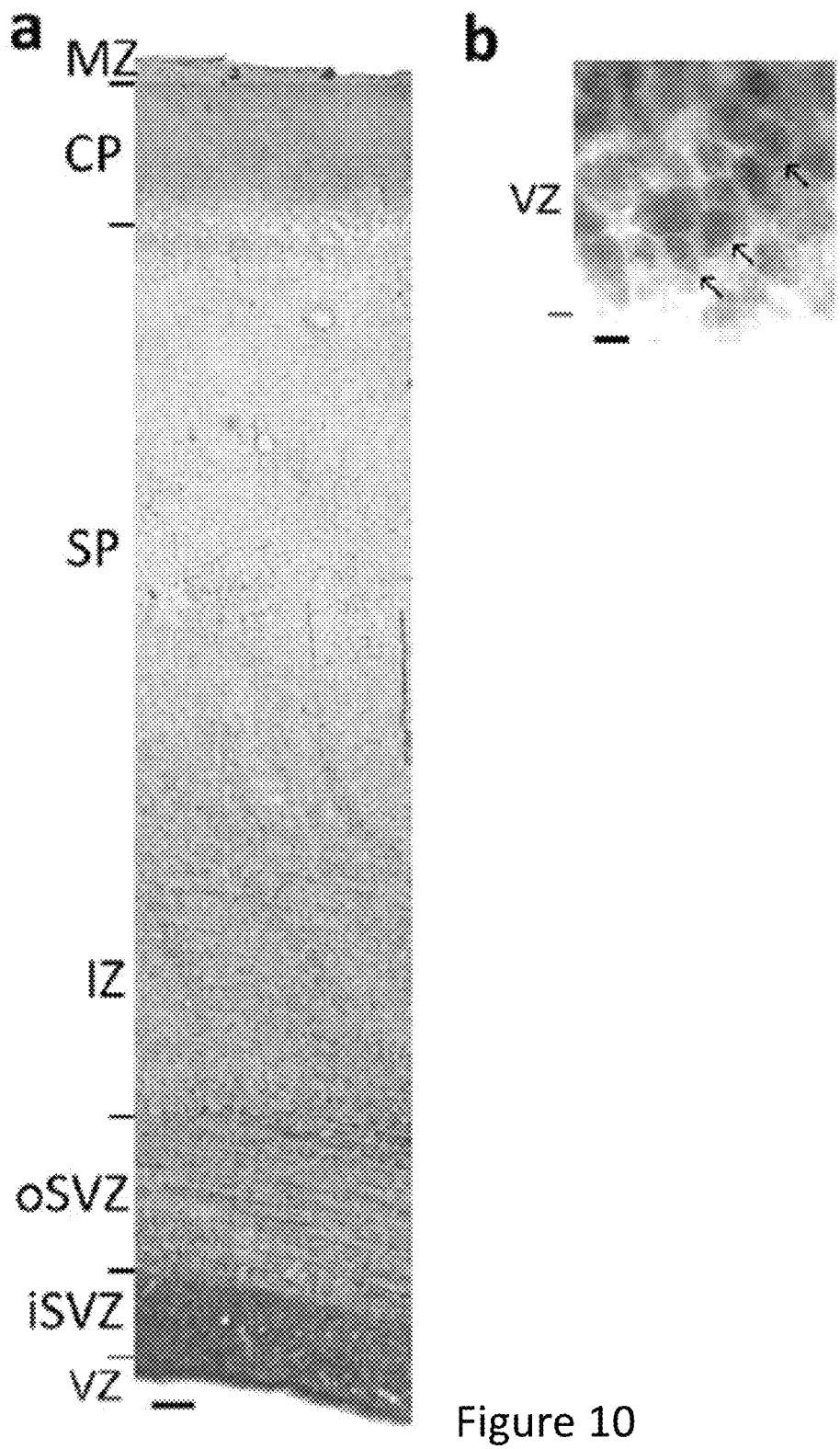
FIG. 10, comprising
Figure 11A:
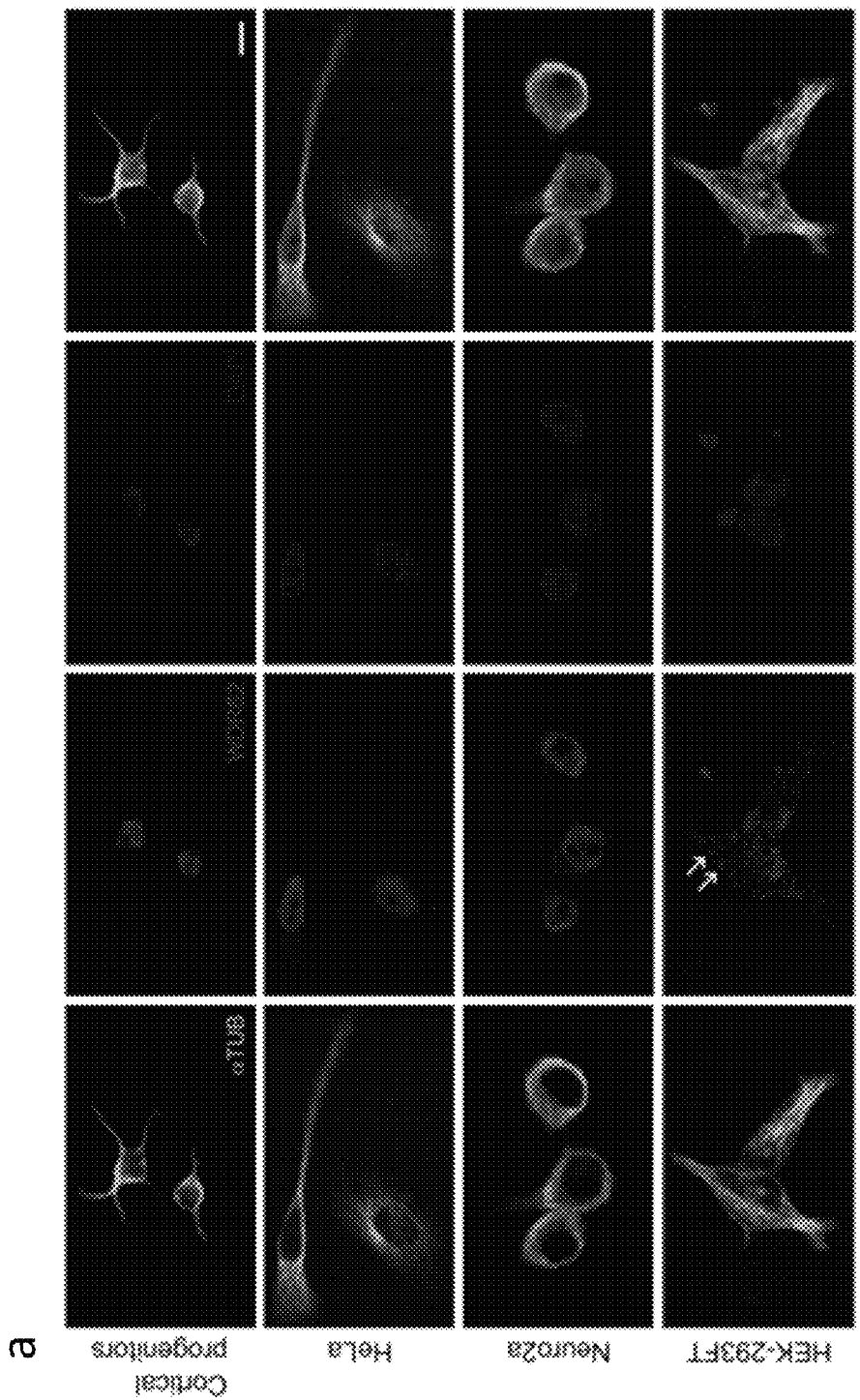
FIGS. 11a-11b, depicts the results of experiments assessing localization. Immunofluorescent staining for α-tubulin (green), WDR62 (red, using mouse anti-WDR62 (Sigma-Aldrich) antibody), and counterstaining by DAPI (blue) in cultured E12.5 mouse cortical neural progenitors, HeLa, Neuro2a, and HEK-293FT cells. WDR62 localization is nuclear in cortical neural progenitors, HeLa, and Neuro2a cells. In HEK-293FT cells, WDR62 is localized to granules (arrows) as previously described by Wasserman et al, 2010 (Mol Bio Cell, 21:117-
Figure 11B:
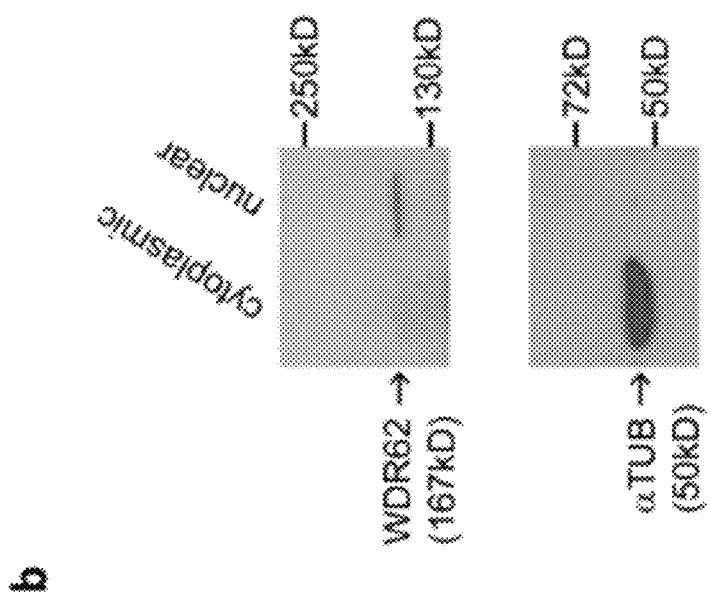

Next, WDR62 protein expression was examined using a previously characterized antibody (2010, Wasserman et al., Mol. Biol. Cell 21:117-130) (FIGS. 4b-d). Both in the mouse and human fetal brain, WDR62 was enriched within the ventricular and subventricular zones, consistent with the in situ hybridization findings (FIG. 4 and FIG. 10). These stainings suggested that WDR62 localizes predominantly to the nucleus in neuronal cells, which was confirmed by immunofluorescence microscopy using cell cultures and western blotting with subcellular fractionation of cortical embryonic mouse cells with a second antibody (FIG. 4e and FIG. 11). Genes previously implicated in microcephaly encode centrosomal proteins (2005, Bond et al., Nature Genet. 37:353-355; 2009, Kumar et al., Am. J. Hum. Genet. 84:286-290; 2009, Thornton et al., Trends Genet. 25:501-510); thus it is noteworthy that WDR62 is apparently not associated with the centrosome during mitosis (FIG. 12).

The findings described herein implicate WDR62 in the pathogenesis of a spectrum of cortical abnormalities that until now have largely been conceptualized to be distinct (2008, Guerrini et al., Trends Neurosci. 31:154-162; 2001, Barkovich et al., Neurology 57:2168-2178; 2005, Barkovich et al., Neurology 65:1873-1887), suggesting that these diverse features can have unified underlying causation. It is noteworthy that WDR62 lies in a 10-million-bp interval that had previously been identified as a microcephaly locus, MCPH2 (1999, Roberts et al., Eur. J. Hum. Genet. 7:815-820). Although there were no imaging studies presented in the previous mapping of this locus, the findings described herein suggest that WDR62 is the MCPH2 gene and extend the phenotype beyond microcephaly.

To seek further insight into the biological function of WDR62, the expression data of early embryonic development of mouse brain (GSE8091) (2008, Hard et al., 8:1257-1265) for genes with expression profiles significantly correlated with that of WDR62 was examined (Bonferroni corrected $P<0.01$, $n=1,104$). Functional annotation suggested that positively correlated genes were enriched for those encoding nuclear proteins (Benjamini adjusted $P=6.23\times10^{-30}$), RNA processing proteins (Benjamini adjusted $P=1.90\times10^{-31}$) and cell-cycle proteins (Benjamini adjusted $P=3.25\times10^{-18}$). Negatively correlated genes encoded neuronal differentiation proteins (Benjamini adjusted $P=1.40\times10^{-7}$). Several genes linked to developmental brain malformations, such as DCX, DCC and BURB1B, were found in these enrichment sets (Table 6).

TABLE 6

| Symbol | Wdr62 correlation | P value | Malformation | References |
|---|---|---|---|---|
| Dcx | −0.95 | 3.00E−08 | X-linked lissencephaly-1; Double Cortex Syndrome | Cell 92: 51-61,1998, Cell 92: 63-72, 1998 |
| Tubo1a | −0.94 | 5.80E−08 | Lissencephaly type 3 | Cell 128: 45-57, 2007; Hum. Mutat. 28: 1055-1064, 2007 |
| Dcc | −0.94 | 9.71E−08 | Congenital Mirror Movements (Bimanual Synergia) | Science 328: 592-only, 2010 |
| Bub1b | 0.93 | 1.18E−07 | Mosaic Variegated Aneuploidy Syndrome (MVA), microcephaly | Am. J. Med. Genet. 140A: 358-367, 2006 |
| Cc2d2a | 0.94 | 5.47E−08 | Joubert Syndrome 9; Type 6 Meckel Syndrome | Am. J. Hum. Genet. 82: 1011-1018, 2008; Am. J. Hum. Genet 82: 1361-1367, 2008 |
| Col18o1 | 0.95 | 2.36E−08 | Type 1 Knobloch Syndrome | Hum. Molec. Genet. 9: 2051-2058, 2000; Hum. Mutat. 23: 77-84, 2004 |

The results disclosed herein demonstrate that Whole-exome sequencing is particularly valuable for gene discovery in those conditions in which mapping has been confounded by locus heterogeneity and uncertainty about the boundaries of diagnostic classification, pointing to a bright future for its broad application to medicine.

Sequences

```
Homo sapiens WD repeat domain 62 (WDR62) nucleotide sequence,
NCBI Reference Sequence: NM_001083961
                                                          (SEQ ID NO: 1)
     tttcccgcgg ctgttcgctg ttccagtggg tcgtggcggt ggcggcagcg gcggttaggg    60
     gatgtaacgg tcgcccgcct ccggcgtgac gatggcggcc gtagggtccg gaggctatgc   120
     gcggaacgat gcaggggaga agctgccctc tgtcatggcg ggagttccgg cgcggagggg   180
     ccagtcctcc ccgccccccg ccccaccaat ctgcctacgg cggcggacgc gactctcgac   240
     ggcctccgag gagacggtgc agaaccgggt gtcactcgag aaggtgcttg gcatcacagc   300
     ccagaacagc agtggcctaa cctgtgaccc cggcacaggc catgtggcct acctggcagg   360
     ctgtgtggtg gtgattttgg accccaagga gaacaagcag cagcacatct ttaacaccgc   420
     caggaagtct ctcagtgctc tggccttctc ccctgatggg aagtacatag tgacagggga   480
     gaatgggcat aggcctgctg tgcgcatctg ggatgtggag gagaagaatc aggtggcgga   540
     gatgctaggc cacaagtatg gtgtggcgtg tgtggccttc tcacccaata tgaagcacat   600
     cgtgtccatg ggctaccaac atgacatggt gctcaacgtc tgggactgga agaaagacat   660
     cgtagtggcc tccaacaagg tatcttgtag agtcattgcc ctctccttct cagaggacag   720
     cagctatttt gtcactgttg ggaaccgcca tgtgaggttc tggttcttgg aagtctccac   780
     tgagacaaag gtgacgagca cagtgcccct tgtagggcgc tcgggcatcc tgggcgagct   840
     gcacaacaac atcttctgtg gtgtggcctg cggtcggggc cggatggcgg cagtaccttt   900
     ctgtgtgtcc tactcgggcc tcctctgcca gttcaatgag aagagggtgc tggagaagtg   960
     gatcaacctg aaggtctccc tgtcttcctg cctctgtgtc agccaggagc tcatcttctg  1020
     tggctgcaca gatgggatag tccgcatctt ccaggcccat agcctgcact acctcgcaa  1080
     cctgcccaag ccacactacc ttggggtaga cgtggcacag ggcctggagc ccagcttcct  1140
     cttccacagg aaggcggaag cagtccaccc agatacagtg gcactgacct tcgaccccat  1200
     ccaccagtgg ctgtcctgcg tgtataagga ccacagcatc tacatctggg atgtcaagga  1260
     catcaacaga gtgggcaagg tgtggtcaga gctcttccac agctcctacg tttggaacgt  1320
     ggaggtgtat cctgagtttg aagaccagag agcttgtttg ccatcaggat cctttctgac  1380
     ttgttcttca gacaacacca ttcgcttctg gaacttggac agcagccctg attctcaccg  1440
     gcagaaaaac atcttcagca cacccctgct gaaggccgtg tacgtggaga atgacatcca  1500
     gcacctgcag gacatgtcac acttcccaga ccgggggagc gagaatggga cacccatgga  1560
     cgcgaaagcc ggqgtqcggg tcatgcaggt cagtcctgac ggccagcatt tggcttcagg  1620
     cgaccgaagt ggaaatctga ggatccacga gctgcacttc atggacgagc tggtcaaggt  1680
     ggaggcccat gatgctgagg tqctgtgcct ggagtactcc aagccagaga cggggctgac  1740
     cttgctggcc tcagccagtc gggaccggct gatccatgcg ctgaacgtgg agaagaacta  1800
     caacctggag cagacgctgg atgaccactc ctcctccatc accgccatca agttcgctgg  1860
     caacagagac atccagatga tcagctgtgg ggctgacaag agcatctact ttcgcagtgc  1920
     ccagcagggt tcggatggac tacactttgt ccgtacccac cacgtagcag agaaaaccac  1980
     cttgtatgac atggacattg acatcaccca gaagtacgtg gccgtggcct gccaggaccg  2040
     caatgtgaga gtctacaaca ctgtgaacgg gaagcagaag aagtgctaca agggctccca  2100
     gggtgacgaa gggtccttgc tgaaggtcca cgtggacccc tcaggcacct tcctggccac  2160
```

-continued

```
cagctgctct gacaaaagca tctcagtgat tgactttcac tcgggcgagt gcattgccaa 2220
gacgtttggc cactcagaaa ttattaccag catgaagctc acctatgact gtcatcactt 2280
gaccacagta tctggagaca gctgcgtgtt catctggcac ctgggcccgg agatcaccaa 2340
ctgcatgaag cagcacttgc tggagattga ccaccggcag cagcagcagc acacaaatga 2400
caagaagcgg agtggccacc ccaggcagga cacgtatgtg tccacaccta gtgagattca 2460
ctccctgagc cctggagagc aaacagagga tgatctggag aaagagtgtg agccagaaga 2520
gatgctgaag acaccatcca aagatagctt ggatccagat cctcgttgcc cgctaaccaa 2580
cggcaagctg ccactgtggg caaagcggct gctaggggac gatgatgtgg cagatggctt 2640
ggccttccac gccaagcgca gctaccagcc ccacggccgc tgggcagagc gggccggcca 2700
agagcccctc aagaccatcc tggatgccca ggacctggat tgctacttta cccccatgaa 2760
gcccgagagt ctggagaact ccattctgga ttcactggag ccacagagcc tggccagcct 2820
gctgagcgag tcagagagtc cccaggaagc tggccgcggg cacccctcct tcctgcccca 2880
gcagaaggaa tcacctgagg ccagtgagcc catcctctac tctctggagg cagaagcgac 2940
agtcacaggg acagacagcc agtcttgcag gaaggaggtg gaggccgggc ctggagacca 3000
gcagggcgac tcctacctca gggtgtcctc cgacagccca aaggaccaga gcccgcctga 3060
ggactcgggg gagtcagagg ccgacctgga gtgcagcttc gcagccatcc actccccagc 3120
tccgcctcct gaccctgccc ctcggtttgc cacgtcgctg ccccatttcc caggatgcgc 3180
aggtcccaca gaagatgagc tgtccctgcc cgagggaccc agcgtcccca gcagctccct 3240
accccagacc ccggagcagg agaagttcct ccgccaccac tctgagacac tgactgagtc 3300
cccctgcaga gagctcttcc ccgcagctct gggagacgtg gaggcctctg aagctgaaga 3360
ccacctcttc aacccacgcc tgagtatctc cacgcagttc ccctcaagcc tccagaaggc 3420
atccaggttc acccacacct tccctccccg ggcaacccag tgccttgtga agtctccaga 3480
ggtcaagctc atggaccgag gcggaagcca gcccagagca ggtactggct acgcctcccc 3540
agacaggacc cacgtcctcg ctgcagggaa ggctgaagag accctggagg cctggcgccc 3600
accacctccc tgccttacga gcctggcgtc ctgtgtccct gcttcctccg tgctgcccac 3660
agacaggaat ctcccaacgc ccacatctgc acccacccca ggcctggctc agggtgtcca 3720 tgcccccctcc acctgttcct acatggaggc cactgccagc tcccgtgcca ggatatcacg 3780
cagcatctcc ctcggtgaca gtgagggccc tatcgtggcc acactggccc agcccctccg 3840
taggccatcg tccgttgggg agctggcctc cttgggccag gagcttcagg ccatcaccac 3900
cgcgacaaca cccagtttgg acagtgaggg ccaagagcct gccctgcgtt cctggggcaa 3960 ccacagaggcc cgggccaacc tgagactgac cctgtcaagt gcctgtgatg ggctcctgca 4020
gccccccgtg gatacccagc ctggcgtcac cgtccctgca gtgagcttcc cagcccctag 4080
ccctgtggaa gagagcgccc tgaggctcca cggctctgcc tttcgcccaa gtctcccagc 4140
tcctgagtcc cctggccttc ctgcccaccc cagtaacccc cagcttccag aggcccggcc 4200
tggcatccct ggcggcactg cctccctcct ggagcccacc tccggtgcac ttggtctgtt 4260
acagggcagc cctgcccgct ggagtgagcc ctgggtgccg gttgaagccc tgcccccatc 4320
tccccttgag ctgagcaggg tggggaacat cttgcacagg ctgcagacca ccttccaaga 4380
agccctcgac ctttaccgtg tgttggtctc cagtggccag gtggacaccg ggcagcagca 4440
ggcacggact gagctggtct ccaccttcct gtggatccac agccagctgg aggctgaatg 4500
cctggtgggg actagtgtgg ccccagccca ggctctgccc agcccaggac ccccgtcccc 4560
accgacgctg taccccctgg ccagcccaga cctgcaggcc ctgctggaac actactcgga 4620
```

-continued

```
gctgctggtg caggccgtgc ggaggaaggc acgggggcac tgagggcgca gcccctccac 4680
cgcagccctg ctgcttctga ggacttaggt attttaagcg aataaactga cagctttgag 4740
gaatga                                                              4746
```

Homo sapiens WD repeat domain 62 (WDR62) nucleotide sequence,
NCBI Reference Sequence: NM_001083961

(SEQ ID NO: 2)

```
Met Ala Ala Val Gly Ser Gly Gly Tyr Ala Arg Asn Asp Ala Gly Glu
1               5                   10                  15

Lys Leu Pro Ser Val Met Ala Gly Val Pro Ala Arg Arg Gly Gln Ser
            20                  25                  30

Ser Pro Pro Ala Pro Pro Ile Cys Leu Arg Arg Thr Arg Leu
        35                  40                  45

Set Thr Ala Ser Glu Glu Thr Val Gln Asn Arg Val Ser Leu Glu Lys
    50                  55                  60

Val Leu Gly Ile Thr Ala Gln Asn Ser Ser Gly Leu Thr Cys Asp Pro
65              70                  75                  80

Gly Thr Gly His Val Ala Tyr Leu Ala Gly Cys Val Val Ile Leu
                85                  90                  95

Asp Pro Lys Glu Asn Lys Gln Gln His Ile Phe Asn Thr Ala Arg Lys
            100                 105                 110

Ser Leu Ser Ala Leu Ala Phe Ser Pro Asp Gly Lys Tyr Ile Val Thr
        115                 120                 125

Gly Glu Asn Gly His Arg Pro Ala Val Arg Ile Trp Asp Val Glu Glu
    130                 135                 140

Lys Asn Gln Val Ala Glu Met Leu Gly His Lys Tyr Gly Val Ala Cys
145             150                 155                 160

Val Ala Phe Ser Pro Asn Met Lys His Ile Val Ser Met Gly Tyr Gln
                165                 170                 175

His Asp Met Val Leu Asn Val Trp Asp Trp Lys Lys Asp Ile Val Val
            180                 185                 190

Ala Ser Asn Lys Val Ser Cys Arg Val Ile Ala Leu Ser Phe Ser Glu
        195                 200                 205

Asp Ser Ser Tyr Phe Val Thr Val Gly Asn Arg His Val Arg Phe Trp
    210                 215                 220

Phe Leu Glu Val Ser Thr Glu Thr Lys Val Thr Ser Thr Val Pro Leu
225             230                 235                 240

Val Gly Arg Ser Gly Ile Leu Gly Glu Leu His Asn Asn Ile Phe Cys
                245                 250                 255

Gly Val Ala Cys Gly Arg Gly Arg Met Ala Gly Ser Thr Phe Cys Val
            260                 265                 270

Her Tyr Ser Gly Leu Leu Cys Gln Phe Asn Glu Lys Arg Val Leu Glu
        275                 280                 285

Lys Trp Ile Asn Leu Lys Val Ser Leu Ser Ser Cys Leu Cys Val Ser
    290                 295                 300

Gln Glu Leu Ile Phe Cys Gly Cys Thr Asp Gly Ile Val Arg Ile Phe
305             310                 315                 320

Gln Ala His Ser Leu His Tyr Leu Ala Asn Leu Pro Lys Pro His Tyr
                325                 330                 335

Leu Gly Val Asp Val Ala Gln Gly Leu Glu Pro Ser Phe Leu Phe His
            340                 345                 350

Arg Lys Ala Glu Ala Val Tyr Pro Asp Thr Val Ala Leu Thr Phe Asp
        355                 360                 365

Pro Ile His Gln Trp Leu Ser Cys Val Tyr Lys Asp His Ser Ile Tyr
    370                 375                 380
```

-continued

```
Ile Trp Asp Val Lys Asp Ile Asn Arg Val Gly Lys Val Trp Ser Glu
385                 390                 395                 400
Leu Phe His Ser Ser Tyr Val Trp Asn Val Glu Val Tyr Pro Glu Phe
            405                 410                 415
Glu Asp Gln Arg Ala Cys Leu Pro Ser Gly Ser Phe Leu Thr Cys Her
        420                 425                 430
Her Asp Asn Thr Ile Alp Phe Trp Asn Leu Asp Ser Ser Pro Asp Her
    435                 440                 445
His Trp Gln Lys Asn Ile Phe Ser Asn Thr Leu Leu Lys Val Val Tyr
450                 455                 460
Val Glu Asn Asp Ile Gln His Leu Gln Asp Met Ser His Phe Pro Asp
465                 470                 475                 480
Arg Gly Ser Glu Asn Gly Thr Pro Met Asp Val Lys Ala Gly Val Arg
            485                 490                 495
Val Met Gln Val Ser Pro Asp Gly Gln His Leu Ala Ser Gly Asp Arg
        500                 505                 510
Ser Gly Asn Leu Arg Ile His Glu Leu His Phe Met Asp Glu Leu Val
    515                 520                 525
Lys Val Glu Ala His Asp Ala Glu Val Leu Cys Leu Glu Tyr Ser Lys
530                 535                 540
Pro Glu Thr Gly Leu Thr Leu Leu Ala Ser Ala Ser Arg Asp Arg Leu
545                 550                 555                 560
Ile His Val Leu Asn Val Glu Lys Asn Tyr Asn Leu Glu Gln Thr Leu
            565                 570                 575
Asp Asp His Ser Ser Ser Ile Thr Ala Ile Lys Phe Ala Gly Asn Arg
        560                 585                 590
Asp Ile Gln Met Ile Ser Cys Gly Ala Asp Lys Ser Ile Tyr Phe Arg
    595                 600                 605
Ser Ala Gln Gln Gly Ser Asp Gly Leu His Phe Val Arg Thr His His
610                 615                 620
Val Ala Glu Lys Thr Thr Leu Tyr Asp Met Asp Ile Asp Ile Thr Gln
625                 630                 635                 640
Lys Tyr Val Ala Val Ala Cys Gln Asp Arg Asn Val Arg Val Tyr Asn
            645                 650                 655
Thr Val Asn Gly Lys Gln Lys Lys Cys Tyr Lys Gly Ser Gln Gly Asp
        660                 665                 670
Glu Sly Ser Leu Leu Lys Val His Val Asp Pro Set Gly Thr Phe Leu
    675                 680                 685
Ala Thr Ser Cys Ser Asp Lys Ser Ile Ser Val Ile Asp Phe Tyr Ser
690                 695                 700
Gly Glu Cys Ile Ala Lys Met Phe Gly His Ser Glu Ile Ile Thr Ser
705                 710                 715                 720
Met Lys Phe Thr Tyr Asp Cys His His Leu Ile Thr Val Ser Gly Asp
            725                 730                 735
Ser Cys Val Phe Ile Trp His Leu Gly Pro Glu Ile Thr Asn Cys Met
        740                 745                 750
Lys Gln His Leu Leu Glu Ile Asp His Arg Gln Gln Gln His Thr
    755                 760                 765
Asn Asp Lys Lys Arg Set Gly His Pro Arg Gln Asp Thr Tyr Val Ser
770                 775                 780
Thr Pro Ser Glu Ile His Ser Leu Ser Pro Gly Glu Gln Thr Glu Asp
785                 790                 795                 800
Asp Leu Glu Glu Glu Cys Glu Pro Glu Glu Met Leu Lys Thr Pro Ser
            805                 810                 815
```

-continued

```
Lys Asp Ser Leu Asp Pro Asp Pro Arg Cys Leu Leu Thr Asn Gly Lys
            820                 825                 830

Leu Pro Leu Trp Ala Lys Arg Leu Gly Asp Asp Val Ala Asp
        835                 840                 845

Gly Leu Ala Phe His Ala Lys Arg Ser Tyr Gln Pro His Gly Arg Trp
    850                 855                 860

Ala Glu Arg Ala Gly Gln Glu Pro Leu Lys Thr Ile Leu Asp Ala Gln
865                 870                 875                 880

Asp Leu Asp Cys Tyr Phe Thr Pro Met Lys Pro Glu Ser Leu Glu Asn
                885                 890                 895

Ser Ile Leu Asp Ser Leu Glu Pro Gln Ser Leu Ala Ser Leu Leu Ser
            900                 905                 910

Glu Ser Glu Ser Pro Gln Glu Ala Gly Arg Gly His Pro Ser Phe Leu
        915                 920                 925

Pro Gln Gln Lys Glu Ser Ser Glu Ala Ser Glu Leu Ile Leu Tyr Ser
    930                 935                 940

Leu Glu Ala Glu Val Thr Val Thr Gly Thr Asp Ser Gln Tyr Cys Arg
945                 950                 955                 960

Lys Glu Val Glu Ala Gly Pro Gly Asp Gln Gln Gly Asp Ser Tyr Leu
                965                 970                 975

Arg Val Ser Ser Asp Ser Pro Lys Asp Gln Ser Pro Pro Glu Asp Ser
            980                 985                 990

Gly Glu Ser Glu Ala Asp Leu Glu Cys Ser Phe Ala Ala Ile His Ser
        995                 1000                1005

Pro Ala Pro Pro Asp Pro Ala Pro Arg Phe Ala Thr Ser Leu
    1010                1015                1020

Pro His Phe Pro Gly Cys Ala Gly Pro Thr Glu Asp Glu Leu Ser
    1025                1030                1035

Leu Pro Glu Gly Pro Ser Val Pro Ser Ser Leu Pro Gln Thr
    1040                1045                1050

Pro Glu Gln Glu Lys Phe Leu Arg His His Phe Glu Thr Leu Thr
    1055                1060                1065

Glu Ser Pro Cys Arg Glu Leu Phe Pro Ala Ala Leu Gly Asp Val
    1070                1075                1080

Glu Ala Ser Glu Ala Glu Asp His Phe Phe Asn Pro Arg Leu Ser
    1085                1090                1095

Ile Ser Thr Gln Phe Leu Ser Ser Leu Gln Lys Ala Ser Arg Phe
    1100                1105                1110

Thr His Thr Phe Pro Pro Arg Ala Thr Gln Cys Leu Val Lys Ser
    1115                1120                1125

Pro Glu Val Lys Leu Met Asp Arg Gly Gly Ser Gln Pro Arg Ala
    1130                1135                1140

Gly Thr Gly Tyr Ala Ser Pro Asp Arg Thr His Val Leu Ala Ala
    1145                1150                1155

Gly Lys Ala Glu Glu Thr Leu Glu Ala Trp Arg Pro Pro Pro
    1160                1165                1170

Cys Leu Thr Ser Leu Ala Ser Cys Val Pro Ala Ser Ser Val Leu
    1175                1180                1185

Pro Thr Asp Arg Asn Leu Pro Thr Pro Thr Ser Ala Pro Thr Pro
    1190                1195                1200

Gly Leu Ala Gln Gly Val His Ala Pro Ser Thr Cys Ser Tyr Met
    1205                1210                1215

Glu Ala Thr Ala Ser Ser Arg Ala Arg Ile Ser Arg Ser Ile Her
    1220                1225                1230
```

-continued

Leu Gly Asp Ser Glu Gly Pro Ile Val Ala Thr Leu Ala Gln Pro
1235                 1240                 1245

Leu Arg Arg Pro Ser Ser Val Gly Glu Leu Ala Ser Leu Gly Gln
1250                 1255                 1260

Glu Leu Gln Ala Ile Thr Thr Ala Thr Thr Pro Ser Leu Asp Ser
1265                 1270                 1275

Glu Gly Gln Glu Pro Ala Leu Arg Ser Trp Gly Asn His Glu Ala
1280                 1285                 1290

Arg Ala Asn Leu Arg Leu Thr Leu Ser Ser Ala Cys Asp Gly Leu
1295                 1300                 1305

Leu Gln Pro Pro Val Asp Thr Gln Pro Gly Val Thr Val Pro Ala
1310                 1315                 1320

Val Ser Phe Pro Ala Pro Ser Pro Val Glu Glu Ser Ala Leu Arg
1325                 1330                 1335

Leu His Gly Ser Ala Phe Arg Pro Ser Leu Pro Ala Pro Glu Ser
1340                 1345                 1350

Pro Gly Leu Pro Ala His Pro Ser Asn Pro Gln Leu Pro Glu Ala
1355                 1360                 1365

Arg Pro Gly Ile Pro Gly Gly Thr Ala Ser Leu Leu Glu Pro Thr
1370                 1375                 1380

Ser Gly Ala Leu Gly Leu Leu Gln Gly Ser Pro Ala Arg Trp Ser
1385                 1390                 1395

Glu Pro Trp Val Pro Val Glu Ala Leu Pro Pro Ser Pro Leu Glu
1400                 1405                 1410

Leu Ser Arg Val Gly Asn Ile Leu His Arg Leu Gln Thr Thr Phe
1415                 1420                 1425

Gln Glu Ala Leu Asp Leu Tyr Arg Val Leu Val Ser Ser Gly Gln
1430                 1435                 1440

Val Asp Thr Gly Gln Gln Gln Ala Arg Thr Glu Leu Val Ser Thr
1445                 1450                 1455

Phe Leu Trp Ile His Ser Gln Leu Glu Ala Glu Cys Leu Val Gly
1460                 1465                 1470

Thr Ser Val Ala Pro Ala Gln Ala Leu Pro Ser Pro Gly Pro Pro
1475                 1480                 1485

Her Pro Pro Thr Leu Tyr Pro Leu Ala Ser Pro Asp Leu Gln Ala
1490                 1495                 1500

Leu Leu Glu His Tyr Ser Glu Leu Leu Val Gln Ala Val Arg Arg
1505                 1510                 1515

Lys Ala Arg Gly His
1520

Mus musculus WD repeat domain 62 (WDR62) nucleotide sequence,
NCBI Reference Sequence: NM_146186

(SEQ ID NO: 3)

```
ggctttcccg cggccattcg ctattcgagt gggtgctggc tacaggcggc tgttaagaag    60
cgtaacggac actggtctcc gacagcatga tggctgcctt agcggccgga ggttatacgc   120
ggagtgacac gatagaaaag ctgtcctctg tcatggcggg agttccggcg cggagaaacc   180
agtcctcccc gcctcctgcc ccaccgctct gcctccggcg gcggacgcga ctcgcggcg    240
ctcccgagga cactgtgcag aaccgggtga cacttgagaa ggtgcttggc atcacagccc   300
agaacagcag cgggctaacc tgtgaccctg cacaggcca tgtggcctac ttagcagggt    360
gcgtggtggt ggtcttgaac cccaaggaga acaagcagca gcatatattt aacacaacca   420
ggaagtccct gagtgctctg gccttctccc cagatgggaa gtacatagtg acaggagaga   480
atggacaccg gccagctgtg cgcatctggg atgtggagga gaagactcaa gtggcagaga   540
```

-continued

```
tgctgggcca caagtatggt gtggcctgtg tggctttctc acccaatatg aagcacatcg    600
tgtccatggg ctaccaacat gacatggtcc tcaatgtttg ggattggaag aaagacattg    660
tggtggcttc caacaaggtg tcatgtagag tcatcgctct ctccttctct gaggacagca    720 gctatttgt caccgttggg aatcggcatg tgaggtttg gttcttagaa gcctctactg    780
aggccaaggt aaccagcaca gtgcccctgg taggacgctc aggcatcctg ggtgagctgc    840
acaacaatat cttttgtggc gtggcctgcg gccggggccg gatggcaggc aataccttct    900
gtgtgtccta ctctggcctc ctctgccagt tcaatgagaa aagggtgctg acaagtgga     960 tcaacctgaa ggtctccttg tcttcctgcc tgtgtgtcag tgacgagttg atcttctgtg   1020
gatgcacaga cgggatagtc cgcatcttcc aggcccacag cctactctac ctcaccaacc   1080
tgcccaaacc acactacctg ggagtggacg tgcccacgg actggactcc agcttcctct    1140
tccacagaaa agcagaagca gtctacccag atacagtggc cctgacccttt gaccccgtcc   1200 accagtggct gtcctgtgtt tacaaagacc acagcatcta catctgggat gtcaaggaca   1260
ttgatgaagt cagcaagata tggtcagagc tcttccacag ctcctttgtc tggaatgtag   1320
aggtgtaccc tgaatttgaa gaccagagag cttgcctgcc gtccgggact tttctgactt   1380
gttcctcaga caataccatc cgcttctgga atttggatag cgcctctgac actcgatggc   1440
aaaagaacat cttcagcgat tctctgctga aggtggtcta tgtagagaat gacatccagc   1500
acctgcagga cctgtctcac ttcccagacc ggggcagtga aacggcact cccatggata    1560 tgaaagctgg ggttcgagtc atgcaggtca gtcctgacgg ccagcacttg gcttcaggcg   1620
accgcagtgg aaatctqagg atccacgagc tgcacttcat ggatgagctg atcaaggtgg   1680
aggcccacga tgctgaggtg ctgtgcctgg agtactccaa gcctgagaca ggagtgactt   1740
tgctggcttc agccagtcgg acagactca tccatgtgtt aaacgtggag aagaactaca    1800
acctggagca gaccctggac gaccactcct cctccatcac agccattaag tttgctggca   1860
ccagagatgt ccagatgatc agttgtggag ctgacaagag catctacttt cgcagtgccc   1920
agcaggcctc ggatqgactg cactctgccc gtacccacca cgtagcagag aagaccacct   1980
tgtatgacat ggatatcgac atcacacaga agtatgtggc agtggcctgc caggaccgca   2040
acgtaagggt ctacaacacc gtgagtggga acagaagaa gtgctacaag ggttcccagg    2100
gcgacgaagg gtccctgctg aaggtccacg tggacccctc aggcaccttc ctggccacaa   2160 gctqctctga caaaagcatc tccttgattg acttttactc gggcgagtgt gttgccaaga   2220
tgtttggcca tteggaaatt gtcactggca tgaagttcac ctacgactgc cgccacttga   2280
tcacagcatc tggagacagc tgtgtgttca tctggcacct gggccggag accaccacct    2340 gcatgaagca gcacttgctg gagatcaacc accaggagca gcagcaqcag cccaaggacc   2400 agaagtggag tggccctccc agccaggaga catatgcatc cacaccaagt gagattcgtt   2460
ccctgagccc cggagagcag acagaggatg agatgaggga ggaatgtgag ccagaagagt   2520
tgctgaaaac accatccaaa gacagcttqg acccagatcc tcgatgcctg ctgacaaatg   2580
gcaagctgcc accctgggca aagcggctgc taggggatga tgatgtggca gacagctcag   2640 cttttccacgc caagcgcaac taccagccac atggccgttg ggcagagcgg gctgagcagg   2700 aaccctcaa gaccatcctg gatgcctgga gcctggattc ctactttaca cccatgaagc    2760
ctgaaaatct ccaagactct gttctggact cagtagagcc acagaacctg caggcctgc    2820 taagtgagtg ttcactcggt aatggacaca cgtctccggg agaaggcttg gtgagctacc   2880
tacttcaccc agagttaggg agtcccaaag aggacaaccg aggccacccc tcctacctgc   2940
```

-continued

```
ctctacagag ggaagccacc gaggcaagcg aactcatcct ctgctcccca gaggcggaag   3000
tgtcacttac agggatgcac agggagtatt atgaggagga gacagaggca ggacctgaag   3060
accagcaagg cgacacctat ctcagggtct cttccgtcag ttcaaaggat cagagccccc   3120
ctgaggactc aggggagtca gaggctgaac tggagtgcag ctttgccgcc gcccacagct   3180
cagctcctca aacggaccct ggccctcacc tcaccatgac agcaggtaag ccagagtacc   3240
caagtacaga agagctttcc cagcctgagc tgccaggctt gggcaatggc tccttacccc   3300
agacacctga gcaggagaag ttcctccgcc accattttga cacttact gatgcccta    3360 ctgaagagct ctttcatgga tccctgggag acataaagat ctcagagact gaggactatt   3420
tcttcaatcc ccggctgagc atatccaccc agttcctctc ccgcctccag aagacctcca   3480
ggtgccctcc ccgactgccc ctgcaccttta tgaagtctcc agaggctcag cctgtgggcc   3540 aaggggggcaa ccagcccaaa gcagggcccc tgagagcagg tactggctac atgtcctcag   3600
atgggaccaa cgtcctctct gggcagaagg ctgaagaaac tcaagaggcc ttgagtctac   3660
tggacaggaa gcctccaaca cccacatctg tactgaccac aggccgggag caaagtatct   3720
ccgccccatc ttcgtgttct tacctggagt ccacaacgag ctcacatgcc aagacgacac   3780
gcagcatctc tcttggggac agtgagggcc ctgtgacagc tgagctaccc cagtcacttc   3840
acaagccctt atccctggc caggaactcc aagccatccc cactacagtg gcactgacct   3900
ccagcatcaa agaccacgag cctgcaccgc tttcctgggg caaccatgag gcccgagcca   3960
gcctgaaact gaccttatcc agtgtctgtg agcagctgct ctctccacct ccacaggagc   4020
cacccatcac ccatgtgtgg tctcaggaac ctgtggatgt cccacctagt atggcagtca   4080
cagtagccag cttctgtgca cccagccctg tagacatgag caccctggga ctccacagtt   4140
ctatgtttct cccaaagacc tcagcctctg gcccctaac ccctcctgcc cacctccaac    4200
ttctagagac caggtctagg gtgcctggca gcactgctgc tctcctggag cccacccccg   4260
atgcatcagt tgtgatcgca gacagccctg gacactggga cacagaagtc cctacccccag   4320 aactcctagg cagtgtggaa tcagtcttgc acaggctgca gactgccttc caagaagctc   4380
ttgacattta ccgcatgctg gtctccagca gccagctggg tcctgagcag cagcaggcac   4440
agaccgagct ggcctccacc ttccactgga tcctcaacca gctagaagcc agcaactgta   4500
tggctgcagc taacttggcc ccacccccaga cactgcctag cccagaccct ctgtccctac   4560
ctacactttg tcccctggcc agcccaaacc tgcaggccct gctggaacac tactcagagt   4620
tgctggtgca agcagtgagg aggaaggcaa ggggtgactg agaacctgaa gcccctctac   4680
caaagccccg ctgccctgga gaaatagatt tgtaaaccaa taaactgaca gttgtttcct   4740
ggaa                                                               4744
```

*Mus musculus* WD repeat domain 62 (WDR62) amino acid sequence,
NCBI Reference Sequence: NM_146186

(SEQ ID NO: 4)

```
Met Met Ala Ala Leu Ala Ala Gly Gly Tyr Thr Arg Ser Asp Thr Ile
1               5                   10                  15

Glu Lys Leu Ser Ser Val Met Ala Gly Val Pro Ala Arg Arg Asn Gln
            20                  25                  30

Ser Ser Pro Pro Pro Ala Pro Pro Leu Cys Leu Arg Arg Arg Thr Arg
        35                  40                  45

Leu Ala Ala Ala Pro Glu Asp Thr Val Gln Asn Arg Val Thr Leu Glu
    50                  55                  60

Lys Val Leu Gly Ile Thr Ala Gln Asn Ser Ser Gly Leu Thr Cys Asp
65                  70                  75                  80

Pro Gly Thr Gly His Val Ala Tyr Leu Ala Gly Cys Val Val Val Val
```

-continued

```
            85                  90                  95
Leu Asn Pro Lys Glu Asn Lys Gln Gln His Ile Phe Asn Thr Thr Arg
            100                 105                 110
Lys Ser Leu Ser Ala Leu Ala Phe Ser Pro Asp Gly Lys Tyr Ile Val
            115                 120                 125
Thr Gly Glu Asn Gly His Arg Pro Ala Val Arg Ile Trp Asp Val Glu
            130                 135                 140
Glu Lys Thr Gln Val Ala Glu Met Leu Gly His Lys Tyr Gly Val Ala
145                 150                 155                 160
Cys Val Ala Phe Ser Pro Asn Met Lys His Ile Val Ser Met Gly Tyr
            165                 170                 175
Gln His Asp Met Val Leu Asn Val Trp Asp Trp Lys Lys Asp Ile Val
            180                 185                 190
Val Ala Ser Asn Lys Val Ser Cys Arg Val Ile Ala Leu Ser Phe Her
            195                 200                 205
Glu Asp Ser Ser Tyr Phe Val Thr Val Gly Asn Arg His Val Arg Phe
            210                 215                 220
Trp Phe Leu Glu Ala Ser Thr Glu Ala Lys Val Thr Ser Thr Val Pro
225                 230                 235                 240
Leu Val Gly Arg Ser Gly Ile Leu Gly Glu Leu His Asn Asn Ile Phe
            245                 250                 255
Cys Gly Val Ala Cys Gly Arg Gly Arg Met Ala Gly Asn Thr Phe Cys
            260                 265                 270
Val Ser Tyr Ser Gly Leu Leu Cys Gln Phe Asn Glu Lys Arg Val Leu
            275                 280                 285
Asp Lys Trp Ile Asn Leu Lys Val Ser Leu Ser Ser Cys Leu Cys Val
            290                 295                 300
Her Asp Glu Leu Ile Phe Cys Gly Cys Thr Asp Gly Ile Val Arg Ile
305                 310                 315                 320
Phe Gln Ala His Ser Leu Leu Tyr Leu Thr Asn Leu Pro Lys Pro His
            325                 330                 335
Tyr Leu Gly Val Asp Val Ala His Gly Leu Asp Ser Ser Phe Leu the
            340                 345                 350
His Arg Lys Ala Glu Ala Val Tyr Pro Asp Thr Val Ala Leu Thr the
            355                 360                 365
Asp Pro Val His Gln Trp Leu Ser Cys Val Tyr Lys Asp His Ser Ile
            370                 375                 380
Tyr Ile Trp Asp Val Lys Asp Ile Asp Glu Val Ser Lys Ile Trp Ser
385                 390                 395                 400
Glu Leu the His Ser Ser the Val Trp Asn Val Glu Val Tyr Pro Glu
            405                 410                 415
Phe Glu Asp Gln Arg Ala Cys Leu Pro Ser Gly Thr Phe Leu Thr Cys
            420                 425                 430
Ser Ser Asp Asn Thr Ile Arg Phe Trp Asn Leu Asp Ser Ala Ser Asp
            435                 440                 445
Thr Arg Trp Gln Lys Asn Ile the Ser Asp Ser Leu Leu Lys Val Val
            450                 455                 460
Tyr Val Glu Asn Asp Ile Gln His Leu Gln Asp Leu Ser His Phe Pro
465                 470                 475                 480
Asp Arg Gly Ser Glu Asn Gly Thr Pro Met Asp Met Lys Ala Gly Val
            485                 490                 495
Arg Val Met Gln Val Ser Pro Asp Gly Gln His Leu Ala Ser Gly Asp
            500                 505                 510
Arg Ser Gly Asn Leu Arg Ile His Glu Leu His Phe Met Asp Glu Leu
```

-continued

```
            515                 520                 525
Ile Lys Val Glu Ala His Asp Ala Glu Val Leu Cys Leu Glu Tyr Ser
    530                 535                 540

Lys Pro Glu Thr Gly Val Thr Leu Leu Ala Ser Ala Ser Arg Asp Arg
545                 550                 555                 560

Leu Ile His Val Leu Asn Val Glu Lys Asn Tyr Asn Leu Glu Gln Thr
                565                 570                 575

Leu Asp Asp His Ser Ser Ile Thr Ala Ile Lys Phe Ala Gly Thr
                580                 585                 590

Arg Asp Val Gln Met Ile Ser Cys Gly Ala Asp Lys Ser Ile Tyr Phe
                595                 600                 605

Arg Ser Ala Gln Gln Ala Ser Asp Gly Leu His Phe Val Arg Thr His
    610                 615                 620

His Val Ala Glu Lys Thr Thr Leu Tyr Asp Met Asp Ile Asp Ile Thr
625                 630                 635                 640

Gln Lys Tyr Val Ala Val Ala Cys Gln Asp Arg Asn Val Arg Val Tyr
                645                 650                 655

Asn Thr Val Ser Gly Lys Gln Lys Cys Tyr Lys Gly Ser Gln Gly
                660                 665                 670

Asp Glu Gly Ser Leu Leu Lys Val His Val Asp Pro Ser Gly Thr Phe
                675                 680                 685

Leu Ala Thr Ser Cys Ser Asp Lys Ser Ile Ser Leu Ile Asp Phe Tyr
    690                 695                 700

Ser Gly Glu Cys Val Ala Lys Met Phe Gly His Ser Glu Ile Val Thr
705                 710                 715                 720

Gly Met Lys Phe Thr Tyr Asp Cys Arg His Leu Ile Thr Val Ser Gly
                725                 730                 735

Asp Ser Cys Val Phe Ile Trp His Leu Gly Pro Glu Ile Thr Thr Cys
                740                 745                 750

Met Lys Gln His Leu Leu Glu Ile Asn His Gln Glu Gln Gln Gln
    755                 760                 765

Pro Lys Asp Gln Lys Trp Ser Gly Pro Pro Ser Gln Glu Thr Tyr Ala
    770                 775                 780

Ser Thr Pro Ser Glu Ile Arg Ser Leu Ser Pro Gly Glu Gln Thr Glu
785                 790                 795                 800

Asp Glu Met Glu Glu Glu Cys Glu Pro Glu Glu Leu Leu Lys Thr Pro
                805                 810                 815

Ser Lys Asp Ser Leu Asp Pro Asp Pro Arg Cys Leu Leu Thr Asn Gly
                820                 825                 830

Lys Leu Pro Leu Trp Ala Lys Arg Leu Leu Gly Asp Asp Val Ala
    835                 840                 845

Asp Ser Ser Ala Phe His Ala Lys Arg Ser Tyr Gln Pro His Gly Arg
    850                 855                 860

Trp Ala Glu Arg Ala Glu Gln Glu Pro Leu Lys Thr Ile Leu Asp Ala
865                 870                 875                 880

Trp Ser Leu Asp Ser Tyr Phe Thr Pro Met Lys Pro Glu Asn Leu Gln
                865                 890                 895

Asp Ser Val Leu Asp Ser Val Glu Pro Gln Asn Leu Ala Gly Leu Leu
                900                 905                 910

Ser Glu Cys Ser Leu Gly Asn Gly His Thr Ser Pro Gly Glu Gly Leu
    915                 920                 925

Val Ser Tyr Leu Leu His Pro Glu Leu Gly Ser Pro Lys Glu Asp Asn
    930                 935                 940

Arg Gly His Pro Ser Tyr Leu Pro Leu Gln Arg Glu Ala Thr Glu Ala
```

-continued

```
            945                 950                 955                 960
        Ser Glu Leu Ile Leu Cys Ser Pro Glu Ala Glu Val Ser Leu Thr Gly
                        965                 970                 975
        Met His Arg Glu Tyr Tyr Glu Glu Thr Glu Ala Gly Pro Glu Asp
                        980                 985                 990
        Gln Gln Gly Asp Thr Tyr Leu Arg Val Ser Ser Val Ser Lys Asp
                        995                 1000                1005
        Gln Ser Pro Glu Asp Ser Gly Glu Ser Ala Glu Leu Glu
            1010                1015                1020
        Cys Ser Phe Ala Ala Ala His Ser Ser Ala Pro Gln Thr Asp Pro
            1025                1030                1035
        Gly Pro His Leu Thr Met Thr Ala Gly Lys Pro Glu Tyr Pro Ser
            1040                1045                1050
        Thr Glu Glu Leu Ser Gln Pro Glu Leu Pro Gly Leu Gly Asn Gly
            1055                1060                1065
        Ser Leu Pro Gln Thr Pro Glu Gln Glu Lys Phe Leu Arg His His
            1070                1075                1080
        Phe Glu Thr Leu Thr Asp Ala Pro Thr Glu Glu Leu Phe His Gly
            1085                1090                1095
        Ser Leu Gly Asp Ile Lys Ile Ser Glu Thr Glu Asp Tyr Phe Phe
            1100                1105                1110
        Asn Pro Arg Leu Ser Ile Ser Thr Gln Phe Leu Ser Arg Leu Gln
            1115                1120                1125
        Lys Thr Ser Arg Cys Pro Pro Arg Leu Pro Leu His Leu Met Lys
            1130                1135                1140
        Ser Pro Glu Ala Gln Pro Val Gly Gln Gly Gly Asn Gln Pro Lys
            1145                1150                1155
        Ala Gly Pro Leu Arg Ala Gly Thr Gly Tyr Met Ser Ser Asp Gly
            1160                1165                1170
        Thr Asn Val Leu Ser Gly Gln Lys Ala Glu Glu Thr Gln Glu Ala
            1175                1180                1185
        Leu Ser Leu Leu Asp Arg Lys Pro Pro Thr Pro Thr Ser Val Leu
            1190                1195                1200
        Thr Thr Gly Arg Glu Gln Ser Ile Ser Ala Pro Ser Ser Cys Ser
            1205                1210                1215
        Tyr Leu Glu Ser Thr Thr Ser Ser His Ala Lys Thr Thr Arg Ser
            1220                1225                1230
        Ile Ser Leu Gly Asp Ser Glu Gly Pro Val Thr Ala Glu Leu Pro
            1235                1240                1245
        Gln Ser Leu His Lys Pro Leu Ser Pro Gly Gln Glu Leu Gln Ala
            1250                1255                1260
        Ile Pro Thr Thr Val Ala Leu Thr Ser Ser Ile Lys Asp His Glu
            1265                1270                1275
        Pro Ala Pro Leu Ser Trp Gly Asn His Glu Ala Arg Ala Ser Leu
            1280                1285                1290
        Lys Leu Thr Leu Ser Ser Val Cys Glu Gln Leu Leu Ser Pro Pro
            1295                1300                1305
        Pro Gln Glu Pro Pro Ile Thr His Val Trp Ser Gln Glu Pro Val
            1310                1315                1320
        Asp Val Pro Pro Ser Met Ala Val Thr Val Ala Ser Phe Cys Ala
            1325                1330                1335
        Pro Ser Pro Val Asp Met Ser Thr Leu Gly Leu His Ser Ser Met
            1340                1345                1350
        Phe Leu Pro Lys Thr Ser Ala Ser Gly Pro Leu Thr Pro Pro Ala
```

```
His Leu Gln Leu Leu Glu Thr Arg Ser Arg Val Pro Gly Ser Thr
    1370                1375                1380

Ala Ala Leu Leu Glu Pro Thr Pro Asp Ala Ser Gly Val Ile Ala
    1385                1390                1395

Asp Ser Pro Gly His Trp Asp Thr Glu Val Pro Thr Pro Glu Leu
    1400                1405                1410

Leu Gly Ser Val Glu Ser Val Leu His Arg Leu Gln Thr Ala Phe
    1415                1420                1425

Gln Glu Ala Leu Asp Leu Tyr Arg Met Leu Val Ser Ser Ser Gln
    1430                1435                1440

Leu Gly Pro Glu Gln Gln Gln Ala Gln Thr Glu Leu Ala Ser Thr
    1445                1450                1455

Phe His Trp Ile Leu Asn Gln Leu Glu Ala Ser Asn Cys Met Ala
    1460                1465                1470

Ala Ala Asn Leu Ala Pro Pro Gln Thr Leu Pro Ser Pro Asp Pro
    1475                1480                1485

Leu Ser Leu Pro Thr Leu Cys Pro Leu Ala Ser Pro Asn Leu Gln
    1490                1495                1500

Ala Leu Leu Glu His Tyr Ser Glu Leu Leu Val Gln Ala Val Arg
    1505                1510                1515

Arg Lys Ala Arg Gly Asp
    1520
```

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of detecting a mutation in at least one allele of WDR62, comprising:
   a. obtaining a test sample from a subject suspected of having a neurological disease or disorder, wherein the test sample comprises a WDR62 nucleic acid or a fragment thereof;
   b. amplifying all, or a portion, of the WDR62 nucleic acid sequence in the test sample with a pair of primers;
   c. detecting the presence of a sequence selected from the group consisting of:
   (a) a serine at a position corresponding to position 224 of SEQ ID NO: 2;
   (b) a stop codon at a position corresponding to position 470 of SEQ ID NO:2;
   (c) a lysine at a position corresponding to position 526 of SEQ ID NO: 2;
   (d) a stop codon at a position corresponding to position 526 of SEQ ID NO:2;
   (e) a 4 bp deletion (TGCC) in exon 31 beginning at a position corresponding to codon 1402 of the WDR62 coding region, leading to a premature stop codon corresponding to codon 1413 of the WDR62 coding region (V1402GfsX12); and
   f) a 17-bp deletion in exon 30 leading to a frameshift at a position corresponding to codon 1280 of the WDR62 coding region resulting in a premature termination codon following a novel peptide of 20 amino acids (G1280AfsX21).

2. The method of claim 1, wherein the subject is a human.

3. The method of claim 1, wherein the subject is selected from the group consisting of: a child, an adolescent, and an adult.

4. The method of claim 1, wherein the subject is a parent.

5. The method of claim 1, wherein the subject is suspected of being a subject having at least one mutation in only one allele of WDR62.

6. The method of claim 1, wherein the subject is suspected of being an subject having at least one mutation on each allele of WDR62.

7. The method of claim 1, wherein the subject is suspected of having at least one neurological disease or disorder selected from the group consisting of intellectual disability, cerebral cortical malformation, microcephaly, agyria, pachygyria, hypoplasia of the corpus callosum, lissencephaly, schizencephaly, polymicrogyria and cerebellar hypoplasia.

8. The method of claim 1, wherein the test sample from the subject comprises genomic DNA.

9. The method of claim 1, wherein the test sample is a biological sample selected from the group consisting of blood, amniotic fluid, or cerebrospinal fluid.

10. The method of claim 1, further comprising contacting the WDR62 nucleic acid with a probe selected from the group consisting of:
   (a) a probe that hybridizes to a WDR62 nucleic acid comprising a sequence encoding a serine at a position corresponding to position 224 of SEQ ID NO: 2;
   (b) a probe that hybridizes to a WDR62 nucleic acid comprising a sequence encoding a stop codon at a position corresponding to position 470 of SEQ ID NO:2;
   (c) a probe that hybridizes to a WDR62 nucleic acid comprising a sequence encoding a lysine at a position corresponding to position 526 of SEQ ID NO: 2;

(d) a probe that hybridizes to a WDR62 nucleic acid comprising a sequence encoding a stop codon at a position corresponding to position 526 of SEQ ID NO:2;

(e) a probe that hybridizes to a WDR62 nucleic acid sequence comprising a 4 bp deletion corresponding to (TGCC) in exon 31 beginning at a position corresponding to codon 1402 of the WDR62 coding region, leading to a premature stop codon at a position corresponding to codon 1413 of the WDR62 coding region (V1402GfsX12);

(f) a probe that hybridizes to a WDR62 nucleic acid comprising a sequence corresponding to a 17-bp deletion in exon 30 leading to a frameshift at a position corresponding to codon 1280 of the WDR62 coding region resulting in a premature termination codon following a novel peptide of 20 amino acids (G1280AfsX21); and (g) a perfect match probe of (a)-(f).

11. The method of claim 10, wherein the probe or perfect match probe is detectably labeled.

12. A method of detecting a mutation in at least one allele of WDR62, comprising:
  a. obtaining a test sample from a subject
  b. amplifying all, or a portion of the WDR62 nucleic acid in the test sample with a pair of primers,
  c. detecting a mutation in at least one allele of WDR62 wherein the mutation is at least one mutation selected from the group consisting of:
    (a) a serine at a position corresponding to position 224 of SEQ ID NO: 2;
    (b) a stop codon at a position corresponding to position 470 of SEQ ID NO:2;
    (c) a lysine at a position corresponding to position 526 of SEQ ID NO: 2;
    (d) a stop codon at a position corresponding to position 526 of SEQ ID NO:2;
    (e) a 4 bp deletion (TGCC) in exon 31 beginning at a position corresponding to codon 1402 of the WDR62 coding region, leading to a premature stop codon corresponding to codon 1413 of the WDR62 coding region (V1402GfsX12); and
    f) a 17-bp deletion in exon 30 leading to a frameshift at a position corresponding to codon 1280 of the WDR62 coding region resulting in a premature termination codon following a novel peptide of 20 amino acids (G1280AfsX21).

13. The method of claim 12, wherein the subject is a human.

14. The method of claim 12, wherein the subject is suspected of having at least one neurological condition selected from the group consisting of intellectual disability, cerebral cortical malformation, microcephaly, agyria, pachygyria, hypoplasia of the corpus callosum, lissencephaly, schizencephaly, polymicrogyria and cerebellar hypoplasia.

15. The method of claim 13, wherein the test sample from the subject comprises genomic DNA.

16. The method of claim 12, wherein the test sample is a biological sample selected from the group consisting of blood, amniotic fluid, or cerebrospinal fluid.

17. The method of claim 12, further comprising contacting the WDR62 nucleic acid with a probe selected from the group consisting of:
  (a) a probe that hybridizes to a WDR62 nucleic acid comprising a sequence encoding a serine at a position corresponding to position 224 of SEQ ID NO: 2;
  (b) a probe that hybridizes to a WDR62 nucleic acid comprising a sequence encoding a stop codon at a position corresponding to position 470 of SEQ ID NO:2;
  (c) a probe that hybridizes to a WDR62 nucleic acid comprising a sequence encoding a lysine at a position corresponding to position 526 of SEQ ID NO: 2;
  (d) a probe that hybridizes to a WDR62 nucleic acid comprising a sequence encoding a stop codon at a position corresponding to position 526 of SEQ ID NO:2;
  (e) a probe that hybridizes to a WDR62 nucleic acid sequence comprising a 4 bp deletion corresponding to (TGCC) in exon 31 beginning at a position corresponding to codon 1402 of the WDR62 coding region, leading to a premature stop codon at a position corresponding to codon 1413 of the WDR62 coding region (V1402GfsX12);
  (f) a probe that hybridizes to a WDR62 nucleic acid comprising a sequence corresponding to a 17-bp deletion in exon 30 leading to a frameshift at a position corresponding to codon 1280 of the WDR62 coding region resulting in a premature termination codon following a novel peptide of 20 amino acids (G1280AfsX21); and
  (g) a perfect match probe of (a)-(f).

18. The method of claim 17, wherein the probe or perfect match probe is detectably labeled.

19. The method of claim 1, wherein the subject is a fetus.

20. The method of claim 1, wherein the subject is a prospective parent.

* * * * *

```
                          SEQUENCE LISTING

<160> NUMBER OF SEQ ID NOS: 4

<210> SEQ ID NO 1
<211> LENGTH: 4746
<212> TYPE: DNA
<213> ORGANISM: Homo sapiens

<400> SEQUENCE: 1
tttcccgcgg ctgttcgctg ttccagtggg tcgtggcggt ggcggcagcg gcggttaggg      60
gatgtaacgg tcgcccgcct ccggcgtgac gatggcggcc gtagggtccg gaggctatgc     120
gcggaacgat gcaggggaga agctgccctc tgtcatggcg ggagttccgg cgcggagggg     180
ccagtcctcc ccgcccccg ccccaccaat ctgcctacgg cggcgacgc gactctcgac      240 ggcctccgag gagacggtgc agaaccgggt gtcactcgag aaggtgcttg gcatcacagc     300
ccagaacagc agtggcctaa cctgtgaccc cggcacaggc catgtggcct acctggcagg     360
ctgtgtggtg gtgattttgg accccaagga gaacaagcag cagcacatct ttaacaccgc     420
caggaagtct ctcagtgctc tggccttctc ccctgatggg aagtacatag tgacagggga     480
gaatgggcat aggcctgctg tgcgcatctg ggatgtggag gagaagaatc aggtggcgga     540
gatgctaggc cacaagtatg tgtggcgtg tgtggccttc tcacccaata tgaagcacat     600
cgtgtccatg ggctaccaac atgacatggt gctcaacgtc tgggactgga gaaagacat     660 cgtagtggcc tccaacaagg tatcttgtag agtcattgcc ctctccttct cagaggacag     720
cagctatttt gtcactgttg ggaaccgcca tgtgaggttc tggttcttgg aagtctccac     780
```

```
tgagacaaag gtgacgagca cagtgcccct tgtagggcgc tcgggcatcc tgggcgagct    840
gcacaacaac atcttctgtg gtgtggcctg cggtcggggc cggatggcgg gcagtacctt    900
ctgtgtgtcc tactcgggcc tcctctgcca gttcaatgag aagagggtgc tggagaagtg    960
gatcaacctg aaggtctccc tgtcttcctg cctctgtgtc agccaggagc tcatcttctg   1020
tggctgcaca gatgggatag tccgcatctt ccaggcccat agcctgcact acctcgccaa   1080
cctgcccaag ccacactacc ttggggtaga cgtggcacag gcctggagc ccagcttcct    1140
cttccacagg aaggcggaag cagtctaccc agatacagtg gcactgacct tcgacaccat   1200
ccaccagtgg ctgtcctgcg tgtataagga ccacagcatc tacatctggg atgtcaagga   1260
catcaacaga gtgggcaagg tgtggtcaga gctcttccac agctcctacg tttggaacgt   1320
ggaggtgtat cctgagtttg aagaccagag agcttgtttg ccatcaggat cctttctgac   1380
ttgttcttca gacaacacca ttcgcttctg gaacttggac agcagccctg attctcactg   1440
gcagaaaaac atcttcagca ataccctgct gaaggtcgtg tacgtggaga atgacatcca   1500
gcacctgcag gacatgtcac acttcccaga ccggggagc gagaatggga cacccatgga    1560
cgtgaaagcc ggggtgcggg tcatgcaggt cagtcctgac ggccagcatt tggcttcagg   1620
cgaccgaagt ggaaatctga ggatccacga gctgcacttc atggacgagc tggtcaaggt   1680
ggaggcccat gatgctgagg tgctgtgcct ggagtactcc aagccagaga cggggctgac   1740
cttgctggcc tcagccagtc gggaccggct gatccatgtg ctgaacgtgg agaagaacta   1800
caacctggag cagacgctgg atgaccactc ctcctccatc accgccatca gttcgctgg    1860
caacagagac atccagatga tcagctgtgg ggctgacaag agcatctact ttcgcagtgc   1920
ccagcagggt tcggatggac tacactttgt ccgtacccac cacgtagcag agaaaaccac   1980
cttgtatgac atggacattg acatcaccca gaagtacgtg gccgtggcct gccaggaccg   2040
caatgtgaga gtctacaaca ctgtgaacgg gaagcagaag aagtgctaca agggctccca   2100
gggtgacgaa gggtccttgc tgaaggtcca tgtggacccc tcaggcacct tcctggccac   2160
cagctgctct gacaaaagca tctcagtgat tgactttac tcgggcgagt gcattgccaa    2220
gatgtttggc cattcagaaa ttattaccag catgaagttc acctatgact gtcatcactt   2280
gatcacagta tctggagaca gctgcgtgtt catctggcac ctgggccgg agatcaccaa    2340
ctgcatgaag cagcacttgc tggagattga ccaccgcag cagcagcagc acacaaatga    2400
caagaagcgg agtggccacc ccaggcagga tacgtatgtg tccacaccta gtgagattca   2460
ctccctgagc cctggagagc aaacagagga tgatctggag gaagagtgtg agccagaaga   2520
gatgctgaag acaccatcca agatagcatt ggatccagat cctcgttgcc tgctaaccaa   2580
cggcaagctg ccactgtggg caaagcggct gctaggggac gatgatgtgg cagatggctt   2640
ggccttccac gccaagcgca gctaccagcc cacggccgc tgggcagagc gggccggcca    2700
agagcccctc aagaccatcc tggatgccca ggacctggat tgctacttta cccccatgaa   2760
gcccgagagt ctggagaact ccattctgga ttcactggag ccacagagcc tggccagcct   2820
gctgagtgag tcagagagtc cccaggaagc tggccgcggg cacccctcct tcctgcccca   2880
gcagaaggaa tcatctgagg ccagtgagct catcctctac tctctggagg cagaagtgac   2940
agtcacaggg acagacagcc agtattgcag gaaggaggtg gaggccgggc tggagaccca   3000
gcagggcgac tcctacctca gggtgtcctc cgacagccca aaggaccaga gcccgcctga   3060
ggactcgggg gagtcagagg ccgacctgga gtgcagcttc gcagccatcc actcccagc    3120
```

```
tccgcctcct gaccctgccc ctcggtttgc cacgtcgctg ccccatttcc caggatgcgc    3180
aggtcccaca gaagatgagc tgtccctgcc cgagggaccc agcgtcccca gcagctccct    3240
accccagact ccggagcagg agaagttcct ccgccaccac tttgagacac tgactgagtc    3300
cccctgcaga gagctcttcc ccgcagctct gggagacgtg gaggcctctg aagctgaaga    3360
ccacttcttc aacccacgcc tgagtatctc cacgcagttc ctctcaagcc tccagaaggc    3420
atccaggttc acccataacct tccctccccg ggcaacccag tgccttgtga agtctccaga    3480
ggtcaagctc atggaccgag gcggaagcca gcccagagca ggtactggct acgcctcccc    3540
agacaggacc cacgtcctcg ctgcagggaa ggctgaagag accctggagg cctggcgccc    3600
accacctccc tgccttacga gcctggcgtc ctgtgtccct gcttcctccg tgctgcccac    3660
agacaggaat ctcccaacgc ccacatctgc acccacccca ggcctggctc agggtgtcca    3720
tgcccccctcc acctgttcct acatggaggc cactgccagc tcccgtgcca ggatatcacg    3780
cagcatctcc ctcggtgaca gtgagggccc tatcgtggcc acactggccc agcccctccg    3840
taggccatcg tccgttgggg agctggcctc cttgggccag gagcttcagg ccatcaccac    3900
cgcgacaaca cccagtttgg acagtgaggg ccaagagcct gccctgcgtt cctggggcaa    3960
ccacgaggcc cgggccaacc tgagactgac cctgtcaagt gcctgtgatg ggctcctgca    4020
gcccccgtg ataccccagc ctggcgtcac cgtccctgca gtgagcttcc cagcccctag     4080
ccctgtggaa gagagcgccc tgaggctcca cggctctgcc tttcgcccaa gtctcccagc    4140
tcctgagtcc cctggccttc ctgcccaccc cagtaacccc cagcttccag aggcccggcc    4200
tggcatccct ggcggcactg cctccctcct ggagcccacc tccggtgcac ttggtctgtt    4260
acagggcagc cctgcccgct ggagtgagcc ctgggtgccg gttgaagccc tgcccccatc    4320
tcccccttgag ctgagcaggg tggggaacat cttgcacagg ctgcagacca ccttccaaga    4380
agccctcgac ctttaccgtg tgttggtctc cagtggccag gtggacaccg gcagcagca    4440
ggcacggact gagctggtct ccaccttcct gtggatccac agccagctgg aggctgaatg    4500
cctggtgggg actagtgtgg ccccagccca ggctctgccc agcccaggac cccgtcccc    4560
accgacgctg taccccctgg ccagcccaga cctgcaggcc ctgctggaac actactcgga    4620
gctgctggtg caggccgtgc ggaggaaggc acgggggcac tgagggcgca gcccctccac    4680
cgcagccctg ctgcttctga ggacttaggt attttaagcg aataaactga cagctttgag    4740
gaatga                                                               4746
```

<210> SEQ ID NO 2
<211> LENGTH: 1523
<212> TYPE: PRT
<213> ORGANISM: Homo sapiens

<400> SEQUENCE: 2

Met Ala Ala Val Gly Ser Gly Gly Tyr Ala Arg Asn Asp Ala Gly Glu
1               5                   10                  15

Lys Leu Pro Ser Val Met Ala Gly Val Pro Ala Arg Arg Gly Gln Ser
            20                  25                  30

Ser Pro Pro Pro Ala Pro Pro Ile Cys Leu Arg Arg Arg Thr Arg Leu
        35                  40                  45

Ser Thr Ala Ser Glu Glu Thr Val Gln Asn Arg Val Ser Leu Glu Lys
    50                  55                  60

Val Leu Gly Ile Thr Ala Gln Asn Ser Ser Gly Leu Thr Cys Asp Pro
65                  70                  75                  80

-continued

Gly Thr Gly His Val Ala Tyr Leu Ala Gly Cys Val Val Ile Leu
                85                  90                  95

Asp Pro Lys Glu Asn Lys Gln Gln His Ile Phe Asn Thr Ala Arg Lys
            100                 105                 110

Ser Leu Ser Ala Leu Ala Phe Ser Pro Asp Gly Lys Tyr Ile Val Thr
        115                 120                 125

Gly Glu Asn Gly His Arg Pro Ala Val Arg Ile Trp Asp Val Glu Glu
    130                 135                 140

Lys Asn Gln Val Ala Glu Met Leu Gly His Lys Tyr Gly Val Ala Cys
145                 150                 155                 160

Val Ala Phe Ser Pro Asn Met Lys His Ile Val Ser Met Gly Tyr Gln
                165                 170                 175

His Asp Met Val Leu Asn Val Trp Asp Trp Lys Lys Asp Ile Val Val
            180                 185                 190

Ala Ser Asn Lys Val Ser Cys Arg Val Ile Ala Leu Ser Phe Ser Glu
        195                 200                 205

Asp Ser Ser Tyr Phe Val Thr Val Gly Asn Arg His Val Arg Phe Trp
    210                 215                 220

Phe Leu Glu Val Ser Thr Glu Thr Lys Val Thr Ser Thr Val Pro Leu
225                 230                 235                 240

Val Gly Arg Ser Gly Ile Leu Gly Glu Leu His Asn Asn Ile Phe Cys
                245                 250                 255

Gly Val Ala Cys Gly Arg Gly Arg Met Ala Gly Ser Thr Phe Cys Val
            260                 265                 270

Ser Tyr Ser Gly Leu Leu Cys Gln Phe Asn Glu Lys Arg Val Leu Glu
        275                 280                 285

Lys Trp Ile Asn Leu Lys Val Ser Leu Ser Ser Cys Leu Cys Val Ser
    290                 295                 300

Gln Glu Leu Ile Phe Cys Gly Cys Thr Asp Gly Ile Val Arg Ile Phe
305                 310                 315                 320

Gln Ala His Ser Leu His Tyr Leu Ala Asn Leu Pro Lys Pro His Tyr
                325                 330                 335

Leu Gly Val Asp Val Ala Gln Gly Leu Glu Pro Ser Phe Leu Phe His
            340                 345                 350

Arg Lys Ala Glu Ala Val Tyr Pro Asp Thr Val Ala Leu Thr Phe Asp
        355                 360                 365

Pro Ile His Gln Trp Leu Ser Cys Val Tyr Lys Asp His Ser Ile Tyr
    370                 375                 380

Ile Trp Asp Val Lys Asp Ile Asn Arg Val Gly Lys Val Trp Ser Glu
385                 390                 395                 400

Leu Phe His Ser Ser Tyr Val Trp Asn Val Glu Val Tyr Pro Glu Phe
                405                 410                 415

Glu Asp Gln Arg Ala Cys Leu Pro Ser Gly Ser Phe Leu Thr Cys Ser
            420                 425                 430

Ser Asp Asn Thr Ile Arg Phe Trp Asn Leu Asp Ser Ser Pro Asp Ser
        435                 440                 445

His Trp Gln Lys Asn Ile Phe Ser Asn Thr Leu Leu Lys Val Val Tyr
    450                 455                 460

Val Glu Asn Asp Ile Gln His Leu Gln Asp Met Ser His Phe Pro Asp
465                 470                 475                 480

Arg Gly Ser Glu Asn Gly Thr Pro Met Asp Val Lys Ala Gly Val Arg
                485                 490                 495

Val Met Gln Val Ser Pro Asp Gly Gln His Leu Ala Ser Gly Asp Arg

```
                500             505             510
Ser Gly Asn Leu Arg Ile His Glu Leu His Phe Met Asp Glu Leu Val
            515             520             525

Lys Val Glu Ala His Asp Ala Glu Val Leu Cys Leu Glu Tyr Ser Lys
            530             535             540

Pro Glu Thr Gly Leu Thr Leu Leu Ala Ser Ala Ser Arg Asp Arg Leu
545             550             555             560

Ile His Val Leu Asn Val Glu Lys Asn Tyr Asn Leu Glu Gln Thr Leu
            565             570             575

Asp Asp His Ser Ser Ser Ile Thr Ala Ile Lys Phe Ala Gly Asn Arg
            580             585             590

Asp Ile Gln Met Ile Ser Cys Gly Ala Asp Lys Ser Ile Tyr Phe Arg
            595             600             605

Ser Ala Gln Gln Gly Ser Asp Gly Leu His Phe Val Arg Thr His His
            610             615             620

Val Ala Glu Lys Thr Thr Leu Tyr Asp Met Asp Ile Asp Ile Thr Gln
625             630             635             640

Lys Tyr Val Ala Val Ala Cys Gln Asp Arg Asn Val Arg Val Tyr Asn
            645             650             655

Thr Val Asn Gly Lys Gln Lys Lys Cys Tyr Lys Gly Ser Gln Gly Asp
            660             665             670

Glu Gly Ser Leu Leu Lys Val His Val Asp Pro Ser Gly Thr Phe Leu
            675             680             685

Ala Thr Ser Cys Ser Asp Lys Ser Ile Ser Val Ile Asp Phe Tyr Ser
            690             695             700

Gly Glu Cys Ile Ala Lys Met Phe Gly His Ser Glu Ile Ile Thr Ser
705             710             715             720

Met Lys Phe Thr Tyr Asp Cys His His Leu Ile Thr Val Ser Gly Asp
            725             730             735

Ser Cys Val Phe Ile Trp His Leu Gly Pro Glu Ile Thr Asn Cys Met
            740             745             750

Lys Gln His Leu Leu Glu Ile Asp His Arg Gln Gln Gln His Thr
            755             760             765

Asn Asp Lys Lys Arg Ser Gly His Pro Arg Gln Asp Thr Tyr Val Ser
770             775             780

Thr Pro Ser Glu Ile His Ser Leu Ser Pro Gly Glu Gln Thr Glu Asp
785             790             795             800

Asp Leu Glu Glu Glu Cys Glu Pro Glu Glu Met Leu Lys Thr Pro Ser
            805             810             815

Lys Asp Ser Leu Asp Pro Asp Pro Arg Cys Leu Leu Thr Asn Gly Lys
            820             825             830

Leu Pro Leu Trp Ala Lys Arg Leu Gly Asp Asp Val Ala Asp
            835             840             845

Gly Leu Ala Phe His Ala Lys Arg Ser Tyr Gln Pro His Gly Arg Trp
            850             855             860

Ala Glu Arg Ala Gly Gln Glu Pro Leu Lys Thr Ile Leu Asp Ala Gln
865             870             875             880

Asp Leu Asp Cys Tyr Phe Thr Pro Met Lys Pro Glu Ser Leu Glu Asn
            885             890             895

Ser Ile Leu Asp Ser Leu Glu Pro Gln Ser Leu Ala Ser Leu Leu Ser
            900             905             910

Glu Ser Glu Ser Pro Gln Glu Ala Gly Arg Gly His Pro Ser Phe Leu
            915             920             925
```

-continued

Pro Gln Gln Lys Glu Ser Ser Glu Ala Ser Glu Leu Ile Leu Tyr Ser
    930                 935                 940

Leu Glu Ala Glu Val Thr Val Thr Gly Thr Asp Ser Gln Tyr Cys Arg
945                 950                 955                 960

Lys Glu Val Glu Ala Gly Pro Gly Asp Gln Gln Gly Asp Ser Tyr Leu
                965                 970                 975

Arg Val Ser Ser Asp Ser Pro Lys Asp Gln Ser Pro Pro Glu Asp Ser
            980                 985                 990

Gly Glu Ser Glu Ala Asp Leu Glu Cys Ser Phe Ala Ala Ile His Ser
        995                 1000                1005

Pro Ala Pro Pro Asp Pro Ala Pro Arg Phe Ala Thr Ser Leu
    1010                1015                1020

Pro His Phe Pro Gly Cys Ala Gly Pro Thr Glu Asp Glu Leu Ser
    1025                1030                1035

Leu Pro Glu Gly Pro Ser Val Pro Ser Ser Ser Leu Pro Gln Thr
    1040                1045                1050

Pro Glu Gln Glu Lys Phe Leu Arg His His Phe Glu Thr Leu Thr
    1055                1060                1065

Glu Ser Pro Cys Arg Glu Leu Phe Pro Ala Ala Leu Gly Asp Val
    1070                1075                1080

Glu Ala Ser Glu Ala Glu Asp His Phe Phe Asn Pro Arg Leu Ser
    1085                1090                1095

Ile Ser Thr Gln Phe Leu Ser Ser Leu Gln Lys Ala Ser Arg Phe
    1100                1105                1110

Thr His Thr Phe Pro Pro Arg Ala Thr Gln Cys Leu Val Lys Ser
    1115                1120                1125

Pro Glu Val Lys Leu Met Asp Arg Gly Gly Ser Gln Pro Arg Ala
    1130                1135                1140

Gly Thr Gly Tyr Ala Ser Pro Asp Arg Thr His Val Leu Ala Ala
    1145                1150                1155

Gly Lys Ala Glu Glu Thr Leu Glu Ala Trp Arg Pro Pro Pro Pro
    1160                1165                1170

Cys Leu Thr Ser Leu Ala Ser Cys Val Pro Ala Ser Ser Val Leu
    1175                1180                1185

Pro Thr Asp Arg Asn Leu Pro Thr Pro Thr Ser Ala Pro Thr Pro
    1190                1195                1200

Gly Leu Ala Gln Gly Val His Ala Pro Ser Thr Cys Ser Tyr Met
    1205                1210                1215

Glu Ala Thr Ala Ser Ser Arg Ala Arg Ile Ser Arg Ser Ile Ser
    1220                1225                1230

Leu Gly Asp Ser Glu Gly Pro Ile Val Ala Thr Leu Ala Gln Pro
    1235                1240                1245

Leu Arg Arg Pro Ser Ser Val Gly Glu Leu Ala Ser Leu Gly Gln
    1250                1255                1260

Glu Leu Gln Ala Ile Thr Thr Ala Thr Thr Pro Ser Leu Asp Ser
    1265                1270                1275

Glu Gly Gln Glu Pro Ala Leu Arg Ser Trp Gly Asn His Glu Ala
    1280                1285                1290

Arg Ala Asn Leu Arg Leu Thr Leu Ser Ser Ala Cys Asp Gly Leu
    1295                1300                1305

Leu Gln Pro Pro Val Asp Thr Gln Pro Gly Val Thr Val Pro Ala
    1310                1315                1320

| | | | | | | | | | |
|---|---|---|---|---|---|---|---|---|---|
|Val|Ser|Phe|Pro|Ala|Pro|Ser|Pro|Val|Glu|Glu|Ser|Ala|Leu|Arg|
| |1325| | | |1330| | | |1335| | | | | |

Val Ser Phe Pro Ala Pro Ser Pro Val Glu Glu Ser Ala Leu Arg
    1325                1330                1335

Leu His Gly Ser Ala Phe Arg Pro Ser Leu Pro Ala Pro Glu Ser
    1340                1345                1350

Pro Gly Leu Pro Ala His Pro Ser Asn Pro Gln Leu Pro Glu Ala
    1355                1360                1365

Arg Pro Gly Ile Pro Gly Gly Thr Ala Ser Leu Leu Glu Pro Thr
    1370                1375                1380

Ser Gly Ala Leu Gly Leu Leu Gln Gly Ser Pro Ala Arg Trp Ser
    1385                1390                1395

Glu Pro Trp Val Pro Val Glu Ala Leu Pro Pro Ser Pro Leu Glu
    1400                1405                1410

Leu Ser Arg Val Gly Asn Ile Leu His Arg Leu Gln Thr Thr Phe
    1415                1420                1425

Gln Glu Ala Leu Asp Leu Tyr Arg Val Leu Val Ser Ser Gly Gln
    1430                1435                1440

Val Asp Thr Gly Gln Gln Gln Ala Arg Thr Glu Leu Val Ser Thr
    1445                1450                1455

Phe Leu Trp Ile His Ser Gln Leu Glu Ala Glu Cys Leu Val Gly
    1460                1465                1470

Thr Ser Val Ala Pro Ala Gln Ala Leu Pro Ser Pro Gly Pro Pro
    1475                1480                1485

Ser Pro Pro Thr Leu Tyr Pro Leu Ala Ser Pro Asp Leu Gln Ala
    1490                1495                1500

Leu Leu Glu His Tyr Ser Glu Leu Leu Val Gln Ala Val Arg Arg
    1505                1510                1515

Lys Ala Arg Gly His
    1520

<210> SEQ ID NO 3
<211> LENGTH: 4744
<212> TYPE: DNA
<213> ORGANISM: Mus musculus

<400> SEQUENCE: 3

```
ggctttcccg cggccattcg ctattcgagt gggtgctggc tacaggcggc tgttaagaag      60
cgtaacggac actggtctcc gacagcatga tggctgcctt agcggccgga ggttatacgc     120
ggagtgacac gatagaaaag ctgtcctctg tcatggcggg agttccggcg cggagaaacc     180
agtcctcccc gcctcctgcc ccaccgctct gcctccggcg gcggacgcga ctcgcggcgg     240
ctcccgagga cactgtgcag aaccgggtga cacttgagaa ggtgcttggc atcacagccc     300
agaacagcag cgggctaacc tgtgaccctg gcacaggcca tgtggcctac ttagcagggt     360
gcgtggtggt ggtcttgaac cccaaggaga acaagcagca gcatatattt aacacaacca     420
ggaagtccct gagtgctctg gccttctccc cagatgggaa gtacatagtg acaggagaga     480
atggacaccg gccagctgtg cgcatctggg atgtggagga aagactcaa gtggcagaga     540 tgctgggcca aagtatggt gtggcctgtg tggctttctc acccaatatg aagcacatcg     600
tgtccatggg ctaccaacat gacatggtcc tcaatgtttg ggattggaag aaagacattg     660
tggtggcttc caacaaggtg tcatgtagag tcatcgctct ctccttctct gaggacagca     720
gctattttgt caccgttggg aatcggcatg tgaggttttg gttcttagaa gcctctactg     780
aggccaaggt aaccagcaca gtgccctgta ggacgctc aggcatcctg ggtgagctgc     840
acaacaatat cttttgtggc gtggcctgcg gccggggccg gatggcaggc aatacctct     900
```

```
gtgtgtccta ctctggcctc tctgccagt tcaatgagaa aagggtgctg acaagtgga     960 tcaacctgaa ggtctccttg tcttcctgcc tgtgtgtcag tgacgagttg atcttctgtg  1020
gatgcacaga cgggatagtc cgcatcttcc aggcccacag cctactctac ctcaccaacc  1080
tgcccaaacc acactacctg ggagtggacg tgcccacgg actggactcc agcttcctct   1140
tccacagaaa agcagaagca gtctacccag atacagtggc cctgaccttt gacccgtcc   1200 accagtggct gtcctgtgtt tacaaagacc acagcatcta catctgggat gtcaaggaca  1260
ttgatgaagt cagcaagata tggtcagagc tcttccacag ctccttgtc tggaatgtag   1320 aggtgtaccc tgaatttgaa gaccagagag cttgcctgcc gtccgggact tttctgactt  1380
gttcctcaga ataccatc cgcttctgga atttggatag cgcctctgac actcgatggc    1440
aaaagaacat cttcagcgat tctctgctga aggtggtcta tgtagagaat gacatccagc  1500
acctgcagga cctgtctcac ttcccagacc ggggcagtga aacggcact cccatggata   1560 tgaaagctgg ggttcgagtc atgcaggtca gtcctgacgg ccagcacttg gcttcaggcg  1620
accgcagtgg aaatctgagg atccacgagc tgcacttcat ggatgagctg atcaaggtgg  1680
aggcccacga tgctgaggtg ctgtgcctgg agtactccaa gcctgagaca ggagtgactt  1740
tgctggcttc agccagtcgg gacagactca tccatgtgtt aaacgtggag aagaactaca  1800
acctggagca gaccctggac gaccactcct cctccatcac agccattaag tttgctggca  1860
ccagagatgt ccagatgatc agttgtggag ctgacaagag catctacttt cgcagtgccc  1920
agcaggcctc ggatggactg cactttgtcc gtacccacca cgtagcagag aagaccacct  1980
tgtatgacat ggatatcgac atcacacaga agtatgtggc agtggcctgc caggaccgca  2040
acgtaagggt ctacaacacc gtgagtggga aacagaagaa gtgctacaag ggttcccagg  2100
gcgacgaagg gtccctgctg aaggtccacg tggacccctc aggcaccttc ctggccacaa  2160
gctgctctga caaaagcatc tccttgattg acttttactc gggcgagtgt gttgccaaga  2220
tgtttggcca ttcggaaatt gtcactggca tgaagttcac ctacgactgc cgccacttga  2280
tcacagtatc tggagacagc tgtgtgttca tctggcacct gggcccggag atcaccacct  2340
gcatgaagca gcacttgctg gagatcaacc accaggagca gcagcagcag cccaaggacc  2400
agaagtggag tggccctccc agccaggaga catatgcatc cacaccaagt gagattcgtt  2460
ccctgagccc tggagagcag acagaggatg agatggagga ggaatgtgag ccagaagagt  2520
tgctgaaaac accatccaaa gacagcttgg acccagatcc tcgatgcctg ctgacaaatg  2580
gcaagctgcc actctgggca aagcggctgc taggggatga tgatgtggca gacagctcag  2640 cttttccacgc caagcgcagc taccagccac atggccgttg ggcagagcgg gctgagcagg  2700
aacccctcaa gaccatcctg gatgcctgga gcctggattc ctactttaca cccatgaagc  2760
ctgaaaatct ccaagactct gttctggact cagtagagcc acagaacctg gcaggcctgc  2820
taagtgagtg ttcactcggt aatggacaca cgtctccggg agaaggcttg gtgagctacc  2880
tacttcaccc agagttaggg agtcccaaag aggacaaccg aggccacccc tcctacctgc  2940
ctctacagag ggaagccacc gaggcaagcg aactcatcct ctgctcccca gaggcggaag  3000
tgtcacttac agggatgcac agggagtatt atgaggagga gacagaggca ggacctgaag  3060
accagcaagg cgacacctat ctcagggtct cttccgtcag ttcaaaggat cagagccccc  3120
ctgaggactc aggggagtca gaggctgaac tggagtgcag ctttgccgcc gcccacagct  3180
cagctcctca aacggaccct ggccctcacc tcaccatgac agcaggtaag ccagagtacc  3240
```

```
caagtacaga agagctttcc cagcctgagc tgccaggctt gggcaatggc tccttacccc    3300
agacacctga gcaggagaag ttcctccgcc accattttga dacacttact gatgccccta    3360
ctgaagagct ctttcatgga tccctgggag acataaagat ctcagagact gaggactatt    3420
tcttcaatcc ccggctgagc atatccaccc agttcctctc ccgcctccag aagacctcca    3480
ggtgccctcc ccgactgccc ctgcacctta tgaagtctcc agaggctcag cctgtgggcc    3540 aaggggggcaa ccagcccaaa gcagggcccc tgagagcagg tactggctac atgtcctcag    3600
atgggaccaa cgtcctctct gggcagaagg ctgaagaaac tcaagaggcc ttgagtctac    3660
tggacaggaa gcctccaaca cccacatctg tactgaccac aggccgggag caaagtatct    3720 ccgcccccatc ttcgtgttct tacctggagt ccacaacgag ctcacatgcc aagacgacac    3780
gcagcatctc tcttggggac agtgagggcc ctgtgacagc tgagctaccc cagtcacttc    3840 acaagcccctt atccctggc caggaactcc aagccatccc cactacagtg gcactgacct    3900
ccagcatcaa agaccacgag cctgcaccgc tttcctgggg caaccatgag gcccgagcca    3960 gcctgaaaact gaccttatcc agtgtctgtg agcagctgct ctctccacct ccacaggagc    4020
cacccatcac ccatgtgtgg tctcaggaac ctgtggatgt cccacctagt atggcagtca    4080
cagtagccag cttctgtgca cccagccctg tagacatgag caccctggga ctccacagtt    4140
ctatgtttct cccaaagacc tcagcctctg ggcccctaac ccctcctgcc cacctccaac    4200
ttctagagac caggtctagg gtgcctggca gcactgctgc tctcctggag cccaccccccg    4260 atgcatcagg tgtgatcgca gacagccctg gacactggga cacagaagtc cctaccccag    4320
aactcctagg cagtgtggaa tcagtcttgc acaggctgca gactgccttc caagaagctc    4380 ttgacccttta ccgcatgctg gtctccagca gccagctggg tcctgagcag cagcaggcac    4440
agaccgagct ggcctccacc ttccactgga tcctcaacca gctagaagcc agcaactgta    4500
tggctgcagc taacttggcc ccaccccaga cactgcctag cccagaccct ctgtccctac    4560
ctacactttg tccccctggcc agcccaaacc tgcaggccct gctggaacac tactcagagt    4620
tgctggtgca agcagtgagg aggaaggcaa ggggtgactg agaacctgaa gcccctctac    4680
caaagccccg ctgccctgga gaaatagatt tgtaaaccaa taaactgaca gttgtttcct    4740
ggaa                                                                 4744
```

<210> SEQ ID NO 4
<211> LENGTH: 1524
<212> TYPE: PRT
<213> ORGANISM: Mus musculus

<400> SEQUENCE: 4

Met Met Ala Ala Leu Ala Ala Gly Gly Tyr Thr Arg Ser Asp Thr Ile
1               5                   10                  15

Glu Lys Leu Ser Ser Val Met Ala Gly Val Pro Ala Arg Arg Asn Gln
            20                  25                  30

Ser Ser Pro Pro Pro Ala Pro Pro Leu Cys Leu Arg Arg Arg Thr Arg
        35                  40                  45

Leu Ala Ala Ala Pro Glu Asp Thr Val Gln Asn Arg Val Thr Leu Glu
    50                  55                  60

Lys Val Leu Gly Ile Thr Ala Gln Asn Ser Ser Gly Leu Thr Cys Asp
65                  70                  75                  80

Pro Gly Thr Gly His Val Ala Tyr Leu Ala Gly Cys Val Val Val Val
                85                  90                  95

Leu Asn Pro Lys Glu Asn Lys Gln Gln His Ile Phe Asn Thr Thr Arg

```
            100                 105                 110
Lys Ser Leu Ser Ala Leu Ala Phe Ser Pro Asp Gly Lys Tyr Ile Val
            115                 120                 125

Thr Gly Glu Asn Gly His Arg Pro Ala Val Arg Ile Trp Asp Val Glu
130                 135                 140

Glu Lys Thr Gln Val Ala Glu Met Leu Gly His Lys Tyr Gly Val Ala
145                 150                 155                 160

Cys Val Ala Phe Ser Pro Asn Met Lys His Ile Val Ser Met Gly Tyr
            165                 170                 175

Gln His Asp Met Val Leu Asn Val Trp Asp Trp Lys Lys Asp Ile Val
            180                 185                 190

Val Ala Ser Asn Lys Val Ser Cys Arg Val Ile Ala Leu Ser Phe Ser
            195                 200                 205

Glu Asp Ser Ser Tyr Phe Val Thr Val Gly Asn Arg His Val Arg Phe
            210                 215                 220

Trp Phe Leu Glu Ala Ser Thr Glu Ala Lys Val Thr Ser Thr Val Pro
225                 230                 235                 240

Leu Val Gly Arg Ser Gly Ile Leu Gly Glu Leu His Asn Asn Ile Phe
            245                 250                 255

Cys Gly Val Ala Cys Gly Arg Gly Arg Met Ala Gly Asn Thr Phe Cys
            260                 265                 270

Val Ser Tyr Ser Gly Leu Leu Cys Gln Phe Asn Glu Lys Arg Val Leu
            275                 280                 285

Asp Lys Trp Ile Asn Leu Lys Val Ser Leu Ser Ser Cys Leu Cys Val
            290                 295                 300

Ser Asp Glu Leu Ile Phe Cys Gly Cys Thr Asp Gly Ile Val Arg Ile
305                 310                 315                 320

Phe Gln Ala His Ser Leu Leu Tyr Leu Thr Asn Leu Pro Lys Pro His
            325                 330                 335

Tyr Leu Gly Val Asp Val Ala His Gly Leu Asp Ser Ser Phe Leu Phe
            340                 345                 350

His Arg Lys Ala Glu Ala Val Tyr Pro Asp Thr Val Ala Leu Thr Phe
            355                 360                 365

Asp Pro Val His Gln Trp Leu Ser Cys Val Tyr Lys Asp His Ser Ile
370                 375                 380

Tyr Ile Trp Asp Val Lys Asp Ile Asp Glu Val Ser Lys Ile Trp Ser
385                 390                 395                 400

Glu Leu Phe His Ser Ser Phe Val Trp Asn Val Glu Val Tyr Pro Glu
            405                 410                 415

Phe Glu Asp Gln Arg Ala Cys Leu Pro Ser Gly Thr Phe Leu Thr Cys
            420                 425                 430

Ser Ser Asp Asn Thr Ile Arg Phe Trp Asn Leu Asp Ser Ala Ser Asp
            435                 440                 445

Thr Arg Trp Gln Lys Asn Ile Phe Ser Asp Ser Leu Leu Lys Val Val
450                 455                 460

Tyr Val Glu Asn Asp Ile Gln His Leu Gln Asp Leu Ser His Phe Pro
465                 470                 475                 480

Asp Arg Gly Ser Glu Asn Gly Thr Pro Met Asp Met Lys Ala Gly Val
            485                 490                 495

Arg Val Met Gln Val Ser Pro Asp Gly Gln His Leu Ala Ser Gly Asp
            500                 505                 510

Arg Ser Gly Asn Leu Arg Ile His Glu Leu His Phe Met Asp Glu Leu
            515                 520                 525
```

```
Ile Lys Val Glu Ala His Asp Ala Glu Val Leu Cys Leu Glu Tyr Ser
    530                 535                 540

Lys Pro Glu Thr Gly Val Thr Leu Leu Ala Ser Ala Ser Arg Asp Arg
545                 550                 555                 560

Leu Ile His Val Leu Asn Val Glu Lys Asn Tyr Asn Leu Glu Gln Thr
                565                 570                 575

Leu Asp Asp His Ser Ser Ser Ile Thr Ala Ile Lys Phe Ala Gly Thr
                580                 585                 590

Arg Asp Val Gln Met Ile Ser Cys Gly Ala Asp Lys Ser Ile Tyr Phe
                595                 600                 605

Arg Ser Ala Gln Gln Ala Ser Asp Gly Leu His Phe Val Arg Thr His
    610                 615                 620

His Val Ala Glu Lys Thr Thr Leu Tyr Asp Met Asp Ile Asp Ile Thr
625                 630                 635                 640

Gln Lys Tyr Val Ala Val Ala Cys Gln Asp Arg Asn Val Arg Val Tyr
                645                 650                 655

Asn Thr Val Ser Gly Lys Gln Lys Lys Cys Tyr Lys Gly Ser Gln Gly
                660                 665                 670

Asp Glu Gly Ser Leu Leu Lys Val His Val Asp Pro Ser Gly Thr Phe
                675                 680                 685

Leu Ala Thr Ser Cys Ser Asp Lys Ser Ile Ser Leu Ile Asp Phe Tyr
    690                 695                 700

Ser Gly Glu Cys Val Ala Lys Met Phe Gly His Ser Glu Ile Val Thr
705                 710                 715                 720

Gly Met Lys Phe Thr Tyr Asp Cys Arg His Leu Ile Thr Val Ser Gly
                725                 730                 735

Asp Ser Cys Val Phe Ile Trp His Leu Gly Pro Glu Ile Thr Thr Cys
                740                 745                 750

Met Lys Gln His Leu Leu Glu Ile Asn His Gln Glu Gln Gln Gln Gln
                755                 760                 765

Pro Lys Asp Gln Lys Trp Ser Gly Pro Pro Ser Gln Glu Thr Tyr Ala
    770                 775                 780

Ser Thr Pro Ser Glu Ile Arg Ser Leu Ser Pro Gly Glu Gln Thr Glu
785                 790                 795                 800

Asp Glu Met Glu Glu Glu Cys Glu Pro Glu Glu Leu Leu Lys Thr Pro
                805                 810                 815

Ser Lys Asp Ser Leu Asp Pro Asp Pro Arg Cys Leu Leu Thr Asn Gly
                820                 825                 830

Lys Leu Pro Leu Trp Ala Lys Arg Leu Leu Gly Asp Asp Asp Val Ala
                835                 840                 845

Asp Ser Ser Ala Phe His Ala Lys Arg Ser Tyr Gln Pro His Gly Arg
    850                 855                 860

Trp Ala Glu Arg Ala Glu Gln Glu Pro Leu Lys Thr Ile Leu Asp Ala
865                 870                 875                 880

Trp Ser Leu Asp Ser Tyr Phe Thr Pro Met Lys Pro Glu Asn Leu Gln
                885                 890                 895

Asp Ser Val Leu Asp Ser Val Glu Pro Gln Asn Leu Ala Gly Leu Leu
                900                 905                 910

Ser Glu Cys Ser Leu Gly Asn Gly His Thr Ser Pro Gly Glu Gly Leu
                915                 920                 925

Val Ser Tyr Leu Leu His Pro Glu Leu Gly Ser Pro Lys Glu Asp Asn
    930                 935                 940
```

```
Arg Gly His Pro Ser Tyr Leu Pro Leu Gln Arg Glu Ala Thr Glu Ala
945                 950                 955                 960

Ser Glu Leu Ile Leu Cys Ser Pro Glu Ala Glu Val Ser Leu Thr Gly
                965                 970                 975

Met His Arg Glu Tyr Tyr Glu Glu Thr Glu Ala Gly Pro Glu Asp
            980                 985                 990

Gln Gln Gly Asp Thr Tyr Leu Arg  Val Ser Ser Val Ser  Ser Lys Asp
        995                 1000                1005

Gln Ser  Pro Pro Glu Asp Ser  Gly Glu Ser Glu Ala  Glu Leu Glu
    1010                1015                1020

Cys Ser  Phe Ala Ala Ala His  Ser Ser Ala Pro Gln  Thr Asp Pro
    1025                1030                1035

Gly Pro  His Leu Thr Met Thr  Ala Gly Lys Pro Glu  Tyr Pro Ser
    1040                1045                1050

Thr Glu  Glu Leu Ser Gln Pro  Glu Leu Pro Gly Leu  Gly Asn Gly
    1055                1060                1065

Ser Leu  Pro Gln Thr Pro Glu  Gln Glu Lys Phe Leu  Arg His His
    1070                1075                1080

Phe Glu  Thr Leu Thr Asp Ala  Pro Thr Glu Glu Leu  Phe His Gly
    1085                1090                1095

Ser Leu  Gly Asp Ile Lys Ile  Ser Glu Thr Glu Asp  Tyr Phe Phe
    1100                1105                1110

Asn Pro  Arg Leu Ser Ile Ser  Thr Gln Phe Leu Ser  Arg Leu Gln
    1115                1120                1125

Lys Thr  Ser Arg Cys Pro Pro  Arg Leu Pro Leu His  Leu Met Lys
    1130                1135                1140

Ser Pro  Glu Ala Gln Pro Val  Gly Gln Gly Gly Asn  Gln Pro Lys
    1145                1150                1155

Ala Gly  Pro Leu Arg Ala Gly  Thr Gly Tyr Met Ser  Ser Asp Gly
    1160                1165                1170

Thr Asn  Val Leu Ser Gly Gln  Lys Ala Glu Glu Thr  Gln Glu Ala
    1175                1180                1185

Leu Ser  Leu Leu Asp Arg Lys  Pro Pro Thr Pro Thr  Ser Val Leu
    1190                1195                1200

Thr Thr  Gly Arg Glu Gln Ser  Ile Ser Ala Pro Ser  Ser Cys Ser
    1205                1210                1215

Tyr Leu  Glu Ser Thr Thr Ser  Ser His Ala Lys Thr  Thr Arg Ser
    1220                1225                1230

Ile Ser  Leu Gly Asp Ser Glu  Gly Pro Val Thr Ala  Glu Leu Pro
    1235                1240                1245

Gln Ser  Leu His Lys Pro Leu  Ser Pro Gly Gln Glu  Leu Gln Ala
    1250                1255                1260

Ile Pro  Thr Thr Val Ala Leu  Thr Ser Ser Ile Lys  Asp His Glu
    1265                1270                1275

Pro Ala  Pro Leu Ser Trp Gly  Asn His Glu Ala Arg  Ala Ser Leu
    1280                1285                1290

Lys Leu  Thr Leu Ser Ser Val  Cys Glu Gln Leu Leu  Ser Pro Pro
    1295                1300                1305

Pro Gln  Glu Pro Pro Ile Thr  His Val Trp Ser Gln  Glu Pro Val
    1310                1315                1320

Asp Val  Pro Pro Ser Met Ala  Val Thr Val Ala Ser  Phe Cys Ala
    1325                1330                1335

Pro Ser  Pro Val Asp Met Ser  Thr Leu Gly Leu His  Ser Ser Met
```

-continued

```
            1340                1345                1350
Phe Leu Pro Lys Thr Ser Ala Ser Gly Pro Leu Thr Pro Pro Ala
        1355                1360                1365

His Leu Gln Leu Leu Glu Thr Arg Ser Arg Val Pro Gly Ser Thr
        1370                1375                1380

Ala Ala Leu Leu Glu Pro Thr Pro Asp Ala Ser Gly Val Ile Ala
        1385                1390                1395

Asp Ser Pro Gly His Trp Asp Thr Glu Val Pro Thr Pro Glu Leu
        1400                1405                1410

Leu Gly Ser Val Glu Ser Val Leu His Arg Leu Gln Thr Ala Phe
        1415                1420                1425

Gln Glu Ala Leu Asp Leu Tyr Arg Met Leu Val Ser Ser Ser Gln
        1430                1435                1440

Leu Gly Pro Glu Gln Gln Gln Ala Gln Thr Glu Leu Ala Ser Thr
        1445                1450                1455

Phe His Trp Ile Leu Asn Gln Leu Glu Ala Ser Asn Cys Met Ala
        1460                1465                1470

Ala Ala Asn Leu Ala Pro Pro Gln Thr Leu Pro Ser Pro Asp Pro
        1475                1480                1485

Leu Ser Leu Pro Thr Leu Cys Pro Leu Ala Ser Pro Asn Leu Gln
        1490                1495                1500

Ala Leu Leu Glu His Tyr Ser Glu Leu Leu Val Gln Ala Val Arg
        1505                1510                1515

Arg Lys Ala Arg Gly Asp
        1520
```